United States Patent
Kanstrup et al.

(10) Patent No.: US 7,192,952 B2
(45) Date of Patent: *Mar. 20, 2007

(54) HETEROCYCLIC COMPOUNDS THAT ARE INHIBITORS OF THE ENZYME DPP-IV

(75) Inventors: Anders Bendtz Kanstrup, Espergaerde (DK); Christian Klarner Sams, Frederiksberg (DK); Jane Marie Lundbeck, Glostrup (DK); Lise Brown Christiansen, Lyngby (DK); Marit Kristiansen, Soborg (DK)

(73) Assignee: Novo Nordisk, A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 11/070,056

(22) Filed: Mar. 2, 2005

(65) Prior Publication Data
US 2005/0148606 A1   Jul. 7, 2005

Related U.S. Application Data

(63) Continuation of application No. 10/186,498, filed on Jun. 28, 2002, now Pat. No. 6,869,947.
(60) Provisional application No. 60/356,631, filed on Feb. 8, 2002, provisional application No. 60/309,621, filed on Aug. 2, 2001.

(30) Foreign Application Priority Data

| Jul. 3, 2001 | (DK) | ................................ 2001 01049 |
| Feb. 6, 2002 | (DK) | ................................ 2002 00180 |

(51) Int. Cl.
C07D 473/08 (2006.01)
C07D 473/06 (2006.01)
A61K 31/522 (2006.01)
A61K 31/55 (2006.01)
A61P 3/10 (2006.01)

(52) U.S. Cl. .............................. 514/217.06; 514/263.2; 514/263.22; 544/269; 544/272; 540/600

(58) Field of Classification Search ........... 514/217.06, 514/263.2, 263.22; 544/272, 269; 540/600
See application file for complete search history.

(56) References Cited

U.S. PATENT DOCUMENTS 6,060,481 A   5/2000   LaNoue et al.

6,869,947 B2 *   3/2005   Kanstrup et al. ...... 514/217.06

FOREIGN PATENT DOCUMENTS

| EP | 1054012 A1 | 12/1998 |
| WO | WO 94/02150 | 2/1994 |
| WO | WO 02/02560 A2 | 1/2002 |
| WO | WO 02/24698 A1 | 3/2002 |
| WO | WO 02/068420 A1 | 9/2002 |

OTHER PUBLICATIONS

Holst et al., Diabetes, vol. 47, pp. 1663-1670 (1998).

* cited by examiner

*Primary Examiner*—Kahsay Habte
(74) *Attorney, Agent, or Firm*—Rosemarie R. Wilk-Orescan; Reza Green; Richard W. Bork

(57) ABSTRACT

The present invention relates to therapeutically active and selective inhibitors of the enzyme DPP-IV of formula I, pharmaceutical compositions comprising the compounds and the use of such compounds for and the manufacture of medicaments for treating diseases that are associated with proteins that are subject to inactivation by DPP-IV, such as type 2 diabetes and obesity

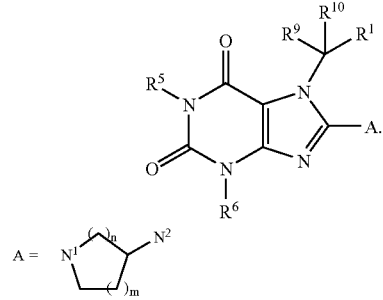

Formula I 3 Claims, No Drawings

HETEROCYCLIC COMPOUNDS THAT ARE INHIBITORS OF THE ENZYME DPP-IV

CROSS-REFERENCE TO RELATED APPLICATIONS

This application is a continuation of U.S. application Ser. No. 10/186,498 filed on Jun. 28, 2002 now U.S. Pat. No. 6,869,947 and claims priority of U.S. provisional application Nos. 60/309,621 filed Aug. 2, 2001 and 60/356,631 filed Feb. 8, 2002 and claims priority of Danish application nos. PA 2001 01049 filed Jul. 3, 2001 and PA 2002 00180 filed Feb. 6, 2002, the contents of which are fully incorporated herein by reference.

FIELD OF THE INVENTION

The present invention relates to therapeutically active and selective inhibitors of the enzyme DPP-IV, pharmaceutical compositions comprising the compounds and the use of such compounds for and the manufacture of medicaments for treating diseases that are associated with proteins that are subject to inactivation by DPP-IV, such as type 2 diabetes and obesity.

BACKGROUND OF THE INVENTION

Dipeptidyl peptidase-IV (DPP-IV), a serine protease belonging to the group of post-proline/alanine cleaving amino-dipeptidases, specifically removes the two N-terminal amino acids from proteins having proline or alanine in position 2.

Although the physiological role of DPP-IV has not been completely established, it is believed to play an important role in neuropeptide metabolism, T-cell activation, gastric ulceration, functional dyspepsia, obesity, appetite regulation, impaired fasting glucose (IFG) and diabetes.

DPP-IV has been implicated in the control of glucose metabolism because its substrates include the insulinotropic hormones Glucagon like peptide-1 (GLP-1) and Gastric inhibitory peptide (GIP). GLP-1 and GIP are active only in their intact forms, removal of their two N-terminal amino acids inactivates them.

In vivo administration of synthetic inhibitors of DPP-IV prevents N-terminal degradation of GLP-1 and GIP, resulting in higher plasma concentrations of these hormones, increased insulin secretion and, therefore, improved glucose tolerance. Therefore, such inhibitors have been proposed for the treatment of patients with Type 2 diabetes, a disease characterised by decreased glucose tolerance. (Holst, J. J., Deacon, C. F. Diabetes 47 (1998) 1663–70).

Diabetic dyslipidemia is characterized by multiple lipoprotein defects, including moderately high serum levels of cholesterol and triglycerides, small LDL particles, and low levels of HDL cholesterol. The results of recent clinical trials reveal beneficial effects of cholesterol-lowering therapy in diabetic and non-diabetic patients, thus supporting increased emphasis on treatment of diabetic dyslipidemia. The National Cholesterol Education Program's Adult Treatment Panel II advocated this need for intensive treatment of diabetic dyslipidemia.

Obesity is a well-known risk factor for the development of many very common diseases such as atherosclerosis, hypertension and diabetes. The incidence of obese people and thereby also these diseases is increasing throughout the entire industrialised world. Except for exercise, diet and food restriction no convincing pharmacological treatment for reducing body weight effectively and acceptably currently exist. However, due to its indirect but important effect as a risk factor in mortal and common diseases it will be important to find treatment for obesity or appetite regulation. Even mild obesity increases the risk for premature death, diabetes, hypertension, atherosclerosis, gallbladder disease and certain types of cancer. In the industrialised western world the prevalence of obesity has increased significantly in the past few decades. Because of the high prevalence of obesity and its health consequences, its prevention and treatment should be a high public health priority. At present a variety of techniques are available to effect initial weight loss. Unfortunately, initial weight loss is not an optimal therapeutic goal. Rather, the problem is that most obese patients eventually regain their weight. An effective means to establish and/or sustain weight loss is the major challenge in the treatment of obesity today.

Several compounds have been shown to inhibit DPP-IV, but all of these have limitations in relation to the potency, stability, selectivity, toxicity, and pharmacodynamic properties. Thus, there is a need for the provision of DPP-IV inhibitors that are superior with respect to one or more of the above listed properties, and which will be useful for the treatment of conditions, which may be regulated or normalised by inhibition of DPP-IV.

SUMMARY OF THE INVENTION

The present invention consists of novel purine derivatives, attached at position 8 of the purine skeleton to a cyclic diamine, at either one or the other of the amino groups of the diamine. The compounds of the present invention are thus not amino acid derivatives, such as the presently known DPP-IV inhibitors, but consist of structural elements hitherto unrelated to DPP-IV inhibition, and as such they represent novel solutions to the problem of finding an optimal DPP-IV inhibitor. These compounds are potent and selective inhibitors of DPP-IV, and are effective in treating conditions that may be regulated or normalised via inhibition of DPP-IV. The invention also concerns methods for preparing the compounds, pharmaceutical compositions comprising the compounds, a method of inhibiting DPP-IV comprising administering to a patient in need of such treatment a therapeutically effective amount thereof, the compounds for use as a pharmaceutical, and their use in a process for the preparation of a medicament for treating a condition which may be regulated or normalised via inhibition of DPP-IV.

Definitions

The term "DPP-IV" as used herein is intended to mean Dipeptidyl peptidase IV (EC 3.4.14.5, DPP-IV), also known as CD26. DPP-IV cleaves a dipeptide from the N terminus of a polypeptide chain containing a proline or alanine residue in the penultimate position.

The term "treatment" is defined as the management and care of a patient for the purpose of combating the disease, condition, or disorder and includes the administration of a compound of the present invention to prevent the onset of the symptoms or complications, or alleviating the symptoms or complications, or eliminating the disease, condition, or disorder.

The term "beta cell degeneration" is intended to mean loss of beta cell function, beta cell dysfunction, and death of beta cells, such as necrosis or apoptosis of beta cells.

The term "$C_1$–$C_{10}$ alkyl" as used herein, alone or in combination, refers to a straight or branched, saturated hydrocarbon chain having from 1–10 carbon atoms such as but not limited to e.g. methyl, ethyl, n-propyl, isopropyl, n-butyl, sec. Butyl, isobutyl, tert. Butyl, n-pentyl, 2-methylbutyl, 3-methylbutyl, n-hexyl, 4-methylpentyl, neopentyl, 2,2-dimethylpropyl and the like.

The term "$C_2$–$C_{10}$-alkenyl" used herein, alone or in combination, refers to a straight or branched, unsaturated hydrocarbon chain having from 2–10 carbon atoms and at least one double bond such as but not limited to vinyl, 1-propenyl, allyl, isopropenyl, n-butenyl, n-pentenyl and n-hexenyl and the like.

The term "$C_2$–$C_{10}$ alkynyl" as used herein, alone or in combination, refers to an unsaturated hydrocarbon chain having from 2–10 carbon atoms and at least one triple bond such as but not limited to —C≡CH, —C≡CCH$_3$, —CH$_2$C≡CH, —CH$_2$—CH$_2$—C≡CH, —CH(CH$_3$)C≡CH and the like.

The term "$C_1$–$C_{10}$-alkoxy" as used herein, alone or in combination is intended to include those $C_1$–$C_{10}$-alkyl groups of the designated length in either a linear or branched or cyclic configuration linked through an ether oxygen having its free valence bond from the ether oxygen. Examples of linear alkoxy groups are methoxy, ethoxy, propoxy, butoxy, pentoxy and hexoxy. Examples of branched alkoxy are isopropoxy, sec-butoxy, tert-butoxy, isopentoxy and isohexoxy. Examples of cyclic alkoxy are cyclopropyloxy, cyclobutyloxy, cyclopentyloxy and cyclohexyloxy.

The term "$C_3$–$C_{10}$ cycloalkyl" as used herein refers to a radical of one or more saturated cyclic hydrocarbon having from 3–10 carbon atoms such as but not limited to cyclopropyl, cyclobutyl, cyclopentyl, cyclohexyl, adamantyl and the like.

The term "$C_3$–$C_{10}$ cycloalkane" as used herein refers to a saturated cyclic hydrocarbon having from 3–10 carbon atoms such as but not limited to cyclopropane, cyclobutane, cyclopentane, cyclohexane, adamantane and the like.

The term "$C_5$–$C_{10}$ cycloalkenyl" as used herein refers to a radical of one or more cyclic hydrocarbon having at least one double bond having from 5–10 carbon atoms such as but not limited to cyclopentenyl, cyclohexenyl and the like.

The term "$C_3$–$C_7$ cycloheteroalkyl" as used herein refers to a radical of totally saturated heterocycle like a cyclic hydrocarbon containing one or more heteroatoms selected from nitrogen, oxygen and sulphur independently in the cycle such as pyrrolidine (1-pyrrolidine, 2-pyrrolidine, 3-pyrrolidine, 4-pyrrolidine, 5-pyrrolidine), pyrazolidine (1-pyrazolidine, 2-pyrazolidine, 3-pyrazolidine, 4-pyrazolidine, 5-pyrazolidine), imidazolidine (1-imidazolidine, 2-imidazolidine, 3-imidazolidine, 4-imidazolidine, 5-imidazolidine), thiazolidine (2-thiazolidine, 3-thiazolidine, 4-thiazolidine, 5-thiazolidine), piperidine (1-piperidine, 2-piperidine, 3-piperidine, 4-piperidine, 5-piperidine, 6-piperidine), piperazine (1-piperazine, 2-piperazine, 3-piperazine, 4-piperazine, 5-piperazine, 6-piperazine), morpholine (2-morpholine, 3-morpholine, 4-morpholine, 5-morpholine, 6-morpholine), thiomorpholine (2-thiomorpholine, 3-thiomorpholine, 4-thiomorpholine, 5-thiomorpholine, 6-thiomorpholine), 1,2-oxathiolane (3-(1,2-oxathiolane), 4-(1,2-oxathiolane), 5-(1,2-oxathiolane), 1,3-dioxolane (2-(1,3-dioxolane), 4-(1,3-dioxolane), 5-(1,3-dioxolane), tetrahydropyrane, (2-tetrahydropyrane, 3-tetrahydropyrane, 4-tetrahydropyrane, 5-tetrahydropyrane, 6-tetrahydropyrane), hexahydropyridazine (1-(hexahydropyridazine), 2-(hexahydropyridazine), 3-(hexahydropyridazine), 4-(hexahydropyridazine), 5-(hexahydropyridazine), 6-(hexahydropyridazine)).

The term "aryl" as used herein includes carbocyclic aromatic ring systems. Aryl is also intended to include the partially hydrogenated derivatives of the carbocyclic systems.

The term "heteroaryl" as used herein includes heterocyclic unsaturated ring systems containing one or more heteroatoms selected from nitrogen, oxygen and sulphur such as furyl, thienyl, pyrrolyl, heteroaryl is also intended to include the partially hydrogenated derivatives of the heterocyclic systems enumerated below.

The terms "aryl" and "heteroaryl" as used herein refers to an aryl which can be optionally substituted or a heteroaryl which can be optionally substituted and includes phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydrobenzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydrobenzo[b]thiophenyl (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl).

The term "halogen" as used herein refers to fluoro, chloro, bromo, and iodo.

The term "aryl-$C_1$–$C_5$ alkyl" as used herein refers to an "aryl" group as defined above attached through an "alkyl" group as defined above having the indicated number of carbon atoms.

The term "heteroaryl-$C_1$–$C_5$ alkyl" as used herein refers to a "heteroaryl" group as defined above attached through an "alkyl" group as defined above having the indicated number of carbon atoms.

The term "$C_3$–$C_7$ cycloalkyl-$C_1$–$C_5$ alkyl" as used herein refers to a "cycloalkyl" group as defined above having the indicated number of carbon atoms attached through an "alkyl" group as defined above having the indicated number of carbon atoms.

The term "$C_3$–$C_7$ cycloheteroalkyl-$C_1$–$C_5$ alkyl" as used herein refers to a "cycloheteroalkyl" group as defined above having the indicated number of carbon atoms attached through an "alkyl" group as defined above having the indicated number of carbon atoms.

DESCRIPTION OF THE INVENTION

The present invention provides compounds of formula I

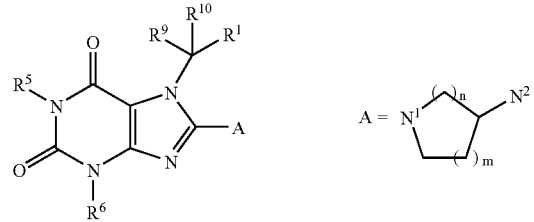

Formula I wherein A may be attached at either $N^1$ or at $N^2$ to the purine system and each n and m is one or two independently $R^1$ is aryl optionally substituted with one or more $R^2$ independently or heteroaryl optionally substituted with one or more $R^2$ independently, $R^2$ is H, $C_1$–$C_7$ alkyl, $C_2$–$C_7$ alkenyl, $C_2$–$C_7$ alkynyl, $C_3$–$C_7$ cycloalkyl, $C_3$–$C_7$cycloheteroalkyl, —$NHCOR^3$, —$NHSO_2R^3$, —$SR^3$, —$SOR^3$, —$SO_2R^3$, —$OCOR^3$, —$CO_2R^4$, —$CON(R^4)_2$, —$CSN(R^4)_2$, —$NHCON(R^4)_2$, —$NHCSN(R^4)_2$, —$NHCONH_2$, —$SO_2N(R^4)_2$, —$OR^4$, cyano, nitro, halogen, wherein each alkyl, alkenyl, alkynyl, cycloalkyl and cycloheteroalkyl is optionally substituted with one or more $R^3$ independently, $R^3$ is Halogen, $C_1$–$C_{10}$ alkyl, $C_2$–$C_{10}$ alkenyl, $C_2$–$C_{10}$ alkynyl, $C_3$–$C_7$ cycloalkyl, aryl, heteroaryl, —$OR^{11}$, —$N(R^{11})_2$, —$SR^{11}$, wherein each alkyl, alkenyl, alkynyl, cycloalkyl, aryl and heteroaryl is substituted with one or more $R^{11}$ independently, $R^4$ is H, $C_1$–$C_{10}$ alkyl, $C_2$–$C_{10}$ alkenyl, $C_2$–$C_{10}$ alkynyl, $C_3$–$C_7$ cycloalkyl, $C_3$–$C_7$ cycloheteroalkyl, aryl, aryl-$C_1$–$C_5$ alkyl, heteroaryl, heteroaryl-$C_1$–$C_5$ alkyl, wherein each alkyl, alkenyl, alkynyl, cycloalkyl, cycloheteroalkyl, aryl, aryl-$C_1$–$C_5$ alkyl, heteroaryl, and heteroaryl-$C_1$–$C_5$ alkyl is substituted with one or more $R^{11}$ independently, $R^5$ is H, $C_1C_{10}$ alkyl, $C_2$–$C_{10}$ alkenyl, $C_2$–$C_{10}$ alkynyl, $C_3$–$C_7$ cycloalkyl, $C_3$–$C_7$ cycloalkyl-$C_1$–$C_5$ alkyl, $C_3$–$C_7$ cycloheteroalkyl, $C_3$–$C_7$ cycloheteroalkyl-$C_1$–$C_5$ alkyl, aryl, heteroaryl, aryl-$C_1$–$C_5$ alkyl, heteroaryl-$C_1$–$C_5$ alkyl, —$OR^7$, —$[(CH_2)_o$—$O]_p$-alkyl, wherein o and p are 1–3independently and wherein each alkyl, alkenyl, alkynyl, cycloalkyl, cycloalkyl-$C_1$–$C_5$ alkyl, cycloheteroalkyl, $C_3$–$C_7$ cycloheteroalkyl-$C_1$–$C_5$ alkyl, aryl, aryl-$C_1$–$C_5$ alkyl, heteroaryl, and heteroaryl-$C_1$–$C_5$ alkyl is optionally substituted with one or more substituents independently selected from $R^7$ or $R^{11}$ independently, $R^6$ is $C_1$–$C_{10}$ alkyl, $C_2$–$C_{10}$ alkenyl, $C_2$–$C_{10}$ alkynyl, $C_3$–$C_7$ cycloalkyl, $C_3$–$C_7$ aryl, heteroaryl, aryl-$C_1$–$C_5$ alkyl, heteroaryl-$C_1$–$C_5$ alkyl, $C_3$–$C_7$ cycloheteroalkyl-$C_1$–$C_5$ alkyl, wherein each alkyl, alkenyl, alkynyl, cycloalkyl, cycloheteroalkyl, $C_3$–$C_7$ cycloheteroalkyl-$C_1$–$C_5$ alkyl, aryl, aryl-$C_1$–$C_5$ alkyl, heteroaryl, aryl-$C_1$–$C_5$ alkyl, and heteroaryl-$C_1$–$C_5$ alkyl is optionally substituted with one or more $R^{11}$ independently, $R^7$ is H, =O, $C_1$–$C_{10}$ alkyl, $C_2$–$C_{10}$ alkenyl, $C_2$–$C_{10}$ alkynyl, $C_3$–$C_7$ cycloalkyl, $C_3$–$C_7$ cycloheteroalkyl, aryl, heteroaryl, —$OR^{11}$, —$N(R^{11})_2$, —$SR^{11}$, wherein each alkyl, alkenyl, alkynyl, cycloalkyl, cycloheteroalkyl, aryl, and heteroaryl is optionally substituted with one or more $R^{11}$ independently, $R^8$ is $C_1$–$C_{10}$ alkyl, $C_2$–$C_{10}$ alkenyl, $C_2$–$C_{10}$ alkynyl, $C_3$–$C_7$ cycloalkyl, $C_3$–$C_7$ cycloheteroalkyl, aryl, heteroaryl, —$OR^{11}$, —$N(R^{11})_2$, —$SR^{11}$, wherein each alkyl, alkenyl, alkynyl, cycloalkyl, cycloheteroalkyl, aryl, and heteroaryl is optionally substituted with one or more $R^{11}$ independently, $R^9$ and $R^{10}$ is independently H, $C_1$–$C_{10}$ alkyl optionally substituted with one or more $R^8$ independently, or halogen, $R^{11}$ is H, —$CF_3$, —$CCl_3$, —$OCF_3$, —OMe, cyano, halogen, —OH, —COMe, —$CONH_2$, —CONHMe, $CONMe_2$, —$NO_2$, $C_1$–$C_{10}$ alkyl, aryl, heteroaryl, $C_3$–$C_7$ cycloalkyl, $C_3$–$C_7$ cycloheteroalkyl, wherein each alkyl, cycloalkyl, cycloheteroalkyl, aryl, and heteroaryl is optionally substituted with one or more $R^{12}$ independently, $R^{12}$ is H, $C_1$–$C_{10}$ alkyl, —$CF_3$, —$CCl_3$, —$OCF_3$, —OMe, cyano, halogen, —OH, —COMe, —$CONH_2$, —CONHMe, —$CONMe_2$, —$NH_2$, —$NO_2$ If $R^9$ and $R^{10}$ is $C_1$–$C_{10}$ alkyl they may be connected to form a cyclopropyl ring, if two $R^4$ or two $R^{11}$ are attached to the same nitrogen they may be connected to form a 3- to 7-membered ring, or any tautomeric form or any optical isomer or mixture of optical isomers, including a racemic mixture, or a salt thereof with a pharmaceutically acceptable acid or base.

In a further embodiment of the invention $R^1$ is aryl optionally substituted with one or more $R^2$ independently.

In a further embodiment of the invention $R^1$ is phenyl substituted with one or more $R^2$ independently.

In a further embodiment of the invention $R^1$ is aryl.

In a further embodiment of the invention $R^1$ is phenyl.

In a further embodiment of the invention $R^2$ is $C_1$–$C_7$ alkyl, $C_2$–$C_7$ alkynyl, cyano, or halogen, wherein each alkyl and alkynyl is optionally substituted with one or more $R^3$ independently.

In a further embodiment of the invention $R^2$ is $C_1$–$C_7$ alkyl, $C_2$–$C_7$ alkynyl, cyano, or halogen.

In a further embodiment of the invention $R^2$ is methyl.

In a further embodiment of the invention $R^2$ is cyano or halogen.

In a further embodiment of the invention $R^3$ is $C_1$–$C_{10}$ alkyl or aryl, wherein each alkyl or aryl is substituted with one or more $R^{11}$ independently.

In a further embodiment of the invention $R^3$ is $C_1$–$C_{10}$ alkyl or aryl.

In a further embodiment of the invention $R^3$ is methyl or phenyl.

In a further embodiment of the invention $R^4$ is H, $C_1$–$C_{10}$ alkyl or aryl, wherein each alkyl or aryl is substituted with one or more $R^{11}$ independently.

In a further embodiment of the invention $R^4$ is H, $C_1$–$C_{10}$ alkyl or aryl.

In a further embodiment of the invention $R^4$ is H, methyl or phenyl.

In a further embodiment of the invention $R^5$ is H, $C_1$–$C_{10}$ alkyl, aryl-$C_1$–$C_5$ alkyl, or heteroaryl-$C_1$–$C_5$ alkyl, wherein each alkyl, aryl-$C_1$–$C_5$ alkyl and heteroaryl-$C_1$–$C_5$ alkyl is optionally substituted with one or more $R^7$ independently.

In a further embodiment of the invention $R^5$ is H or $C_1$–$C_{10}$ alkyl optionally substituted with one or more $R^7$ independently.

In a further embodiment of the invention $R^5$ is H or $C_1$–$C_{10}$ alkyl.

In a further embodiment of the invention $R^5$ is H.

In a further embodiment of the invention $R^5$ is methyl.

In a further embodiment of the invention $R^6$ is $C_1$–$C_{10}$ alkyl, aryl-$C_1$–$C_5$ alkyl, or heteroaryl-$C_1$–$C_5$ alkyl, wherein each alkyl, aryl-$C_1$–$C_5$ alkyl and heteroaryl-$C_1$–$C_5$ alkyl is optionally substituted with one or more $R^{11}$ independently.

In a further embodiment of the invention $R^6$ is $C_1$–$C_{10}$ alkyl, aryl-$C_1$–$C_5$ alkyl, or heteroaryl-$C_1$–$C_5$ alkyl.

In a further embodiment of the invention $R^6$ is $C_1$–$C_{10}$ alkyl optionally substituted with one or more $R^{11}$ independently.

In a further embodiment of the invention $R^6$ is $C_1$–$C_{10}$ alkyl.

In a further embodiment of the invention $R^6$ is methyl.

In a further embodiment of the invention $R^7$ is H, =O, aryl, heteroaryl, $OR^{11}$, $N(R^{11})_2$, $SR^{11}$, wherein each aryl and heteroaryl is optionally substituted with one or more $R^{11}$ independently.

In a further embodiment of the invention $R^7$ is H, =O, aryl, or heteroaryl.

In a further embodiment of the invention $R^7$ is H, =O, $OR^{11}$, $N(R^{11})_2$, or $SR^{11}$.

In a further embodiment of the invention $R^7$ is H or =O.

In a further embodiment of the invention $R^8$ is aryl or heteroaryl, wherein each aryl and heteroaryl is optionally substituted with one or more $R^{11}$ independently.

In a further embodiment of the invention $R^8$ is aryl or heteroaryl.

In a further embodiment of the invention $R^8$ is phenyl.

In a further embodiment of the invention $R^9$ is H, $C_1$–$C_{10}$ alkyl, or halogen.

In a further embodiment of the invention $R^9$ is H.

In a further embodiment of the invention $R^{10}$ is H, $C_1$–$C_{10}$ alkyl, or halogen.

In a further embodiment of the invention $R^{10}$ is H.

In a further embodiment of the invention $R^{11}$ is H, —$CF_3$, cyano, halogen, —OH, —$NO_2$, $C_1$–$C_{10}$ alkyl, aryl, heteroaryl, $C_3$–$C_7$ cycloalkyl, $C_3$–$C_7$ cycloheteroalkyl, wherein each alkyl, cycloalkyl, cycloheteroalkyl, aryl, and heteroaryl is optionally substituted with one or more $R^{12}$ independently.

In a further embodiment of the invention $R^{11}$ is H, halogen, —OH, $C_1$–$C_{10}$ alkyl, aryl, heteroaryl, $C_3$–$C_7$ cycloalkyl, $C_3$–$C_7$ cycloheteroalkyl, wherein each alkyl, cycloalkyl, cycloheteroalkyl, aryl, and heteroaryl is optionally substituted with one or more $R^{12}$ independently.

In a further embodiment of the invention $R^{11}$ is H, halogen, —$CH_3$, aryl, heteroaryl, $C_3$–$C_7$ cycloalkyl, $C_3$–$C_7$ cycloheteroalkyl, wherein each alkyl, cycloalkyl, cycloheteroalkyl, aryl, and heteroaryl is optionally substituted with one or more $R^{12}$ independently.

In a further embodiment of the invention $R^{11}$ is H, halogen, —$CH_3$, heteroaryl, $C_3$–$C_7$ cycloalkyl, $C_3$–$C_7$ cycloheteroalkyl, wherein each alkyl, cycloalkyl, cycloheteroalkyl, and heteroaryl is optionally substituted with one or more $R^{12}$ independently.

In a further embodiment of the invention $R^{11}$ is H, halogen, or —$CH_3$.

In a further embodiment of the invention $R^{11}$ is heteroaryl, $C_3$–$C_7$ cycloalkyl, $C_3$–$C_7$ cycloheteroalkyl, wherein each cycloalkyl, cycloheteroalkyl, and heteroaryl is optionally substituted with one or more $R^{12}$ independently.

In a further embodiment of the invention $R^{11}$ is selected from the group consisting of pyridine, cyclopentane, cyclohexane, and pyrrolidine, wherein each cycloalkyl, cycloheteroalkyl, and heteroaryl is optionally substituted with one or more $R^{12}$ independently In a further embodiment of the invention $R^{12}$ is H, $C_1$–$C_{10}$ alkyl, —$CF_3$, cyano, halogen, —OH, —COMe, —$NH_2$, —$NO_2$.

In a further embodiment of the invention $R^{12}$ is H, —$CF_3$, cyano, halogen, —OH, —$NH_2$.

In a further embodiment of the invention $R^{12}$ is —OH or —$NH_2$.

In a further embodiment of the invention n is two.

In a further embodiment of the invention n is one.

In a further embodiment of the invention m is two or three.

In a further embodiment of the invention m is two.

In a further embodiment of the invention m is three.

The following compounds are preferred:

2-(8-(3-Aminopiperidin-1-yl)-1,3-dimethyl-2,6-dioxo-1,2,3,6-tetrahydropurin-7-ylmethyl)benzonitrile. TFA 8-(3-Aminopyrrolidin-1-yl)-7-benzyl-1,3-dimethyl-3,7-dihydropurine-2,6-dione. HCl (S) 8-(3-Aminopyrrolidin-1-yl)-7-benzyl-1,3-dimethyl-3,7-dihydropurine-2,6-dione. HCl 2-(8-(3-Aminopyrrolidin-1-yl)-1,3-dimethyl-2,6-dioxo-1,2,3,6-tetrahydropurin-7-ylmethyl)benzonitrile. HCl 8-(3-Aminopyrrolidin-1-yl)-7-(2-iodobenzyl)-1,3-dimethyl-3,7-dihydropurine-2,6-dione. HCl 8-(3-Aminoazepan-1-yl)-7-benzyl-1,3-dimethyl-3,7-dihydropurine-2,6-dione. TFA (S) 8-(3-Aminopyrrolidin-1-yl)-7-(2-iodobenzyl)-1,3-dimethyl-3,7-dihydropurine-2,6-dione. H (S) 2-(8-(3-Aminopyrrolidin-1-yl)-1,3-dimethyl-2,6-dioxo-1,2,3,6-tetrahydropurin-7-ylmethyl)benzonitrile. HCl 8-(3-Aminopiperidin-1-yl)-7-(2-iodobenzyl)-1,3-dimethyl-3,7-dihydropurine-2,6-dione. TFA 8-(3-Aminopiperidin-1-yl)-7-(2-bromobenzyl)-1,3-dimethyl-3,7-dihydropurine-2,6-dione. TFA (R) 8-(3-Aminopyrrolidin-1-yl)-7-(2-bromobenzyl)-1,3-dimethyl-3,7-dihydropurine-2,6-dione. TFA (S) 8-(3-Aminopyrrolidin-1-yl)-7-(2-bromobenzyl)-1,3-dimethyl-3,7-dihydropurine-2,6-dione. HCl (R) 8-(3-Aminopyrrolidin-1-yl)-7-benzyl-1,3-dimethyl-3,7-dihydropurine-2,6-dione. HCl (R) 2-(8-(3-Aminopyrrolidin-1-yl)-1,3-dimethyl-2,6-dioxo-1,2,3,6-tetrahydropurin-7-ylmethyl)benzonitrile. HCl (R) 8-(3-Aminopyrrolidin-1-yl)-7-(2-iodobenzyl)-1,3-dimethyl-3,7-dihydropurine-2,6-dione. Hcl (R) 2-[8-(3-Aminopiperidin-1-yl)-1,3-dimethyl-2,6-dioxo-1,2,3,6-tetrahydropurin-7-ylmethyl]-benzonitrile. HCl (R) 8-(3-Aminopiperidin-1-yl)-7-benzyl-1,3-dimethyl-3,7-dihydropurine-2,6-dione. HCl (R) 8-(3-Aminopiperidin-1-yl)-1,3-dimethyl-7-(2-methylbenzyl)-3,7-dihydropurine-2,6-dione. HCl (R) 8-(3-Aminopiperidin-1-yl)-7-(2-chlorobenzyl)-1,3-dimethyl-3,7-dihydropurine-2,6-dione. HCl
(R) 8-(3-Aminopiperidin-1-yl)-7-(2-bromobenzyl)-1,3-dimethyl-3,7-dihydropurine-2,6-dione. HCl
(R) 8-(3-Aminopiperidin-1-yl)-7-(2-bromobenzyl)-3-methyl-1-(2-oxo-2-phenylethyl)-3,7-dihydro-purine-2,6-dione. TFA
(R) 8-(3-Aminopiperidin-1-yl)-7-(2-bromobenzyl)-3-methyl-1-phenethyl-3,7-dihydropurine-2,6-dione. TFA
(R) 8-(3-Aminopiperidin-1-yl)-7-(2-chlorobenzyl)-3-methyl-1-phenethyl-3,7-dihydropurine-2,6-dione. TFA
(R) 2-[8-(3-Aminopiperidin-1-yl)-7-(2-chlorobenzyl)-3-methyl-2,6-dioxo-1,2,3,6-tetrahydropurin-1-ylmethyl]benzonitrile
2-[8-(3-Aminopiperidin-1-yl)-7-(2-cyanobenzyl)-3-methyl-2,6-dioxo-1,2,3,6-tetrahydropurin-1-ylmethyl]benzonitrile
(R) 2-[8-(3-Aminopiperidin-1-yl)-7-(2-cyanobenzyl)-3-methyl-2,6-dioxo-1,2,3,6-tetrahydropurin-1-ylmethyl]benzonitrile. TFA
(R) 2-[8-(3-(R)-Aminopiperidin-1-yl)-3-methyl-2,6-dioxo-1,2,3,6-tetrahydropurin-7-ylmethyl]benzonitrile. HCl
(R) 8-(3-Aminopiperidin-1-yl)-7-(2-chlorobenzyl)-3-methyl-3,7-dihydropurine-2,6-dione. HCl
(R) 8-(3-Aminopiperidin-1-yl)-7-(2-bromobenzyl)-3-methyl-1-(2-oxo-2-thiophen-3-yl-ethyl)-3,7-dihydropurine-2,6-dione. HCl
(R) 2-[8-(3-Aminopiperidin-1-yl)-3-methyl-2,6-dioxo-1-(2-oxo-2-thiophen-3-yl-ethyl)-1,2,3,6-tetrahydropurin-7-ylmethyl]benzonitrile. TFA
8-(3-Amino-piperidin-1-yl)-3-benzyl-7-(3-fluoro-benzyl)-3,7-dihydro-purine-2,6-dione
8-(3-Amino-piperidin-1-yl)-3-benzyl-7-(2-chloro-benzyl)-3,7-dihydro-purine-2,6-dione
8-(3-Amino-piperidin-1-yl)-3-benzyl-7-(2-bromo-benzyl)-3,7-dihydro-purine-2,6-dione
8-(3-Amino-piperidin-1-yl)-3-benzyl-7-(2-methyl-benzyl)-3,7-dihydro-purine-2,6-dione
8-(3-Amino-piperidin-1-yl)-3,7-dibenzyl-3,7-dihydro-purine-2,6-dione
8-(3-Amino-piperidin-1-yl)-3-benzyl-7-(3,5-difluoro-benzyl)-3,7-dihydro-purine-2,6-dione
8-(3-Amino-piperidin-1-yl)-3-benzyl-7-(2,5-difluoro-benzyl)-3,7-dihydro-purine-2,6-dione
8-(3-Amino-piperidin-1-yl)-3-benzyl-7-(2-difluoromethoxy-benzyl)-3,7-dihydro-purine-2,6-dione
8-(3-Amino-piperidin-1-yl)-7-(3-fluoro-benzyl)-3-methyl-3,7-dihydro-purine-2,6-dione
8-(3-Amino-piperidin-1-yl)-7-(2-chloro-benzyl)-3-methyl-3,7-dihydro-purine-2,6-dione
8-(3-Amino-piperidin-1-yl)-3-methyl-7-(2-methyl-benzyl)-3,7-dihydro-purine-2,6-dione
8-(3-Amino-piperidin-1-yl)-7-benzyl-3-methyl-3,7-dihydro-purine-2,6-dione
8-(3-Amino-piperidin-1-yl)-7-(3,5-difluoro-benzyl)-3-methyl-3,7-dihydro-purine-2,6-dione
8-(3-Amino-piperidin-1-yl)-7-(3-fluoro-benzyl)-1,3-dimethyl-3,7-dihydro-purine-2,6-dione
8-(3-Amino-piperidin-1-yl)-1,3-dimethyl-7-(2-methyl-benzyl)-3,7-dihydro-purine-2,6-dione
8-(3-Amino-piperidin-1-yl)-7-(3,5-difluoro-benzyl)-1,3-dimethyl-3,7-dihydro-purine-2,6-dione
8-(3-Amino-piperidin-1-yl)-7-(2,5-difluoro-benzyl)-1,3-dimethyl-3,7-dihydro-purine-2,6-dione
8-(3-Amino-piperidin-1-yl)-7-(2-difluoromethoxy-benzyl)-1,3-dimethyl-3,7-dihydro-purine-2,6-dione
8-(3-Amino-piperidin-1-yl)-7-(2-chloro-benzyl)-3-methyl-1-(2-oxo-2-phenyl-ethyl)-3,7-dihydro-purine-2,6-dione
8-(R-3-Amino-piperidin-1-yl)-7-(2-chloro-benzyl)-3-methyl-1-(2-oxo-2-phenyl-ethyl)-3,7-dihydro-purine-2,6-dione
2-[8-(3-Aminopiperidin-1-yl)-7-(2-bromobenzyl)-3-methyl-2,6-dioxo-1,2,3,6-tetrahydropurin-1-ylmethyl]benzonitrile
8-(3-Amino-piperidin-1-yl)-7-(2-bromo-benzyl)-3-methyl-1-(2-oxo-2-phenyl-ethyl)-3,7-dihydro-purine-2,6-dione
8-(3-Amino-piperidin-1-yl)-3-methyl-1-(2-oxo-2-phenyl-ethyl)-7-(2-trifluoromethyl-benzyl)3,7-dihydro-purine-2,6-dione
8-(3-Amino-piperidin-1-yl)-1-(2-benzo[b]thiophen-3-yl-2-oxo-ethyl)-7-(2-chloro-benzyl)3-methyl-3,7-dihydro-purine-2,6-dione
8-(3-Amino-piperidin-1-yl)-7-(2-chloro-benzyl)-1-[2-(3-fluoro-phenyl)-2-oxo-ethyl]-3-methyl-3,7-dihydro-purine-2,6-dione
8-(3-Amino-piperidin-1-yl)-7-(2-bromo-benzyl)-1-(2-cyclopropyl-2-oxo-ethyl)-3-methyl-3,7-dihydro-purine-2,6-dione
8-(3-Amino-piperidin-1-yl)-7-(2-bromo-benzyl)-1-[2-(2,6-dimethoxy-phenyl)-2-oxo-ethyl]-3-methyl-3,7-dihydro-purine-2,6-dione
8-(3-Amino-piperidin-1-yl)-7-(2-bromo-benzyl)-3-methyl-1-(2-oxo-2-thiophen-3-yl-ethyl)-3,7-dihydro-purine-2,6-dione
8-(3-Amino-piperidin-1-yl)-7-(2-bromo-benzyl)-1-[2-(4-chloro-phenyl)-2-oxo-ethyl]-3-methyl-3,7-dihydro-purine-2,6-dione
8-(3-Amino-piperidin-1-yl)-7-(2-bromo-benzyl)-3-methyl-1-(2-oxo-2-p-tolyl-ethyl)-3,7-dihydro-purin-2,6-dione
8-(3-Amino-piperidin-1-yl)-7-(2-bromo-benzyl)-1-[2-(2-chloro-phenyl)-2-oxo-ethyl]3-methyl-3,7-dihydro-purine-2,6-dione
8-(3-Amino-piperidin-1-yl)-7-(2-bromo-benzyl)-1-[2-(3-methoxy-phenyl)-2-oxo-ethyl]-3-methyl-3,7-dihydro-purine-2,6-dione
8-(3-Amino-piperidin-1-yl)-7-(2-bromo-benzyl)-1-[2-(2-methoxy-phenyl)-2-oxo-ethyl]-3-methyl-3,7-dihydro-purine-2,6-dione
8-(3-Amino-piperidin-1-yl)-7-(2-bromo-benzyl)-3-methyl-1-(2-oxo-butyl)-3,7-dihydro-purine-2,6-dione
8-(3-Amino-piperidin-1-yl)-7-(2-bromo-benzyl)-3-methyl-1-(2-oxo-1-phenyl-pyrrolidin-3-yl)-3,7-dihydro-purine-2,6-dione
8-(3-Amino-piperidin-1-yl)-7-(2-bromo-benzyl)-1-[2-(3-chloro-phenyl)-2-oxo-ethyl]-3-methyl-3,7-dihydro-purine-2,6-dione
2-{8-(3-Amino-piperidin-1-yl)-1-[2-(2,6-difluoro-phenyl)-2-oxo-ethyl]-3-methyl-2,6-dioxo-1,2,3,6-tetrahydro-purin-7-ylmethyl}-benzonitrile
2-[8-(3-Amino-piperidin-1-yl)-3-methyl-2,6-dioxo-1-(2-oxo-2-thiophen-3-yl-ethyl)-1,2,3,6-tetrahydro-purin-7-ylmethyl]-benzonitrile
2-[8-(3-Amino-piperidin-1-yl)-1-(2-benzo[b]thiophen-3-yl-2-oxo-ethyl)-3-methyl-2,6-dioxo-1,2,3,6-tetrahydro-purin-7-ylmethyl]-benzonitrile
2-[8-(3-Amino-piperidin-1-yl)-3-methyl-2,6-dioxo-1-(2-oxo-2-phenyl-ethyl)-1,2,3,6-tetrahydro-purin-7-ylmethyl]-benzonitrile
2-{8-(3-Amino-piperidin-1-yl)-1-[2-(3-fluoro-phenyl)-2-oxo-ethyl]-3-methyl-2,6-dioxo-1,2,3,6-tetrahydro-purin-7-ylmethyl}-benzonitrile 8-(3-Amino-piperidin-1-yl)-3-methyl-1-(2-oxo-2-phenyl-ethyl)-7-(3-trifluoromethoxy-benzyl)-3,7-dihydro-purine-2,6-dione 8-(3-Amino-piperidin-1-yl)-7-(2-fluoro-6-trifluoromethyl-benzyl)-3-methyl-1-(2-oxo-2-phenyl-ethyl)3,7-dihydro-purine-2,6-dione 8-(3-Amino-piperidin-1-yl)-7-(2-fluoro-5-trifluoromethyl-benzyl)-3-methyl-1-(2-oxo-2-phenyl-ethyl)-3,7-dihydro-purine-2,6-dione 2-(8-(3-Aminoazepan-1-yl)-7-(2-chlorobenzyl)-3-methyl-2,6-dioxo-1,2,3,6-tetrahydropurin-1-ylmethyl)benzonitrile. TFA 8-(3-Aminoazepan-1-yl)-7-(2-chlorobenzyl)-3-methyl-3,7-dihydropurine-2,6-dione. TFA 8-(3-Aminoazepan-1-yl)-7-benzyl-3-methyl-1-(2-oxo-2-phenylethyl)-3,7-dihydropurine-2,6-dione. TFA 8-(3-Aminoazepan-1-yl)-7-benzyl-3-methyl-3,7-dihydropurine-2,6-dione. TFA 2-(8-(3-Aminoazepan-1-yl)-3-methyl-2,6-dioxo-1,2,3,6-tetrahydropurin-7-ylmethyl)benzonitrile. TFA 8-(3-Aminoazepan-1-yl)-7-(2-bromobenzyl)-3-methyl-3,7-dihydropurine-2,6-dione. TFA 8-(3-Aminoazepan-1-yl)-3-methyl-7-(2-trifluoromethylbenzyl)-3,7-dihydropurine-2,6-dione. TFA 8-(3-Aminoazepan-1-yl)-3-methyl-7-(2-methylbenzyl)-3,7-dihydropurine-2,6-dione. TFA 8-(3-Aminoazepan-1-yl)-7-(2-bromobenzyl)-1,3-dimethyl-3,7-dihydropurine-2,6-dione. TFA 2-[8-(3-Aminoazepan-1-yl)-1,3-dimethyl-2,6-dioxo-1,2,3,6-tetrahydropurin-7-ylmethyl]benzonitrile. TFA 8-(3-Aminoazepan-1-yl)-1,3-dimethyl-7-(2-methylbenzyl)-3,7-dihydropurine-2,6-dione. TFA 8-(3-Amino-azepan-1-yl)-7-(2-chloro-benzyl)-1,3-dimethyl-3,7-dihydro-purine-2,6-dione, TFA (R) 2-[8-(3-Amino-piperidin-1-yl)-7-(2-chloro-benzyl)-3-methyl-2,6-dioxo-2,3,6,7-tetrahydro-purin-1-yl]-N-pyridin-2-yl-acetamide (R) 2-[8-(3-Amino-piperidin-1-yl)-7-(2-chloro-benzyl)-3-methyl-2,6-dioxo-2,3,6,7-tetrahydro-purin-1-yl]-N-cyclohexyl-acetamide (R) 8-(3-Amino-piperidin-1-yl)-7-(2-chloro-benzyl)-3-methyl-1-(2-oxo-2-pyrrolidin-1-yl-ethyl)-3,7-dihydro-purine-2,6-dione (R) 2-[8-(3-Aminopiperidin-1-yl)-7-(2-chlorobenzyl)-3-methyl-2,6-dioxo-2,3,6,7-tetrahydro-purin-1-yl]-N-cyclopentylacetamide. TFA 2-[8-(3-(R) Amino-piperidin-1-yl)-7-(2-chloro-benzyl)-3-methyl-2,6-dioxo-2,3,6,7-tetrahydro-purin-1-yl]-N-(1-aza-bicyclo[2.2.2]oct-3-yl)-acetamide (R) 2-[8-(3-Amino-piperidin-1-yl)-7-(2-chloro-benzyl)-3-methyl-2,6-dioxo-2,3,6,7-tetrahydro-purin-1-yl]-N-(3-hydroxy-pyridin-2-yl)-acetamide (R,R) 8-(3-Amino-piperidin-1-yl)-7-(2-chloro-benzyl)-1-[2-(3-hydroxy-pyrrolidin-1-yl)-2oxo-ethyl]-3-methyl-3,7-dihydro-purine-2,6-dione (R) 2-[8-(3-Amino-piperidin-1-yl)-7-benzyl-3-methyl-2,6-dioxo-2,3,6,7-tetrahydro-purin-1-yl]-N-pyridin-2-yl-acetamide (R) 2-[8-(3-Amino-piperidin-1-yl)-7-benzyl-3-methyl-2,6-dioxo-2, 3,6,7-tetrahydro-purin-1-yl]-N-cyclohexyl-acetamide (R) 2-[8-(3-Amino-piperidin-1-yl)-7-benzyl-3-methyl-2,6-dioxo-2,3,6,7-tetrahydro-purin-1-yl]-N-cyclopentyl-acetamide 2-[8-(3-(R)-Amino-piperidin-1-yl)-7-benzyl-3-methyl-2,6-dioxo-2,3,6,7-tetrahydro-purin-1-yl]-N-(1-aza-bicyclo[2.2.2]oct-3-yl)-acetamide (R) 2-[8-(3-Amino-piperidin-1-yl)-7-benzyl-3-methyl-2,6-dioxo-2,3,6,7-tetrahydro-purin-1-yl]-N-(3-hydroxy-pyridin-2-yl)-acetamide (R) 2-[8-(3-Amino-piperidin-1-yl)-7-benzyl-3-methyl-2,6-dioxo-2,3,6,7-tetrahydro-purin-1-yl]-N-pyridin-3-yl-acetamide (R) 2-[8-(3-Amino-piperidin-1-yl)-7-(2-cyano-benzyl)-3-methyl-2,6-dioxo-2,3,6,7-tetrahydro-purin-1-yl]-N-(6-amino-pyridin-2-yl)-acetamide (R) 2-[8-(3-Amino-piperidin-1-yl)-7-(2-cyano-benzyl)-3-methyl-2,6-dioxo-2,3,6,7-tetrahydro-purin-1-yl]-N-pyridin-2-yl-acetamide (R) 2-[8-(3-Amino-piperidin-1-yl)-7-(2-cyano-benzyl)-3-methyl-2,6-dioxo-2,3,6,7-tetrahydro-purin-1-yl]-N-(3-hydroxy-pyridin-2-yl)-acetamide (R) 8-(3-Amino-piperidin-1-yl)-1,3-dimethyl-7-thiophen-2-ylmethyl-3,7-dihydro-purine-2,6-dione The compounds of the present invention may be chiral, and it is intended that any enantiomers, as separated, pure or partially purified enantiomers or racemic mixtures thereof are included within the scope of the invention.

Furthermore, when a double bond or a fully or partially saturated ring system or more than one centre of asymmetry or a bond with restricted rotatability is present in the molecule diastereomers may be formed. It is intended that any diastereomers, as separated, pure or partially purified diastereomers or mixtures thereof are included within the scope of the invention.

Furthermore, some of the compounds of the present invention may exist in different tautomeric forms and it is intended that any tautomeric forms, which the compounds are able to form, are included within the scope of the present invention.

Compounds of formula I may be used for the manufacture of a medicament for treating diseases associated with proteins that are subject to inactivation by DPP-IV.

A further aspect of the invention is the use of a compound of the invention for the manufacture of a medicament for treating a condition that may be regulated or normalised via inhibition of DPP-IV.

Another aspect of the invention is the use of a compound of the invention for the manufacture of a medicament for treatment of metabolic disorders.

Another aspect of the invention is the use of a compound of the invention for the manufacture of a medicament for blood glucose lowering.

Another aspect of the invention is the use of a compound of the invention for the manufacture of a medicament for treatment of Type 2 diabetes Another aspect of the invention is the use of a compound of the invention for the manufacture of a medicament for the treatment of impaired glucose tolerance (IGT).

Another aspect of the invention is the use of a compound of the invention for the manufacture of a medicament for the treatment of impaired fasting glucose (IFG).

Another aspect of the invention is the use of a compound of the invention for the manufacture of a medicament for prevention of hyperglycemia.

Another aspect of the invention is the use of a compound of the invention for the manufacture of a medicament for delaying the progression of impaired glucose tolerance (IGT) to Type 2 diabetes.

Another aspect of the invention is the use of a compound of the invention for the manufacture of a medicament for delaying the progression of non-insulin requiring Type 2 diabetes to insulin requiring Type 2 diabetes.

Another aspect of the invention is the use of a compound of the invention for the manufacture of a medicament for increasing the number and/or the size of beta cells in a mammalian subject.

Another aspect of the invention is the use of a compound of the invention for the manufacture of a medicament for treatment of beta cell degeneration, in particular apoptosis of beta cells.

Another aspect of the invention is the use of a compound of the invention for the manufacture of a medicament for the treatment of disorders of food intake.

Another aspect of the invention is the use of a compound of the invention for the manufacture of a medicament for the treatment of obesity.

Another aspect of the invention is the use of a compound of the invention for the manufacture of a medicament for appetite regulation or induction of satiety.

Another aspect of the invention is the use of a compound of the invention for the manufacture of a medicament for the treatment of dyslipidemia.

Another aspect of the invention is the use of a compound of the invention for the manufacture of a medicament for treatment of functional dyspepsia, in particular irritable bowel syndrome.

A further aspect of the invention is a method for treating the conditions mentioned above by administering to a subject in need thereof an effective amount of a compound of the invention.

The compounds of the present invention may be prepared in the form of pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like. Suitable inorganic acid-addition salts include salts of hydrochloric, hydrobromic, sulphuric and phosphoric acids and the like. Further examples of pharmaceutically acceptable inorganic or organic acid addition salts include the pharmaceutically acceptable salts listed in Journal of Pharmaceutical Science, 66, 2 (1977) that are known to the skilled artisan.

Also intended as pharmaceutically acceptable acid addition salts are the hydrates that the present compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of this invention may form solvates with standard low molecular weight solvents using methods known to the skilled artisan.

It is to be understood that the invention extends to all of the stereo isomeric forms of the claimed compounds, as well as the racemates.

Pharmaceutical Compositions

In another aspect, the present invention includes within its scope pharmaceutical compositions comprising, as an active ingredient, at least one compound of the invention which inhibits the enzymatic activity of DPP-IV or a pharmaceutically acceptable salt or prodrug or hydrate thereof together with a pharmaceutically acceptable carrier or diluent.

Pharmaceutical compositions containing a compound of the invention of the present invention may be prepared by conventional techniques, e.g. as described in *Remington: The Science and Practise of Pharmacy*, 19$^{th}$ Ed., 1995. The compositions may appear in conventional forms, for example capsules, tablets, aerosols, solutions, suspensions or topical applications.

Typical compositions include a compound of the invention which inhibits the enzymatic activity of DPP-IV or a pharmaceutically acceptable basic addition salt or prodrug or hydrate thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatine, lactose, terra alba, sucrose, dextrin, magnesium carbonate, sugar, cyclodextrin, amylose, magnesium stearate, talc, gelatine, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound of the invention which inhibits the enzymatic activity of DPP-IV to the appropriate or desired site of action, such as oral, nasal, pulmonary, buccal, subdermal, intradermal, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of the invention which inhibits the enzymatic activity of DPP-IV, dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 250 mg |
| Colloidal silicon dioxide (Aerosil) ® | 1.5 mg |
| Cellulose, microcryst. (Avicel) ® | 70 mg |
| Modified cellulose gum (Ac-Di-Sol) ® | 7.5 mg |
| Magnesium stearate | Ad. |
| Coating: | |
| HPMC approx. | 9 mg |
| *Mywacett 9–40 T approx. | 0.9 mg |

*Acylated monoglyceride used as plasticizer for film coating.

The compounds of the invention are effective over a wide dosage range. For example, in the treatment of adult humans, dosages from about 0.05 to about 1000 mg, preferably from about 0.1 to about 500 mg, per day may be used. A most preferable dosage is about 0.5 mg to about 250 mg per day. In choosing a regimen for patients it may frequently be necessary to begin with a higher dosage and when the condition is under control to reduce the dosage. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 0.05 to about 1000 mg of active ingredient together with a pharmaceutically acceptable carrier per unit dosage.

Usually, dosage forms suitable for oral, nasal, pulmonal or transdermal administration comprise from about 0.05 mg to about 1000 mg, preferably from about 0.5 mg to about 250 mg of the compounds admixed with a pharmaceutically acceptable carrier or diluent.

The invention also encompasses prodrugs of a compound of the invention which on administration undergo chemical conversion by metabolic processes before becoming active pharmacological substances. In general, such prodrugs will be functional derivatives of a compound af the invention which are readily convertible in vivo into a compound af the invention. Conventional procedures for the selection and preparation of suitable prodrug derivatives are described, for example, in "Design of Prodrugs", ed. H. Bundgaard, Elsevier, 1985.

Combination Treatments

The invention furthermore relates to the use of a compound according to the present invention for the preparation of a medicament for use in the treatment of diabetes in a regimen which additionally comprises treatment with another antidiabetic agent.

In the present context the expression "antidiabetic agent" includes compounds for the treatment and/or prophylaxis of insulin resistance and diseases wherein insulin resistance is the pathophysiological mechanism.

In one embodiment of this invention, the antidiabetic agent is insulin or GLP-1 or any analogue or derivative thereof.

In another embodiment the antidiabetic agent is a hypoglycaemic agent, preferably an oral hypoglycaemic agent.

Oral hypoglycaemic agents are preferably selected from the group consisting of sulfonylureas, non-sulphonylurea insulin secretagogues, biguanides, thiazolidinediones, alpha glucosidase inhibitors, glucagon antagonists, GLP-1 agonists, potassium channel openers, insulin sensitizers, hepatic enzyme inhibitors, glucose uptake modulators, compounds modifying the lipid metabolism, compounds lowering food intake, and agents acting on the ATP-dependent potassium channel of the β-cells.

Among the sulfonylureas, tolbutamide, glibenclamide, glipizide and gliclazide are preferred.

Among the non-sulphonylurea insulin secretagogues, repaglinide and nateglinide are preferred.

Among the biguanides, mefformin is preferred.

Among the thiazolidinediones, troglitazone, rosiglitazone and ciglitazone are preferred.

Among the glucosidase inhibitors, acarbose is preferred.

Among the agents acting on the ATP-dependent potassium channel of the β-cells the following are preferred: glibenclamide, glipizide, gliclazide, repaglinide.

The cyclic amines used in the synthesis of the compounds of the invention are either commercially available, or have been made using published procedures. Racemic 3-aminopiperidine was made from 3-aminopyridine by reduction with $PtO_2$ (Nienburg. Chem. Ber. 70(1937)635). Enantiopure (R)- and (S)-3-aminopiperidine and (R)- and (S)-3-Aminopyrrolidine was made according to Moon, S-H and Lee, S. Synth. Commun. 28(1998)3919.

Pharmacological Methods

Methods for Measuring the Activity of Compounds Which Inhibit the Enzymatic Activity of CD26/DPP-IV Summary Chemical compounds are tested for their ability to inhibit the enzyme activity of purified CD26/DPP-IV. Briefly, the activity of CD26/DPP-IV is measured in vitro by its ability to cleave the synthetic substrate Gly-Pro-p-nitroanilide (Gly-Pro-pNA). Cleavage of Gly-Pro-pNA by DPP-IV liberates the product p-nitroanilide (pNA), whose rate of appearance is directly proportional to the enzyme activity. Inhibition of the enzyme activity by specific enzyme inhibitors slows down the generation of pNA. Stronger interaction between an inhibitor and the enzyme results in a slower rate of generation of pNA. Thus, the degree of inhibition of the rate of accumulation of pNA is a direct measure of the strength of enzyme inhibition. The accumulation of pNA is measured spectrophotometrically. The inhibition constant, Ki, for each compound is determined by incubating fixed amounts of enzyme with several different concentrations of inhibitor and substrate.

Materials:

The following reagents and cells are commercially available:

Porcine CD26/DPP-IV (Sigma D-7052), Gly-Pro-pNA (Sigma G0513).

Assay buffer: 50 mM Tris pH 7.4, 150 mM NaCl, 0,1% Triton X-100.

Gly-Pro-pNA cleavage-assay for CD26:

The activity of purified CD26/DPP-IV is assayed in reactions containing:

70 µl assay buffer
10 µl inhibitor or buffer
10 µl substrate (Gly-Pro-pNA from a 0.1M stock solution in water) or buffer
10 µl enzyme or buffer Reactions containing identical amounts of enzyme, but varying concentrations of inhibitor and substrate, or buffer as control, are set up in parallel in individual wells of a 96-well ELISA plate. The plate is incubated at 25° C. and absorbance is read at 405 nm after 60 min incubation. The inhibitor constants are calculated by non-linear regression hyperbolic fit and the result is expressed as inhibition constant (Ki) in nM.

Diabetes Model

The Zucker Diabetic Fatty (ZDF) rat model can be used to investigate the effects of the compounds of the invention on both the treatment and prevention of diabetes as rats of this sub-strain are initially pre-diabetic although develop severe type 2 diabetes characterised by increased HbA1c levels over a period of 6 weeks. The same strain can be used to predict the clinical efficacy of other anti-diabetic drug types. For example, the model predicts the potency and limited clinical efficacy of thiazolidinedione insulin sensitizers compounds.

EXAMPLES

Preparative HPLC (Method A1)

Column: 1.9×15 cm Waters XTerra RP-18. Buffer: linear gradient 5–95% in 15 min, MeCN, 0.1% TFA, flow rate of 15 ml/min. The pooled fractions are either evaporated to dryness in vacuo, or evaporated in vacuo until the MeCN is removed, and then frozen and freeze dried.

Preparative HPLC (Method A2) D9.1.19

Column: Supelcosil ABZ+Plus, 25 cm×10 mm, 5 µm. Solvent A: 0.1% TFA/Water, solvent B: MeCN. Eluent composition: 5 min. 100% A, linear gradient 0–100% B in 7 min, 100% B in 2 min. Flow rate 5 ml/min. The column is allowed to equilibrate for 4 min in 100% A before the next run.

Preparative HPLC (Method A3) HDemPrep

The LC system consists of a Gilson 321 pump, 235 injector and 215-fraction collector equipped with a Waters Xterra 7.8 mm*100 mm column run with a gradient from 10% aqueous acetonitril with 0.01% TFA to 100% acetonitril with 0.01% TFA over 11 min. Flow rate 10 ml/min. The effluent is split 1:1000 to an Agilent 1100 MSD by a LC Packings ACM 10–50 flow splitter. The MS is equipped with an Agilent fraction collector kit, from which the analogue signal from extracted the target ion, is used for controlling fraction collection.

HPLC-MS (Method B) (Anyone)

Column: Waters Xterra MS C-18×3 mm id. Buffer: Linear gradient 10–100% in 7.5 min, MeCN, 0.01% TFA, flow rate 1.0 ml/min. Detection 210 nm (analog output from diode array detector), MS-detection ionisation mode API-ES, scan 100–1000 amu step 0.1 amu.

HPLC-MS (Method C) (h8)

Column: 0.3 mm×15 cm Waters Symmetry $C_{18}$. Buffer: Linear gradient 5–90% in 15 min, MeCN, 0.05% TFA, flow rate 1 ml/min Analytical Separation of Stereoisomers (Method D)

CCE, Chiral capillary electrophoresis: Conditions: HP 3D Capillary Electrophoresis: 48.5/40 cm, 50 µm HP bubble capillary, Electrolyte: HS-β-CD (Regis) (2% w/v) in 50 mM phosphate buffer pH2.5 (HP), Voltage: −17 kV, Injection: 30 mbar for 5s.

Preparative Separation of Stereoisomers (Method E)

Analytical separations were performed on Hewlett Packard 1090 HPLC equipment with 5 chiral Daicel columns (AD, OD, AS, OJ and Welko-O2, 250×4.6 mm) with a diode array detector. The mobile phases were 2-propanol:heptane mixtures with 0.1% DEA.

Preparative separations were performed with the above-mentioned type of columns (250×20 mm) on a preparative Gilson HPLC set-up. Relevant fractions were collected and evaporated (SpeedVac).

Microwave Assisted Reactions (Method F)

The reactants are mixed in an appropriate solvent in a closed teflon vessel (XP 1500 Plus Vessel set) and heated in a micro wave oven (CEM MARSX microwave instrument. Magnetron frequency: 2455 MHz. Power Output: 1200 Watt.). The reaction mixture is cooled and evaporated in vacuo. Normally solvents like MeOH, EtOH, iPrOH, $H_2O$, DMF and DMSO are used.

Chiral Capillary Electrophoresis (CCE) Analysis of 3-aminopiperidine (Method G)

The chiral analysis of 3-aminopiperidine consists of a derivatisation step prior to chiral analysis using capillary electrophoresis (CE).

Derivatisation, 50 µl 40 mM 3-aminopiperidine solution in water is added to 200 µl 40 mM OPA solution (40 mM OPA in 1:15:185 mercaptaethanol:MeOH:water). The reaction in carried out in the dark within 2 minutes. 50 µl of this reaction mixture is diluted with 950 µl water and analysed directly on the CE instrument.

CE instrumentation and conditions, $HP^{3D}CE$ instrument equipped with a 48.5/40.0 cm bubble cell capillary and detection at 226 nm UV. The injection was 50 mbar in 4.0 seconds. The applied voltage was +19 kV which yielded +60 µA and prior to each injection the capillary was washed with 0.1N NaOH for 1 minute and electrolyte for 1.5 minutes. The electrolyte was 0.5% (w/v) carboxyethyl-β-cyclodextrin (Cyclolab, Hungary) dissolved in 50 mM fosphate buffer pH 7.0. The two enantiomers migrate within 5 minutes of electrophoresis and the identity of specific enantiomers is confirmed by spiking of the racemate.

Preparation of (R) piperidine-3-ylamine

Step A: (R)N-CBz nipecotic acid

R (−) Ethylnipeconate tartaric acid salt (117 g, 382 mmol) was dissolved in 2N NaOH (1200 ml, 2.40 mol) and cooled to 5° C. Z-OSu (100 g, 401 mmol) dissolved in 100 ml THF was added to the chilled reaction. The mixture was allowed to stir at 5° C. for 1 h. and at RT overnight. Approx. 100 ml of solvent was removed by rotary evaporation in vacuo, and the remaining solution was acidified to pH 2–3 with conc. HCl (app. 75 ml). The resulting crystal were isolated by filtration and dried in vacuo overnight.

Yield 86 g (85%)

$^1$H-NMR (dmso-d6, 400 MHz) δ: 12.5 (s broad, 1H), (7.42–7.30 (m, 5H), 5.1 (s, 2H), 4.0 (s, 1H), 3.80 (s, 1H), 3.12 (m, 1H), 2.92 (t, 1H), 2.36 (m, 1H), 1.92 (m, 1H), 1.7–1.48 (m, 2H), 1.48–1.30 (m, 1H). HPLC-MS (Method B): m/z=264 (M+1), $R_t$=3.30 min.

Step B: (R) 3-tert-Butoxycarbonylamino-piperidine-1-carboxylic acid benzyl ester (R)N-CBz nipecotic acid (86 g, 327 mmol) was dissolved in toluene (100 ml) and evaporated to dryness three times. tert. Butanol (1000 ml, 10.5 mmol) and triethylamine (50.1 ml, 359 mmol) were added to the reaction mixture. The reaction mixture was stirred for 30 min., and DPPA (98.5 ml, 457 mmol) was added over 15 min. The reaction mixture was heated to 100° C. overnight. After cooling, the solvent was removed by evaporation in vacuo, and water (200 ml) was added. After overnight stirring at RT the product was isolated by filtration, and stirred with EtOAc (250 ml) for one hour. The EtOAc solution was filtered and evaporated in vacuo to give the crude product as a white solid. This material was dissolved in hot EtOAc (200 ml), and cooled to 5° C. overnight. The precipitated product was isolated by filtration, washed with cold EtOAc and dried.

Yield 50.0 g (46%).

$^1$H-NMR (dmso-d6, 400 MHz) δ: 7.32 (s, 5H), 5.12 (s, 2H), 4.6 (s, 1H), 3.8–3.15 (m, 5H), 1.85 (m, 1H), 1.65 (s, 1H), 1.6–1.35 (m, 11H).

Step C: (R) Piperidin-3-yl-carbamic acid tert.-butyl ester (R) 3-tert-Butoxycarbonylamino-piperidine-1-carboxylic acid benzyl ester (50 g, 150 mmol) was dissolved in abs. EtOH (500 ml), and hydrogenated (1 atm, 7 days, 10% Pd/C (5.0 g)) at RT. The reaction was filtered and evaporated in vacuo to give the product as a white solid Yield 27.3 g (92%).

$^1$H-NMR (dmso-d6, 300 MHz) δ: 6.85 (d, 1H), 3.41 (s br, 2H), 3.05 (m, 1H), 2.90 (m, 1H), 2.58–2.35 (m, 2H), 1.92 (m, 1H), 1.75 (m, 1H), 1.58 (s, 9H), 1.50–1.40 (m, 2H).

For analysis a small sample of the product (50 mg) was dissolved in EtOAc (2 ml), treated with 3 N HCl in EtOAc (2 ml), and evaporated in vacuo. The product was stirred with EtOAc (5 ml) for one hour and filtered to give (R) 3-aminopiperidine in >98% ee, (determined as described in method G).

Preparation of Azepan-3-ylamine

3-Amino-azepan-2-one (24.0 g, 0.188 mol) was dissolved in THF and cooled on an ice bath in a nitrogen atmosphere. LiAlH$_4$ (35.6 g, 0.938 mol) was added in small portions. After the last addition the re-action mixture was allowed to warm up to room temperature and stirred for 72 hours, then refluxed for 48 hours. Water was added very slowly until a white reaction mixture was obtained. K$_2$CO$_3$ was added until a filterable slurry was obtained. Then the reaction mixture was filtered, and the precipitate was washed with THF (3×300 ml). The combined THF phase was evaporated in vacuo giving the title compound as a yellow oil. No further purification was performed.

HPLC-MS: (Method B): m/z=115 (M+1), R t=0.53 min, Purity (UV)=99%.

$^1$H-NMR (MeOD-d$_4$): δ: 4.5 (s, 3H), 2.8–3.0 (m, 4H), 2.45–2.6 (m, 1H), 1.9 (m, 1H), 1.4–1.75 (m, 5H).

$^{13}$C-NMR (MeOD-d$_4$): δ: 57.68, 54.40, 50.19, 38.04, 31.79, 24.01.

| Abbreviations | |
|---|---|
| CBz | Carbobenzoxycarbonyl |
| EtOAc | Ethyl acetate |
| DCM | Dichloromethane |
| DEA | Diethylamine |

| Abbreviations | |
|---|---|
| DIEA | Diisopropylethylamine |
| DMF | Dimethylformamide |
| DMSO | Dimethyl sulfoxide |
| DPPA | Diphenylphosphonic azide |
| HOAc | Acetic acid |
| MeCN | Acetonitrile |
| TFA | Trifluoroacetic acid |
| THF | Tetrahydrofuran |
| TMG | Tetramethylguanidine |

General Procedure (A):

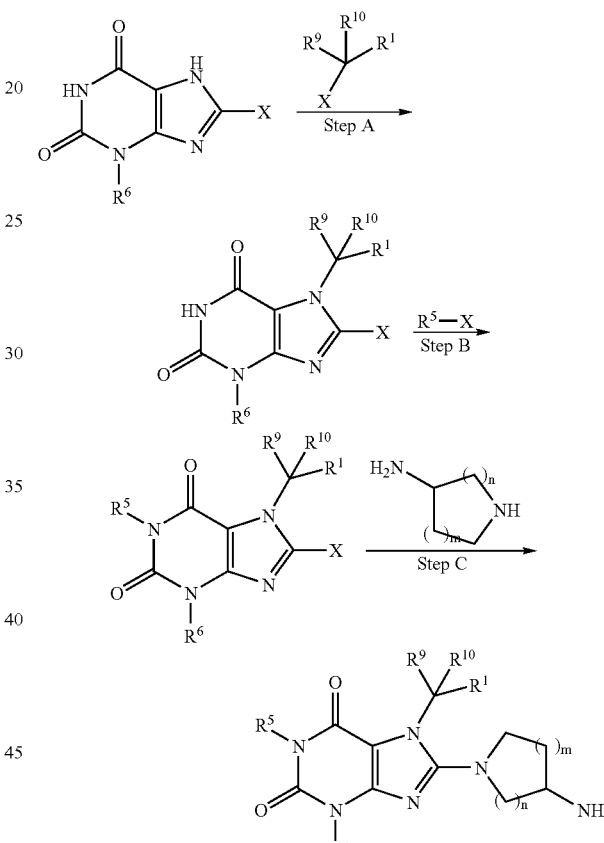

Step A:

The starting material (16 μmol) is dissolved in a mixture of DMF and DIEA (3% DIEA, 250 μl). The alkylation reagent R$^1$—CR$^9$R$^9$—X (16.8 μmol, 1.05 equiv) is dissolved in DMF (100 μl) and added. The mixture is heated to 65° C. for 2 h.

Step B:

Alkylation reagent R$^5$—Br (32 μmol) is dissolved in DMF (100 μl) and added to the reaction mixture followed by a solution of TMG in DMF (1.16 ml TMG diluted to 5.8 ml, 48 μl). The mixture is kept at 65° C. for 4 h.

Step C:

The diamine (200 μmol) is dissolved in a mixture of DMF and DIEA (3% DIEA, 200 μl) and added to the reaction mixture. The reaction is kept at 50° C. for 24 h.

Samples are neutralized using HOAc (20 μl), stripped and purified by HPLC. Samples are dissolved in DMSO/H₂O (4:1, 500 μl).

General Procedure (B)

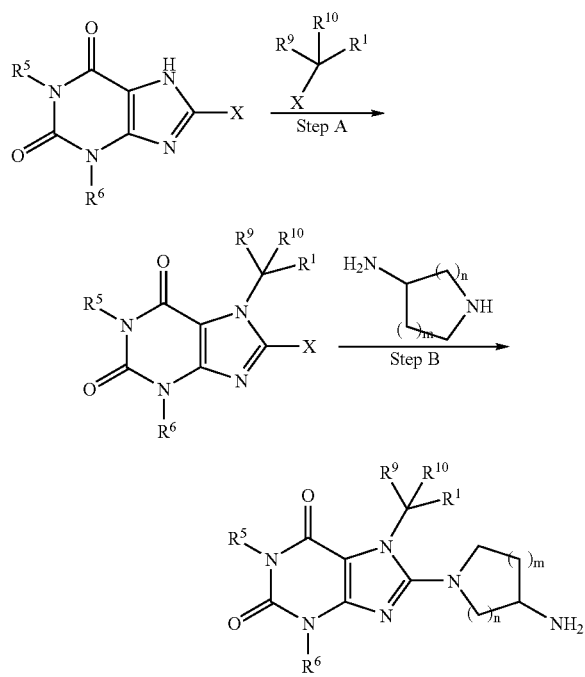

Step A:

The starting material (16 μmol) is dissolved in a mixture of DMF and DIEA (3% DIEA, 250 μl). The alkylation reagent $R^1$—$CR^9R^9$—X (16.8 μmol, 1.05 equiv) is dissolved in DMF (100 μl) and added. The mixture is heated to 65° C. for 2 h.

Step B:

Diamine (200 μmol) is dissolved in a mixture of DMF and DIEA (3% DIEA, 200 μl) and added to the reaction mixture. The reaction is kept at 50° C. for 24–48 h, and then all volatiles are stripped.

Samples are neutralized using HOAc (20 μl), stripped and purified by HPLC methods A1, A2 or A3. Samples are dissolved in DMSO/H₂O (4:1, 500 μl).

General Procedure C

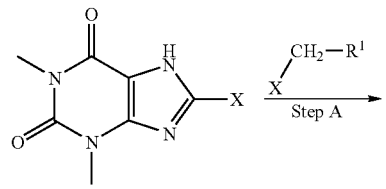

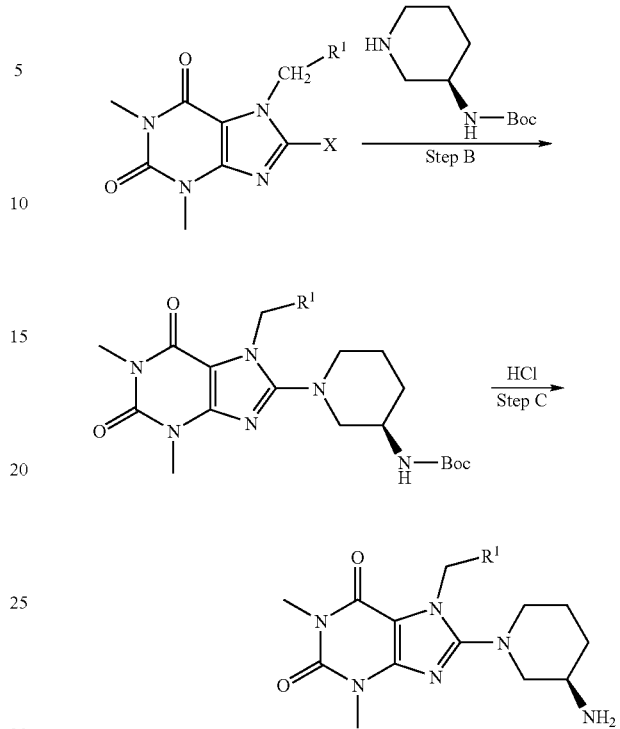

Step A:

8-Chlorotheophylline (1 eq.) and K₂CO₃ (2.2 eq) is slurried in DMF (app. 12 ml/g of 8-Chlorotheophylline). The benzyl chloride (or bromide) is added (1.1 eq), and the slurry is stirred until the reaction is finished (1–7 days) at RT. The reaction mixture is poured into water (app. 70 ml/g 8-Chlorotheophylline) and stirred until the precipitation of the product has completed.

The product is filtered and dried in vacuo.

Step B:

The benzylated 8-Chlorotheophylline (1 eq.) is dissolved in DMSO (app. 35 ml/g), K₂CO₃ (4 eq.) is added, and then (R) Piperidin-3-yl-carbamic acid tert.-butyl ester (2 eq.) is added, and the reaction is stirred at either RT, 50° C., or at 65° C. until finished (usually overnight). The reaction mixture is poured into water (4–10 ml/ml DMSO) with stirring, and the precipitated product is isolated by filtration, and washed with water, and dried.

Step C:

The product from step B (1 eq.) is dissolved in MeCN (app. 20 ml/g), and conc. HCl is added (10 eq.). The reaction is left with stirring overnight, and evaporated in vacuo. The product is dissolved in EtOAc and water (1+1, app. 50 ml/g), separated, and the aqueous phase washed with EtOAc (2×25 ml/g). The aqueous phase is added an equal amount of 2N K₂CO₃, and extracted with EtOAc (3×25 ml/g). The combined EtOAc phase is washed with brine, dried (MgSO₄), and about half the solvent is removed by evaporation in vacuo. Conc. HCl is added (1.1 eq.), and the solvent is evaporated in vacuo. The product is dissolved in hot EtOH, precipitated with Et₂O, collected by filtration, and dried in vacuo.

General Procedure (D):

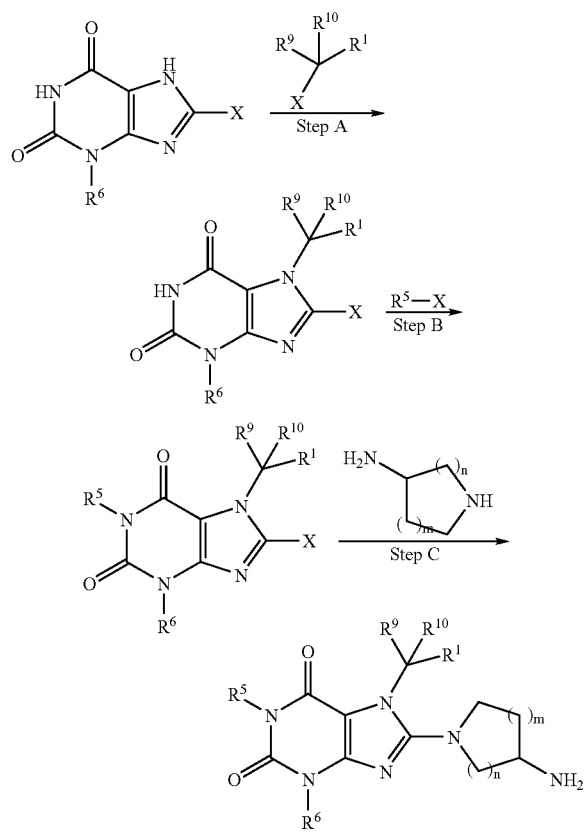

Step A:

The starting material (32 µmol) is dissolved in a mixture of DMF and DIEA (3% DIEA, 500 µl). The alkylation reagent $R^1$—$CR^9R^9$—X (33.6 µmol, 1.05 equiv) is dissolved in DMF (200 µl) and added. The mixture is heated to 65° C. for 2 h. Upon cooling to 25° C., $K_2CO_3$ (aq) is added (5.12M, 50 µL, 256 umol). Volatiles are stripped.

Step B:

Alkylation reagent $R^5$—Br (64 µmol) is dissolved in DMF (250 µl) and added to the reaction mixture. The mixture is kept at 25° C. for 48 h. Volatiles are stripped.

Step C:

The diamine (400 µmol) is dissolved in DMSO and added to the reaction mixture. If the dihydrochloride salt of the diamine is employed, four equivalents of DCHMA is added. The reaction is kept at 50° C. for 48 h.

Samples are neutralized using HOAc (30 µl), and purified by HPLC Method A3.

General Procedure (E):

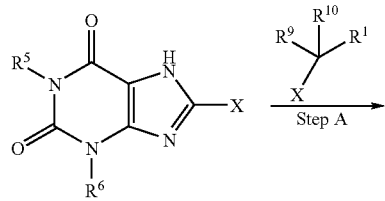

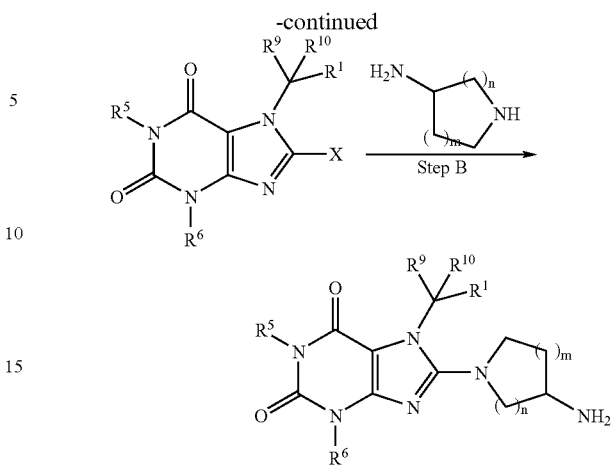

Step A:

The starting material (4.08 mmol) is dissolved in a mixture of DMF and DIEA (3% DIEA, 65 ml). The alkylation reagent $R^1$—$CR^9R^9$—X (4.28 mmol, 1.05 equiv) is dissolved in DMF (25.5 ml) and added. The mixture is heated to 65° C. for 2 h and poured onto ice followed by filtration of the alkylated product.

Step B:

Diamine (400 µmol) is dissolved in DMSO (400 µl) and added to the above product (32 mmol). The reaction is kept at 50° C. for 24–48 h.

Samples are neutralized using HOAc (30 µl) and purified by HPLC Method A1 or HPLC Method A2.

General Procedure (F):

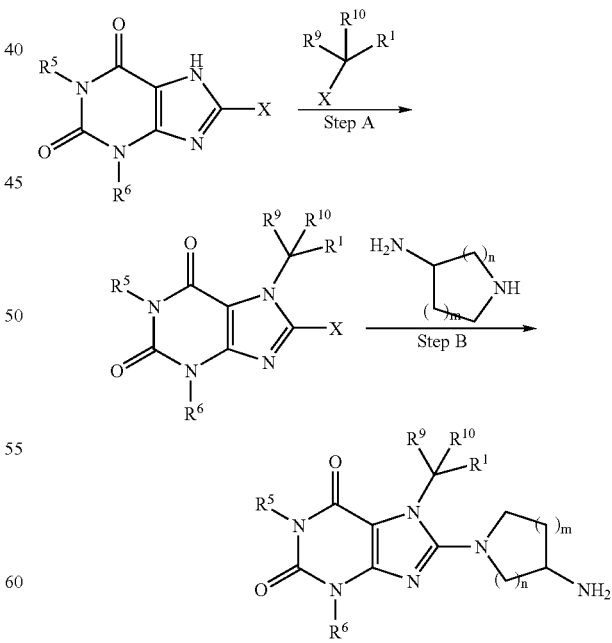

Step A:

The starting material (32 µmol) is dissolved in a mixture of DMF and DIEA (3% DIEA, 500 µl). The alkylation reagent R¹—CR⁹R⁹—X (33.6 μmol, 1.05 equiv) is dissolved in DMF (200 μl) and added. The mixture is heated to 65° C. for 2 h.

Step B:

Diamine (400 μmol) is dissolved in DMSO (400 μl) and added to the above reaction mixture.

The reaction is kept at 50° C. for 48 h.

Samples are neutralized using HOAc (30 μl) and purified by HPLC Method A2 or A3.

General Procedure (G):

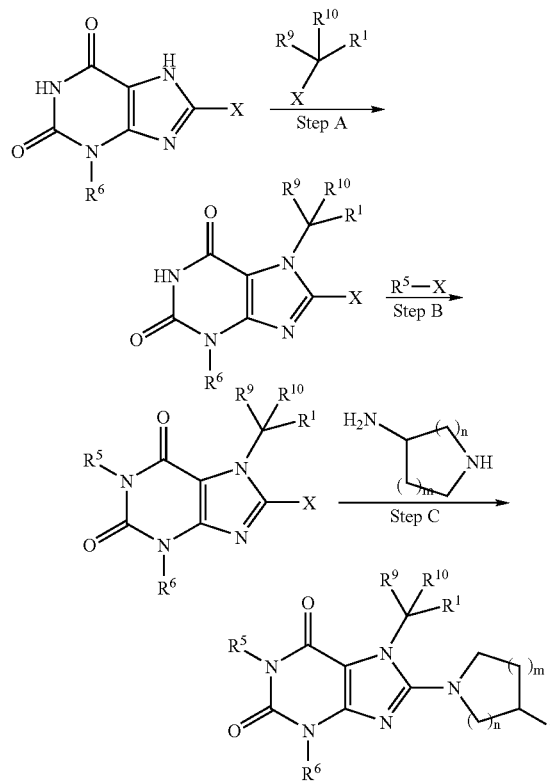

Step A:

The starting material (20.40 mmol) is dissolved in DMF (50 ml) and DIEA (10 ml). The alkylation reagent R¹—CR⁹R⁹—X (22.03 mmol, 1.08 equiv) is dissolved in DMF (10 ml) and added. Heating the mixture to 65° C. for 2 h affords the products that are isolated by filtration upon adding the reaction mixture onto ice (300 ml).

Step B:

The product from Step A (5.56 mmol) and alkylation reagent R⁵—Br (11.11 mmol) are dissolved in DMF (60 ml) and potassium carbonate is added to the reaction mixture. Upon stirring at 25° C. for 16 h the reaction mixture is poured onto ice (300 ml) and the product is isolated by filtration and dried in vacuo.

Step C:

The product from Step B (0.472 mmol) is dissolved in DMSO (5 ml) and the diamine (2.36 mmol) is added to the reaction mixture. If the dihydrochloride salt of the diamine is employed, K₂CO₃ (2.36 mmol) is added. The reaction is kept at 50° C. for 24 h and poured onto ice (20 ml). The product is isolated by filtration. The compounds may be purified by HPLC methods A1, A2 or A3 or by treatment with hot acetonitrile.

General Procedure (H):

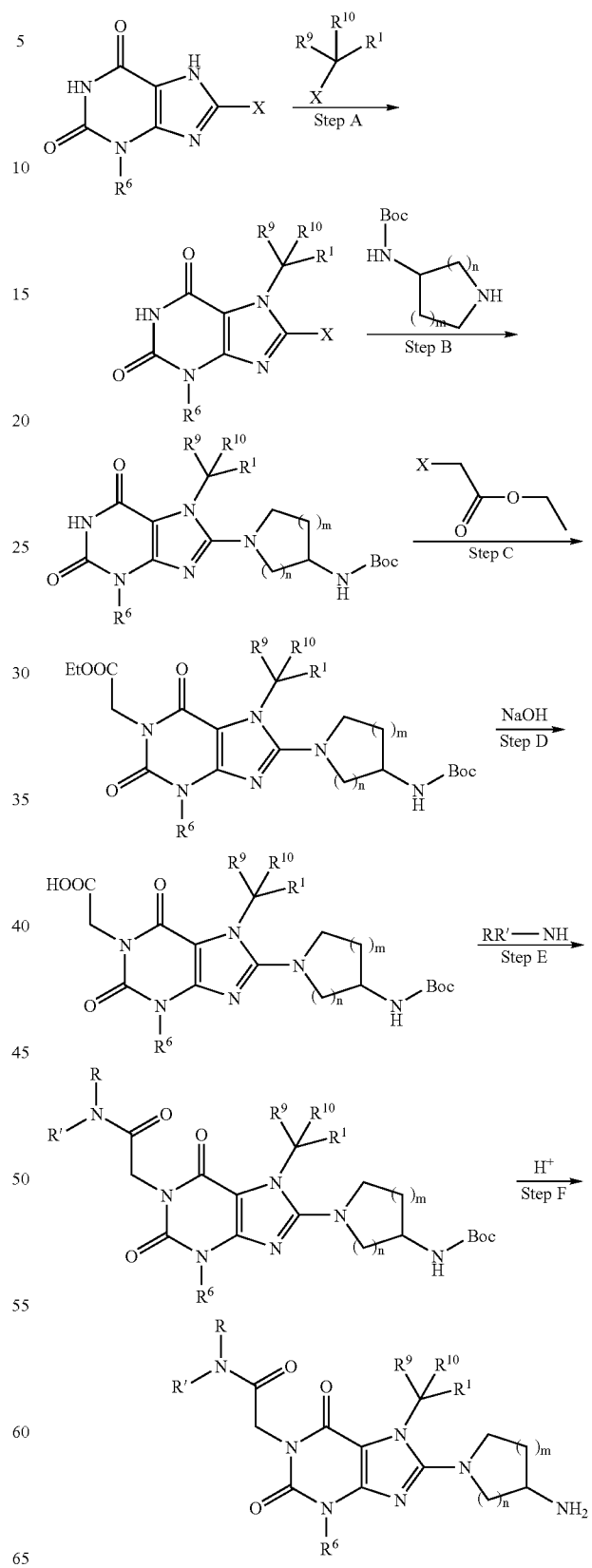

Step A:

The starting material (20.40 mmol) is dissolved in DMF (50 ml) and DIEA (10 ml). The alkylation reagent $R^1$—$CR^9R^9$—X (22.03 mmol, 1.08 equiv) is dissolved in DMF (10 ml) and added. Heating the mixture to 65° C. for 2 h affords the products that are isolated by filtration upon adding the reaction mixture onto ice (300 ml).

Step B:

The product from step A is dissolved in DMSO (app. 40 ml/g), DIEA (2 eq.) is added, and then (R) Piperidin-3-yl-carbamic acid tert.-butyl ester (2 eq.) is added, and the reaction is stirred at either RT, 50° C., or at 65° C. until finished (usually overnight). The reaction mixture is poured into ice/water (4–10 ml/ml DMSO) with stirring, and the precipitated product is isolated by filtration, and washed with water, and dried.

Step C:

The product from step B is dissolved in DMF (1 eq. app. 10 ml/g). Ethyl 2-bromoacetate is added (2 eq.) is added, $K_2CO_3$ (3.5 eq) is further added, and the reaction is left with stirring at RT until completed. The reaction is poured onto ice/water (app. 100 ml), and the precipitated product is isolated by filtration, and washed with water, and dried.

Step D:

The product from step C is dissolved in EtOH (25 ml) with stirring, added 1 N NaOH (6 ml), and left with stirring overnight. HOAc (6 ml) is added, and the solvent is evaporated. The residue is poured onto ice/water (app. 100 ml), and the precipitated product is isolated by filtration, and washed with water, and dried.

Step E:

The product from step D (1 eq. 20 µmol) is dissolved in a solution of Carbonyldiimidazole (1.5 eq. 30 µM) in DMF (250 µl), and left for 2 hours. The amine NRR' (2 eq. 40 µM), dissolved in DMF (50 µl), was added and the reaction left with stirring overnight at RT. Another portion of the amine was added as before, and the reaction left with stirring overnight. The product was isolated by evaporation of the solvent.

Step F:

The product from step E was added TFA in DCM (200 µl 1:1), and the reaction was left for 2 hours. Evaporation of the solvent overnight gave the product, which may be further purified by prep. HPLC methods A1, A2 or A3.

NNC 0072-0000-1085

Example 1

2-(8-(3-Aminopiperidin-1-yl)-1,3-dimethyl-2,6-dioxo-1,2,3,6-tetrahydropurin-7-ylmethyl)benzonitrile

TFA (1)

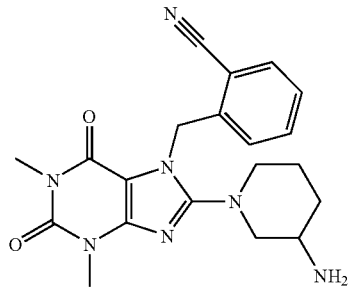

NNC 0072-0000-5060-Step A: 2-(8-Chloro-1,3-dimethyl-2,6-dioxo-1,2,3,6-tetrahydropurin-7-ylmethyl)benzonitrile (1A)

8-Chlorotheophylline (20 g, 93.19 mmol) was dissolved in 800 ml of DMF and 2-cyanobenzyl bromide (18.28 g, 93.19 mmol), potassium carbonate (12.88 g, 93.19 mmol), and potassium iodide (10 mg, 0.06 mmol) were added. The mixture was stirred at room temperature for 20 hours. The solvent was evaporated and the residue was suspended in 900 ml of water and 900 ml of EtOAc, and compound (1A) was collected by filtration of the suspension. The layers in the mother liquor were separated and the aqueous layer was extracted with 3×500 ml of EtOAc. The combined organic layers were washed with 1×500 ml of water, and the solvent was evaporated to give compound (1A) as white crystals.

Combined yield: 28.6 g (93%). Mp. 222.5–223.7° C.

$^1$H-NMR (DMSO, 300 MHz) δ: 3.20 (s, 3H), 3.43 (s, 3H), 5.74 (s, 2H), 7.06 (d, 1H), 7.53 (t, 1H), 7.67 (t, 1H), 7.93 (d, 1H). HPLC-MS (Method B): m/z=330 (M+1), $R_t$=2.93 min.

NNC 0072-0000-1085-Step B: 2-(8-(3-Aminopiperidin-1-yl)-1,3-dimethyl-2,6-dioxo-1,2,3,6-tetrahydropurin-7-ylmethyl)benzonitrile

TFA (1)

2-(8-Chloro-1,3-dimethyl-2,6-dioxo-1,2,3,6-tetrahydropurin-7-ylmethyl)benzonitrile (1A) (100 mg, 0.30 mmol) and 3-aminopiperidine dihydrochloride (262 mg, 1.52 mmol) were dissolved in 20 ml of 2-propanol and triethylamine (0.127 ml, 0.91 mmol) and subjected to microwaves (method F, 130° C., 300 W) for ten hours. The solvents were evaporated and the crude product was purified by preparative HPLC, (method A1, Rt=6.78 min.) to give the title compound as oily crystals.

Yield: 66 mg (43%).

$^1$H-NMR (MeOD, 300 MHz) δ: 1.73 (m, 3H), 2.10 (m, 1H), 3.02 (m, 1H), 3.20 (m, 2H), 3.27 (s, 3H), 3.52 (m, 4H), 3.65 (m, 1H), 5.59 (s, 2H), 7.22 (d, 1H), 7.47 (m, 1H), 7.61 (m, 1H), 7.78 (d, 1H). HPLC-MS (Method B): m/z=394 (M+1), $R_t$=1.55 min.

Example 2

8-(3-Aminopyrrolidin-1-yl)-7-benzyl-1,3-dimethyl-3,7-dihydropurine-2,6-dione HCl (2)

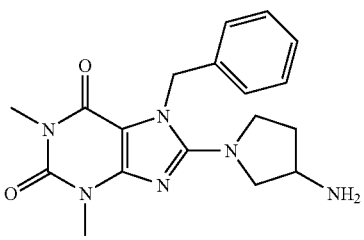

Step A: 7-Benzyl-8-chloro-1,3-dimethyl-3,7-dihydropurine-2,6-dione (2A)

8-Chlorotheophylline (50 g, 0.23 mol) was suspended in 600 ml of DMF and benzyl bromide (31 ml, 0.26 mol) and potassium carbonate (64 g, 0.46 mol) were added. The mixture was stirred at room temperature for 20 hours. The solvent was evaporated and the residue was dissolved in 250 ml of water and 400 ml of DCM. The layers were separated and the aqueous layer was extracted with 150 ml of DCM.

The combined organic layer was washed with 100 ml of brine, dried over magnesium sulphate, filtered, and the solvent was evaporated to give compound (2A) as white crystals.

Yield: 73.6 g (104%). Mp. 152–154° C.

$^1$H-NMR (CDCl$_3$, 200 MHz) δ: 3.42 (s, 3H), 3.55 (s, 3H), 5.55 (s, 2H), 7.35 (m, 5H). HPLC-MS (Method B): m/z=305 (M+1), R$_t$=3.33 min.

Step B: 8-(3-Aminopyrrolidin-1-yl)-7-benzyl-1,3-dimethyl-3,7-dihydropurine-2,6-dione. HCl (2)

7-Benzyl-8-chloro-1,3-dimethyl-3,7-dihydropurine-2,6-dione (2A) (100 mg, 0.33 mmol) and 3-aminopyrrolidine (0.16 ml, 1.64 mmol) were dissolved in 20 ml of 2-propanol and subjected to microwaves (method F, 150° C., 300 W) for one hour. The solvent was evaporated and the crude product was purified by preparative HPLC (method A1, Rt=6.45 min.). Evaporation of the solvent afforded the title compound as a brown oil.

Yield: 111 mg (87%).

$^1$H-NMR (MeOD, 400 MHz) δ: 2.04 (m, 1H), 2.37 (m, 1H), 3.30 (s, 3H), 3.51 (s, 3H), 3.60–3.80 (m, 3H), 3.87–3.95 (m, 2H), 5.54 (d, 1H), 5.64 (d, 1H), 7.14 (d, 2H), 7.23–7.35 (m, 3H) HPLC-MS (Method B): m/z=355 (M+1), R$_t$=1.49 min.

Example 3

(S) 8-(3-Aminopyrrolidin-1-yl)-7-benzyl-1,3-dimethyl-3,7-dihydropurine-2,6-dione HCl (3)

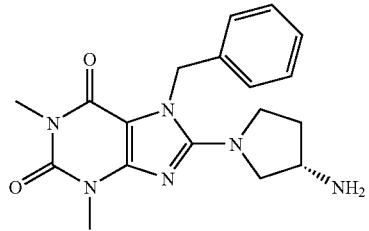

Step A: (S) (1-(7-Benzyl-1,3-dimethyl-2,6-dioxo-1,2,3,6-tetrahydropurin-8-yl)pyrrolidin-3-yl)carbamic acid tert-butyl ester (3A)

7-Benzyl-8-chloro-1,3-dimethyl-3,7-dihydropurine-2,6-dione (2A) (100 mg, 0.33 mmol), (3S)-(−)-3-(tert-butoxycarbonylamino)pyrrolidine (305 mg, 1.64 mmol), and triethylamine (0.46 ml, 3.28 mmol) was dissolved in 20 ml of 2-propanol and 5 ml of DMF and the mixture was subjected to microwaves (method F, 130° C., 300 W) for three hours. The solvent was evaporated and the crude product was purified by preparative HPLC (method A1, Rt=11.75 min.). Evaporation of the solvent afforded compound (3A) as a brown oil.

Yield: 130 mg (87%)

$^1$H-NMR (CDCl$_3$, 200 MHz) δ: 1.42 (s, 9H), 1.89 (m, 1H), 2.12 (m, 1H), 3.34 (s, 3H), 3.37–3.79 (m, 7H), 4.22 (br. s, 1H), 4.97 (d, 1H), 5.49 (d, 1H), 5.55 (d, 1H), 7.04 (m, 2H), 7.28 (m, 3H). HPLC-MS (Method B): m/z=455 (M+1), R$_t$=3.95 min.

Step B: (S) 8-(3-Aminopyrrolidin-1-yl)-7-benzyl-1,3-dimethyl-3,7-dihydropurine-2,6-dione. HCl (3)

(S) (1-(7-Benzyl-1,3-dimethyl-2,6-dioxo-1,2,3,6-tetrahydropurin-8-yl)pyrrolidin-3-yl)carbamic acid tert-butyl ester (3A) (130 mg, 0.29 mmol) was dissolved in 15 ml of diethyl ether, hydrochloric acid in diethyl ether (2.5 M, 5.72 ml, 14.3 mmol) was added, and the mixture was stirred at room temperature for 24 hours. The solvents were evaporated and the crude product was suspended in dry DCM and collected by filtration to afford the title compound as white crystals.

Yield: 101 mg, (91%) Mp. 166–169° C.

$^1$H-NMR (MeOD, 300 MHz) δ: 2.05 (m, 1H), 2.37 (m, 1H), 3.29 (s, 3H), 3.52 (s, 3H), 3.58–3.97 (m, 5H), 5.53 (d, 1H), 5.63 (d, 1H), 7.13 (d, 2H), 7.21–7.36 (m, 3H). HPLC-MS (Method B): m/z=355 (M+1), R$_t$=1.52 min.

Example 4

2-(8-(3-Aminopyrrolidin-1-yl)-1,3-dimethyl-2,6-dioxo-1,2,3,6-tetrahydropurin-7-ylmethyl)benzonitrile HCl (4)

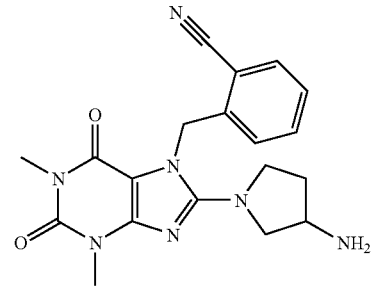

2-(8-Chloro-1,3-dimethyl-2,6-dioxo-1,2,3,6-tetrahydropurin-7-ylmethyl)benzonitrile (1A) (100 mg, 0.30 mmol) and 3-aminopyrrolidine (0.15 ml, 1.52 mmol) were reacted and purified as described in example 2, step B, to give the title compound as a yellow foam.

Yield: 108 mg (76%). Mp.186–189° C.

Prep. HPLC (method A1): R$_t$=6.19 min.

$^1$H-NMR (MeOD, 400 MHz) δ: 2.09 (m, 1H), 2.40 (m, 1H), 3.27 (s, 3H), 3.50 (s, 3H), 3.59–3.78 (m, 3H), 3.88–3.99 (m, 2H), 5.70 (d, 1H), 5.79 (d, 1H), 7.12 (d, 1H), 7.49 (dd, 1H), 7.62 (dd, 1H), 7.80 (d, 1H). HPLC-MS (Method B): m/z=380 (M+1), R$_t$=1.35 min.

Example 5

8-(3-Aminopyrrolidin-1-yl)-7-(2-iodobenzyl)-1,3-dimethyl-3,7-dihydropurine-2,6-dione HCl (5)

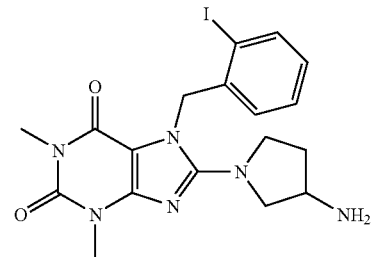

NNC 0072-0000-5069-Step A: 8-Chloro-7-(2-iodobenzyl)-1,3-dimethyl-3,7-dihydropurine-2,6-dione (5A)

8-Chlorotheophylline (8.5 g, 39.6 mmol) was dissolved in 400 ml of DMF and 2-iodobenzyl chloride (10.0 g, 39.6 mmol), potassium carbonate (5.47 g, 39.6 mmol), and potassium iodide (10 mg, 0.06 mmol) were added. The mixture was stirred at room temperature for 7 days. Water (2500 ml) and EtOAc (800 ml) were added and the layers were separated. The aqueous layer was extracted with 2×500 ml of EtOAc, and the combined organic layer was washed with 500 ml of water, 500 ml of brine, dried over sodium sulphate, and filtered. The solvent was evaporated and the crude product was crystallized from diethyl ether and petrol, to give compound (5A) as white crystals. The mother liquor was evaporated and resuspended in diethyl ether and petrol, to give a second crop of compound (5A).

Combined yield: 10.4 g (61%). Mp. 177.6–178.2° C.

$^1$H-NMR (CDCl$_3$, 300 MHz) δ: 3.37 (s, 3H), 3.61 (s, 3H), 5.59 (s, 2H), 6.48 (d, 1H), 7.02 (t, 1H), 7.27 (t, 1H), 7.90 (d, 1H). HPLC-MS (Method B): m/z=431 (M+1), R$_t$=3.94 min.

Step B: 8-(3-Aminopyrrolidin-1-yl)-7-(2-iodobenzyl)-1,3-dimethyl-3,7-dihydropurine-2,6-dione. HCl (5)

8-Chloro-7-(2-iodobenzyl)-1,3-dimethyl-3,7-dihydropurine-2,6-dione (5A) (100 mg, 0.23 mmol) and 3-aminopyrrolidine (0.13 ml, 1.16 mmol) were reacted and purified as described in example 2, step B, to give the crude product, which was further suspended in dry DCM, and filtered to afford the title compound as white crystals.

Yield: 77 mg (64%).

Prep. HPLC (method A1): R$_t$=7.28 min.

$^1$H-NMR (MeOD, 200 MHz) δ: 2.02 (m, 1H), 2.35 (m, 1H), 3.27 (s, 3H), 3.47–3.74 (m, 6H), 3.82–3.93 (m, 2H), 5.44 (d, 1H), 5.53 (d, 1H), 6.72 (d, 1H), 7.04 (dd, 1H), 7.32 (dd, 1H), 7.92 (d, 1H). HPLC-MS (Method B): m/z=481 (M+1), R$_t$=1.76 min.

Preparative separation of compound (5) (Method E) gave compound (7) (Rt: 20.0 min, 95.9% ee) and compound (15) (Rt: 16,5 min, 95.5% ee).

Example 6

8-(3-Aminoazepan-1-yl)-7-benzyl-1,3-dimethyl-3,7-dihydropurine-2,6-dione

TFA (6)

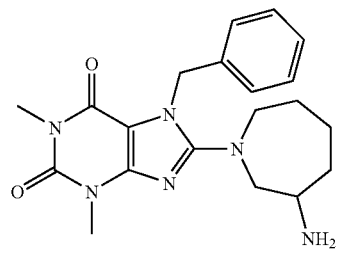

Step A: N-(2-Oxoazepan-3-yl)-4-methylbenzenesulfonamide (6A)

DL-3-Amino-E-caprolactam (3 g, 23.4 mmol) was dissolved in 140 ml of dry DCM and dry triethylamine (4.5 ml) and 4-toluenesulfonyl chloride (4.5 g, 23.6 mmol) were added. The reaction was stirred for 3 days at room temperature and then filtered through celite. The filtrate was extracted with 50 ml of 1 M aqueous potassium hydrogen sulphate, 50 ml of saturated sodium hydrogen carbonate, 50 ml of water, and 50 ml of brine, and dried over sodium sulphate. The solvent was evaporated and the residue suspended in dry dichloromethane, and compound (6A) was collected by filtration. The mother liquor was evaporated and resuspended in DCM, to give a second crop of compound (6A) as white crystals.

Combined yield: 5.99 g (90%). Mp. 179.9–180.5° C.

$^1$H-NMR (CDCl$_3$, 300 MHz) δ: 1.34 (m, 1H), 1.55–1.85 (m, 3H), 2.00 (m, 1H), 2.17 (m, 1H), 2.40 (s, 3H), 3.10 (m, 2H), 3.81 (m, 1H), 5.86 (m, 1H), 6.12 (d, 1H), 7.28 (d, 2H), 7.72 (d, 2H). HPLC-MS (Method B): m/z=283 (M+1), R$_t$=2.71 min.

Step B: N-(Azepan-3-yl)-4-methylbenzenesulfonamide (6B)

N-(2-Oxoazepan-3-yl)-4-methylbenzenesulfonamide (6A) (4.24 g, 15 mmol) was dissolved in 250 ml of dry THF under a nitrogen atmosphere, and lithium aluminium hydride (1.11 g, 30 mmol) was added slowly. The reaction was heated to reflux for 20 hours and then quenched with water until the effervescence ceased. Solid potassium carbonate was added until a white suspension appeared, and the mixture was allowed to stir for half an hour. The suspension was filtered through celite, which was washed with 3×50 ml of EtOAc. The solvents were evaporated and the residue was dissolved in 100 ml of EtOAc and 100 ml of water. The layers were separated and the aqueous layer was extracted with 2×100 ml of EtOAc. The combined organic layer was washed with brine, dried over sodium sulphate, and evaporated to give compound (6B) as an oil.

Yield: 2.89 g (71%).

$^1$H-NMR (CDCl$_3$, 300 MHz) δ: 1,37–1.74 (m, 6H), 2.41 (s, 3H), 2.55–2.93 (m, 4H), 3.45 (m, 1H), 7.27 (d, 2H), 7.76 (d, 2H). HPLC-MS (Method B): m/z=269 (M+1), R$_t$=1.43 min.

Step C: N-(1-(7-Benzyl-1.3-dimethyl-2,6-dioxo-1,2,3,6-tetrahydropurin-8-yl)azepan-3-yl)-4-methylbenzenesulfonamide (6C)

7-Benzyl-8-chloro-1,3-dimethyl-3,7-dihydropurine-2,6-dione (2A) (1.03 g, 3.40 mmol) and N-(azepan-3-yl)-4-methylbenzenesulfonamide (6B) (1.00 g, 3.73 mmol) were dissolved in 2-methoxyethanol (30 ml) and triethylamine (2.4 ml), and the mixture was heated to 120° C. for 2 days. The solvents were evaporated and the crude product was dissolved in 100 ml of EtOAc and 100 ml of water. The aqueous phase was acidified with 1M potassium hydrogen sulphate until pH=2. The organic layer was separated and extracted with 50 ml of 1M aqueous potassium hydrogen sulphate, and 50 ml of brine, and dried over sodium sulphate. The solvent was evaporated and the crude product was purified by column chromatography on silica gel using EtOAc:heptane (1:1) as the eluent. Evaporation of the solvent gave compound (6C) as a white foam.

Yield: 548 mg (30%). Mp. 80.2–88.2° C.

$^1$H-NMR (CDCl$_3$, 300 MHz) δ: 1.22–1.84 (m, 6H), 2.41 (s, 3H), 3.00 (m, 1H), 3.25 (dd, 1H), 3.47–3.72 (m, 6H), 5.37 (d, 1H), 5.59 (d, 1H), 7.03 (d, 2H), 7.29 (m, 5H), 7.75 (d, 2H), 7.88 (d, 1H). HPLC-MS (Method B): m/z=537 (M+1), R$_t$=4.32 min.

Step D: 8-(3-Aminoazepan-1-yl)-7-benzyl-1,3-dimethyl-3,7-dihydropurine-2,6-dione. TFA (6)

N-(1-(7-Benzyl-1,3-dimethyl-2,6-dioxo-1,2,3,6-tetrahydropurin-8-yl)azepan-3-yl)-4-methylbenzenesulfonamide (6C) (100 mg, 0.19 mmol) was dissolved in hydrobromic acid (48%, 5 ml) and benzene (0.07 ml), and phenol (61.4 mg, 0.65 mmol) was added. The mixture was heated to reflux for three hours, and after cooling 20 ml of EtOAc was added. The layers were separated, and the aqueous layer washed with 20 ml of EtOAc. pH was adjusted to 11 with 10M sodium hydroxide. The aqueous layer was extracted with diethyl ether (3×20 ml), and the combined organic layers were dried over sodium sulphate and the solvent was evaporated. The crude product was dissolved in 5 ml of DCM and 0.5 ml of trifluoroacetic acid was added. The solvents were evaporated and the crude product was purified by preparative HPLC (method A1, $R_t$=7.63 min). Evaporation of the solvent gave the title compound as an oil.

Yield: 8 mg (8%).

$^1$H-NMR (DMSO, 400 MHz) δ: 1.34 (m, 1H), 1.50 (m, 2H), 1.68 (m, 2H), 1.88 (m, 1H), 3.20 (s, 3H), 3.30–3.50 (m, 5H), 3.81 (m, 1H), 5.46 (d, 1H), 5.52 (d, 1H), 7.09 (m, 2H), 7.32 (m, 3H). HPLC-MS (Method B): m/z=383 (M+1), $R_t$=2.00 min.

Example 7

(S) 8-(3-Aminopyrrolidin-1-yl)-7-(2-iodobenzyl)-1,3-dimethyl-3,7-dihydropurine-2,6-dione HCl (7)

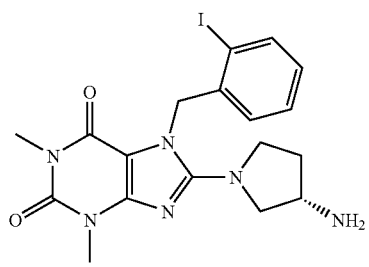

Step A: (S) (1-(7-(2-Iodobenzyl)-1,3-dimethyl-2,6-dioxo-1,2,3,6-tetrahydropurin-8-yl)pyrrolidin-3-yl)carbamic acid tert-butyl ester (7A)

8-Chloro-7-(2-iodobenzyl)-1,3-dimethyl-3,7-dihydropurine-2,6-dione (5A) (100 mg, 0.23 mmol) and (3S)-(−)-3-(tert-butoxycarbonylamino)pyrrolidine (216 mg, 1.16 mmol), and triethylamine (0.32 ml, 2.32 mmol) were dissolved in 20 ml of 2-propanol and the mixture was subjected to microwaves (method F, 130° C., 300 W) for three hours. The solvents were evaporated and the crude product was purified by preparative HPLC (method A1, $R_t$=12.99 min.). Evaporation of the solvent afforded compound (7A) as white crystals.

Yield: 132 mg (98%).

HPLC-MS (Method B): m/z=581 (M+1), $R_t$=4.42 min.

Step B: (S) 8-(3-Aminopyrrolidin-1-yl)-7-(2-iodobenzyl)-1,3-dimethyl-3,7-dihydropurine-2,6-dione. HCl (7)

(S) (1-(7-(2-iodobenzyl)-1,3-dimethyl-2,6-dioxo-1,2,3,6-tetrahydropurin-8-yl)pyrrolidin-3-yl)carbamic acid tert-butyl ester (7A) (132 mg, 0.23 mmol) was reacted and purified as described in example 3, step B, to give the title compound as white crystals.

Yield: 84 mg (72%). Mp. 119–223° C.

$^1$H-NMR (MeOD, 300 MHz) δ: 2.03 (m, 1H), 2.34 (m, 1H), 3.26 (s, 3H), 3.52 (m, 4H), 3.65 (m, 2H), 3.90 (m, 2H), 5.45 (d, 1H), 5.52 (d, 1H), 6.73 (d, 1H), 7.04 (m, 1H), 7.32 (m, 1H), 7.92 (d, 1H). HPLC-MS (Method B): m/z=481 (M+1), $R_t$=1.89 min.

Example 8

(S) 2-(8-(3-Aminopyrrolidin-1-yl)-1,3-dimethyl-2,6-dioxo-1,2,3,6-tetrahydropurin-7-ylmethyl)benzonitrile HCl (8)

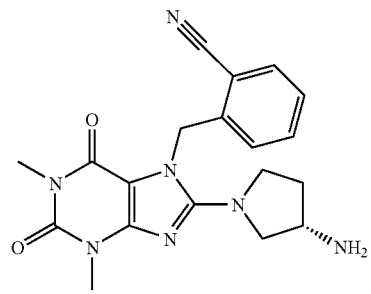

Step A: (S) (1-(7-(2-Cyanobenzyl)-1,3-dimethyl-2,6-dioxo-1,2,3,6-tetrahydropurin-8-yl)pyrrolidin-3-yl)carbamic acid tert-butyl ester (8A)

2-(8-Chloro-1,3-dimethyl-2,6-dioxo-1,2,3,6-tetrahydropurin-7-ylmethyl)benzonitrile (1 A) (100 mg, 0.30 mmol) was reacted with (3S)-(−)-3-(tert-butoxycarbonylamino)pyrrolidine (282 mg, 1.52 mmol), and purified as described in example 7, step A, to afford compound (8A) as white crystals.

Yield: 117 mg (81%).

Prep. HPLC, (method A1): $R_t$=11.50 min.

HPLC-MS (Method B): m/z=480 (M+1), $R_t$=3.75 min.

Step B: (S) 2-(8-(3-Aminopyrrolidin-1-yl)-1,3-dimethyl-2,6-dioxo-1,2,3,6-tetrahydropurin-7-ylmethyl)benzonitrile. HCl (8)

(S) (1-(7-(2-Cyanobenzyl)-1,3-dimethyl-2,6-dioxo-1,2,3,6-tetrahydropurin-8-yl)pyrrolidin-3-yl)carbamic acid tert-butyl ester (8A) (117 mg, 0.24 mmol) was reacted and purified as described in example 3, step B, to give the title compound as white crystals.

Yield: 51 mg (50%). Mp.104–117° C.

$^1$H-NMR (MeOD, 300 MHz) δ: 2.08 (m, 1H), 2.40 (m, 1H), 3.26 (s, 3H), 3.52 (s, 3H), 3.53–3.78 (m, 3H), 3.92 (m, 2H), 5.71 (d, 1H), 5.78 (d, 1H), 7.13 (d, 1H), 7.47 (m, 1H), 7.62 (m, 1H), 7.80 (d, 1H). HPLC-MS (Method B): m/z=380 (M+1), $R_t$=1.34 min.

Example 9

8-(3-Aminopiperidin-1-yl)-7-(2-iodobenzyl)-1,3-dimethyl-3,7-dihydropurine-2,6-dione

TFA (9)

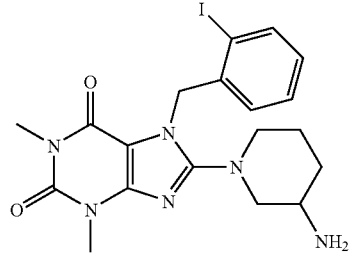

8-Chloro-7-(2-iodobenzyl)-1,3-dimethyl-3,7-dihydropurine-2,6-dione (5A) (100 mg, 0.23 mmol) and 3-aminopiperidine dihydrochloride (202 mg, 1.16 mmol) were reacted and purified as described in example 1, step B, to give the title compound as oily brown crystals.

Yield: 19 mg (13%).

Prep. HPLC (method A1): $R_t$=7.70 min.

$^1$H-NMR (MeOD, 300 MHz) δ: 1.62 (m, 2H), 1.74 (m, 1H), 2.08 (m, 1H), 2.94 (m, 1H), 3.18 (m, 2H), 3.28 (s, 3H), 3.46 (m, 1H), 3.54 (s, 3H), 3.70 (m, 1H), 5.35 (s, 2H), 6.78 (d, 1H), 7.04 (m, 1H), 7.32 (m, 1H), 7.92 (d, 1H).

HPLC-MS (Method B): m/z=495 (M+1), $R_t$=2.09 min.

Example 10

8-(3-Aminopiperidin-1-yl)-7-(2-bromobenzyl)-1,3-dimethyl-3,7-dihydropurine-2,6-dione TFA (10)

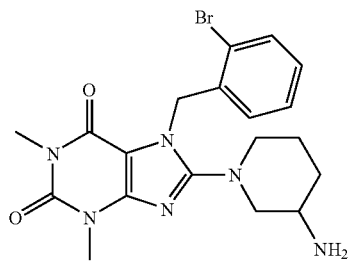

Step A: 7-(2-Bromobenzyl)-8-chloro-1,3-dimethyl-3,7-dihydropurine-2,6-dione (10A)

8-Chlorotheophylline (10 g, 46.6 mmol) was dissolved in 250 ml of DMF and 8 ml of DIEA, and 2-bromobenzyl bromide (12.2 g, 48.9 mmol) was added. The mixture was stirred at 65° C. for 2 hours. The reaction mixture was added 20 ml of EtOAc and 250 ml of cold water. The white precipitate was collected by filtration to afford compound (10A) as white crystals.

Yield: 17.2 g (96%). Mp. 165.4–166.7° C.

$^1$H-NMR (CDCl$_3$, 300 MHz) δ: 3.37 (s, 3H), 3.60 (s, 3H), 5.67 (s, 2H), 6.57 (d, 1H), 7.20 (m, 2H), 7.62 (d, 1H). HPLC-MS (Method B): m/z=385 (M+2), $R_t$=3.77 min.

Step B: 8-(3-Aminopiperidin-1-yl)-7-(2-bromobenzyl)-1,3-dimethyl-3,7-dihydropurine-2,6-dione. TFA (10)

7-(2-Bromobenzyl)-8-chloro-1,3-dimethyl-3,7-dihydropurine-2,6-dione (10A) (100 mg, 0.26 mmol) and 3-aminopiperidine dihydrochloride (226 mg, 1.31 mmol) were dissolved in 2-propanol (20 ml), triethylamine (0.109 ml, 0.78 mmol) and DMF (5 ml) and subjected to microwaves (method F, 130° C., 300 W) for ten hours. The solvents were evaporated and the crude product was purified by preparative HPLC, (method A1, Rt=7.52 min.) to give the title compound as a brown oil.

Yield: 10 mg (7%).

HPLC-MS (Method B): m/z=447 (M+), $R_t$=2.05 min.

Example 11

(R) 8-(3-Aminopyrrolidin-1-yl)-7-(2-bromobenzyl)-1,3-dimethyl-3,7-dihydropurine-2,6-dione

TFA(11)

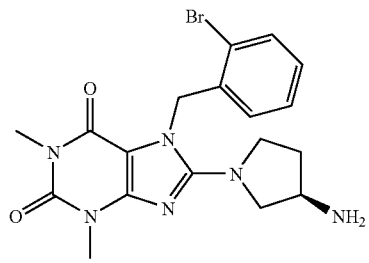

Step A: (R) (1-(7-(2-Bromobenzyl)-1,3-dimethyl-2,6-dioxo-1,2,3,6-tetrahydropurin-8-yl)pyrrolidin-3-yl)carbamic acid tert-butyl ester (11A)

7-(2-Bromobenzyl)-8-chloro-1,3-dimethyl-3,7-dihydropurine-2,6-dione (10A) (100 mg, 0.26 mmol) and (3R)-(+)-3-(tert-butoxycarbonylamino)pyrrolidine (243 mg, 1.30 mmol) were reacted and purified as described in example 3, step A, to give compound (11A) as brown crystals.

Yield: 44 mg (32%). Mp. 104–106° C.

Prep. HPLC, (method A1): Rt=12.66 min.

$^1$H-NMR (MeOD, 200 MHz) δ: 1.40 (s, 9H), 1.83 (m, 1H), 2.07 (m, 1H), 3.25 (s, 3H), 3.37 (m, 1H), 3.48–3.78 (m, 6H), 4.04 (m, 1H), 5.57 (s, 2H), 6.74 (d, 1H), 7.23 (m, 2H), 7.62 (m, 1H).

HPLC-MS (Method B): m/z=535 (M+2), $R_t$=4.08 min

Step B: (R) 8-(3-Aminopyrrolidin-1-yl)-7-(2-bromobenzyl)-1,3-dimethyl-3,7-dihydropurine-2,6-dione. TFA (11)

(R) (1-(7-(2-Bromobenzyl)-1,3-dimethyl-2,6-dioxo-1,2,3,6-tetrahydropurin-8-yl)pyrrolidin-3-yl)carbamic acid tert-butyl ester (11A) (44 mg, 0.08 mmol) was dissolved in MeCN (1 ml), water (1 ml), and TFA (0.32 ml), and the mixture was stirred at room temperature for 2 days. The solvents were evaporated and the crude product was purified by preparative HPLC (method A1, $R_t$=6.92 min.) to give the title compound as a brown oil.

Yield: 40 mg (88%).

$^1$H-NMR (MeOD, 300 MHz) δ: 2.05 (m, 1H), 2.35 (m, 1H), 3.25 (s, 3H), 3.50–3.74 (m, 6H), 3.90 (m, 2H), 5.54 (d, 1H), 5.61 (d, 1H), 6.80 (dd, 1H), 7.21 (dt, 1H), 7.30 (dt, 1H), 7.63 (dd, 1H). HPLC-MS (Method B): m/z=433 (M+), $R_t$=1.83 min.

Example 12

(S) 8-(3-Aminopyrrolidin-1-yl)-7-(2-bromobenzyl)-1,3-dimethyl-3,7-dihydropurine-2,6-dione HCl (12)

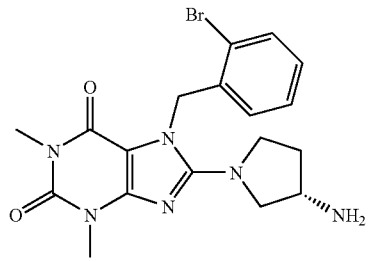

7-(2-Bromobenzyl)-8-chloro-1,3-dimethyl-3,7-dihydropurine-2,6-dione (10A) (100 mg, 0.26 mmol) and (S)-(−)-3-aminopyrrolidine (112 mg, 1.30 mmol) were dissolved in 2-propanol (20 ml) and DMF (5 ml) and subjected to microwaves (method F, 130° C., 300 W) for 10 hours. The solvents were evaporated and the crude product was purified by preparative HPLC (method A1, Rt=6.92 min.) to give the title compound as brown crystals.

Yield: 50 mg (41%). Mp. 215–217° C.

$^1$H-NMR (MeOD, 200 MHz) δ: 2.04 (m, 1H), 2.33 (m, 1H), 3.25 (s, 3H), 3.48–3.78 (m, 6H), 3.90 (m, 2H), 5.53 (d, 1H), 5.60 (d, 1H), 6.80 (dd, 1H), 7.25 (m, 2H), 7.63 (dd, 1H). HPLC-MS (Method B): m/z=433 (M+), R$_t$=1.80 min.

Example 13

(R) 8-(3Aminopyrrolidin-1-yl)-7-benzyl-1,3-dimethyl-3,7-dihydropurine-2,6-dione

HCl (13)

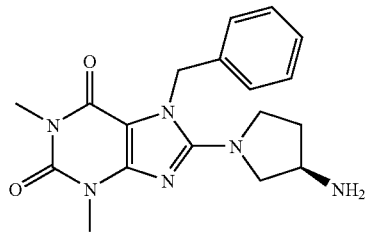

7-Benzyl-8-chloro-1,3-dimethyl-3,7-dihydropurine-2,6-dione (2A) (100 mg, 0.33 mmol) and (R)-(+)-3-aminopyrrolidine (141 mg, 1.64 mmol) were reacted and purified as described in example 12 to give the title compound as brown crystals.

Yield: 73 mg (57%). Mp. 103–114° C.

Prep. HPLC, (method A1): Rt=6.38 min.

$^1$H-NMR (MeOD, 200 MHz) δ: 2.08 (m, 1H), 2.35 (m, 1H), 3.27 (s, 3H), 3.49 (s, 3H), 3.55–4.00 (m, 5H), 5.52 (d, 1H), 5.63 (d, 1H), 7.12 (m, 2H), 7.29 (m, 3H). HPLC-MS (Method B): m/z=355 (M+1), R$_t$=1.55 min.

Example 14

(R) 2-(8-(3-Aminopyrrolidin-1-yl)-1,3-dimethyl-2,6-dioxo-1,2,3,6-tetrahydropurin-7-ylmethyl)benzonitrile HCl (14)

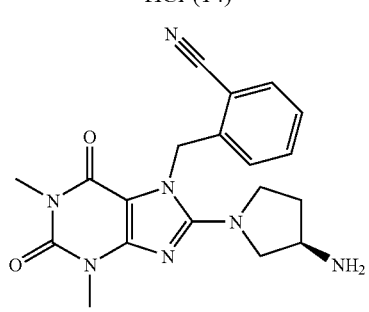

2-(8-Chloro-1,3-dimethyl-2,6-dioxo-1,2,3,6-tetrahydropurin-7-ylmethyl)benzonitrile (1A) (100 mg, 0.30 mmol) and (R)-(+)-3-aminopyrrolidine (131 mg, 1.57 mmol) were reacted and purified as described in example 2, step B, to give the title compound as brown crystals.

Yield: 125 mg (99%). Mp. 202–204° C.

Prep. HPLC, (method A1): Rt=6.17 min.

$^1$H-NMR (MeOD, 200 MHz) δ: 2.12 (m, 1H), 2.41 (m, 1H), 3.22 (s, 3H), 3.49 (s, 3H), 3.55–4.04 (m, 5H), 5.70 (d, 1H), 5.78 (d, 1H), 7.11 (d, 1H), 7.47 (t, 1H), 7.61 (t, 1H), 7.78 (d, 1H). HPLC-MS (Method B): m/z=380 (M+1), R$_t$=1.38 min.

Example 15

(R) 8-(3-Aminopyrrolidin-1-yl)-7-(2-iodobenzyl)-1,3-dimethyl-3,7-dihydropurine-2,6-dione HCl (15)

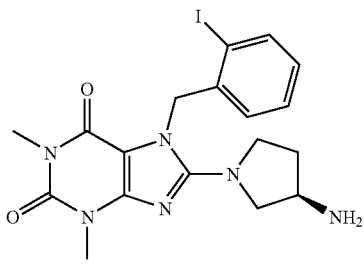

8-Chloro-7-(2-iodobenzyl)-1,3-dimethyl-3,7-dihydropurine-2,6-dione (5A) (100 mg, 0.23 mmol) and (R)-(+)-3-aminopyrrolidine (100 mg, 1.16 mmol) were reacted and purified as described in example 2, step B, to give the title compound as white crystals.

Yield: 61 mg (51%). Mp. 233–235° C.

Prep. HPLC, (method A1): Rt=7.24 min.

$^1$H-NMR (MeOD, 200 MHz) δ: 2.05 (m, 1H), 2.34 (m, 1H), 3.25 (s, 3H), 3.46–3.76 (m, 6H), 3.90 (m, 2H), 5.43 (d, 1H), 5.52 (d, 1H), 6.72 (dd, 1H), 7.03 (dt, 1H), 7.32 (dt, 1H), 7.91 (dd, 1H). HPLC-MS (Method B): m/z=481 (M+1), R$_t$=1.88 min.

Example 16

General Procedure (E)

(R) 2-[8-(3-Aminopiperidin-1-yl)-1,3-dimethyl-2,6-dioxo-1,2,3,6-tetrahydropurin-7-ylmethyl]-benzonitrile HCl (16)

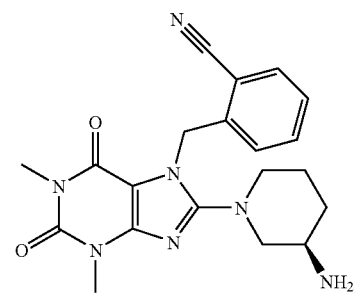

Step A: 2-(8-Chloro-1,3-dimethyl-2,6-dioxo-1,2,3,6-tetrahydropurin-7-ylmethyl)benzonitrile (16A)

From 2-Cyanobenzyl bromide.

Yield: 28.6 g (93%). Mp. 222.5–223.7° C.

¹H-NMR (DMSO, 300 MHz) δ: 7.93 (d, 1H), 7.66 (t, 1H), 7.52 (t, 1H), 7.07 (d, 1H), 5.75 (s, 2H), 3.42 (s, 3H), 3.20 (s, 3H). HPLC-MS (Method B): m/z=330 (M), $R_t$=2.93 min.

Step B: (R) 1-[7-(2-Cyanobenzyl)-1,3-dimethyl-2,6-dioxo-1,2,3,6-tetrahydropurin-8-yl]-piperidin-3-yl)carbamic acid tert-butyl ester (16B)

From (16A) (4 g, 12.1 mmol)

Yield: 4.8 g (80%)

Step C: (R) 2-[8-(3-Aminopiperidin-1-yl)-1,3-dimethyl-2,6-dioxo-1,2,3,6-tetrahydropurin-7-ylmethyl]benzonitrile.

HCL (16)

From (16B) (4.8 g, 9.7 mmol)

Yield: 2.49 g (59%) of the title compound.

¹H-NMR (CDCl3, 200 MHz) δ: 8.59(s, 2H), 7.67(m, 1H), 7.56(m, 1H), 7.39(m, 1H), 7.17(m, 1H), 5.64(s, 2H), 3.95(s, 1H), 3.68(m, 2H), 3.51(s, 4H), 3.30(s, 3H), 3.01(s, 2H), 2.00(m, 2H), 1.65(s, 1H). ¹³C-NMR (CDCl3, 200 MHz) δ:155.76, 154.48, 151.46, 147.16, 140.17, 133.56, 133.18, 128.37, 127.47, 117.18, 110.54, 104.98, 58.07, 52.26, 51.54, 47.13, 46.91, 30.00, 27.91, 27.47, 21.72, 18.35.

Example 17

General Procedure (E)

(R) 8-(3-Aminopiperidin-1-yl)-7-benzyl-1,3-dimethyl-3,7-dihydropurine-2,6-dione

HCl (17)

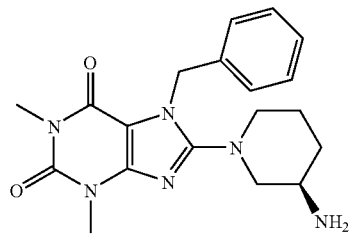

Step A: 7-Benzyl-8-chloro-1,3-dimethyl-3,7-dihydropurine-2,6-dione (17A)

From 8-Chlorotheophylline (50 g, 233 mmol) and benzyl bromide.

The reaction mixture was evaporated to dryness in vacuo, dissolved in DCM (400 ml) and water (250 ml). The separated aqueous phase was extracted with DCM (150 ml), and the combined DCM phases were washed with brine, dried (MgSO₄), and evaporated in vacuo.

Yield: 73.6 g (app. 100%). Mp. 152–154° C.

¹H-NMR (CDCl3, 200 MHz) δ: 7.35 (m, 5H), 5.55 (s, 2H), 3.55 (s, 3H), 3.42 (s, 3H). HPLC-MS (Method B): m/z=305 (M+1), $R_t$=3.33 min.

Step B: (R) [1-(7-Benzyl-1,3-dimethyl-2,6-dioxo-1,2,3,6-tetrahydropurin-8-yl)piperidin-3-yl]carbamic acid tert-butyl ester (17B)

From (17A) (4 g, 13.1 mmol)

Yield: 5.1 g (84%)

Step C: (R) 8-(3-Aminopiperidin-1-yl)-7-benzyl-1,3-dimethyl-3,7-dihydropurine-2,6-dione HCl (17)

From (17B) (4.1 g, 10.9 mmol)

Yield: 2.6 g (67%) of the title compound.

¹H-NMR (CDCl3, 200 MHz) δ: 7.29(m, 5H), 5.45(dd, 2H), 3.72(m, 2H), 3.52(s, 4H), 3.37(s, 3H), 3.28(m, 1H), 3.10(m, 1H), 2.93(m, 1H), 2.14(m, 1H), 1.84(m, 2H), 1.57(s, 1H). HPLC-MS (Method B): m/z=369 (M+1), $R_t$=3.69 min.

Example 18

General Procedure (E)

(R) 8-(3-Aminopiperidin-1-yl)-1,3-dimethyl-7-(2-methylbenzyl)-3,7-dihydropurine-2,6-dione HCl (18)

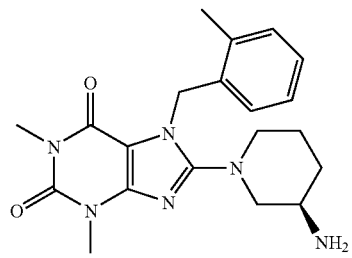

Step A: 8-Chloro-1,3-dimethyl-7-(2-methylbenzyl)-3,7-dihydropurine-2,6-dione (18A)

From 8-Chorotheophylline (10 g, 47 mmol) and 2-methylbenzyl bromide (13.6 ml, 103 mmol). The benzyl bromide was added in two portions. First half at reaction start as described in general procedure (E), and the other half after 24 hours as the reaction had not completed.

Yield: 12.8 g (86%). Mp.164.9–165.2° C.

¹H-NMR (CDCl3, 200 MHz) δ: 7.3–7.05 (m, 3H), 6.55 (d, 1H), 5.55 (s, 2H), 3.57 (s, 3H), 3.34 (s, 3H), 2.42 (s, 3H). HPLC-MS (Method B): m/z=319 (M+1), $R_t$=3.76 min.

Step B: (R) (1-[1,3-Dimethyl-7-(2-methylbenzyl)-2,6-dioxo-1,2,3,6-tetrahydropurin-8-yl]piperidin-3-yl)carbamic acid tert-butyl ester (18B)

From (18A) (4 g, 12.5 mmol)

Yield: 4.9 g (82%).

Step C: (R) 8-(3-Aminopiperidin-1-yl)-1,3-dimethyl-7-(2-methylbenzyl)-3,7-dihydropurine-2,6-dione. HCl (18)

From (18B) (4.9 g, 10.2 mmol)

Yield: 3.27 g (76%) of the title compound.

¹H-NMR (CDCl3, 200 MHz) δ: 7.14(m, 3H), 6.67(d, 1H), 5.39(d, 2H), 3.80(s, 3H), 3.71(m, 1H), 3.52(s, 4H), 3.34(m, 4H), 3.02(s, 2H), 2.38(s, 3H), 2.10(s, 1H), 1.81(s, 2H), 1.54(s, 1H)

¹³C-NMR (CDCl3, 200 MHz) δ:155.74, 154.53, 151.83, 147.29, 134.83, 134.54, 130.55, 127.61, 126.48, 124.62, 105.44, 52.03, 51.01, 46.88, 29.85, 27.92, 27.65, 22.11, 19.08.

Example 19

General Procedure (E)

(R) 8-(3-Aminopiperidin-1-yl)-7-(2-chlorobenzyl)-1,3-dimethyl-3,7-dihydropurine-2,6-dione HCl (19)°

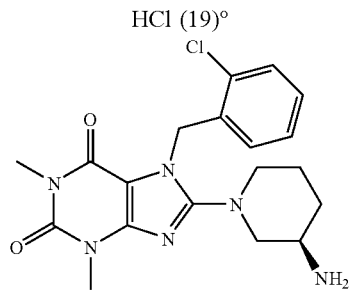

Step A: 8-Chloro-7-(2-chlorobenzyl)-1,3-dimethyl-3,7-dihydropurine-2,6-dione (19A)

From 8-Chorotheophylline (10 g, 47 mmol)) and 2-chlorobenzyl chloride (19.4 ml, 153.9 mmol). The 2-chlorobenzyl chloride was added in three portions. First third at reaction start as described in general procedure (E), and the other thirds after 24 and 48 hours respectively as the reaction had not completed. Total reaction time 7 days at RT. Due to incomplete precipitation in water the product was extracted with DCM (700 and 300 ml), dried (MgSO$_4$), and evaporated to dryness in vacuo. Excess 2-chlorobenzyl bromide was removed by washing the product in Et$_2$O.

Yield: 15.6 g (99%). Mp.189.7–191.8° C.
$^1$H-NMR (CDCl3, 200 MHz) δ: 7.42 (d, 1H), 7.30–7.12 (m, 2H, 6.67 (d, 1H), 5.7 (s, 2H), 3.57 (s, 3H), 3.35 (s, 3H). HPLC-MS (Method B): m/z=339 (M+1), R$_t$=3.90 min.

Step B: (R) (1-[7-(2-Chlorobenzyl)-1,3-dimethyl-2,6-dioxo-1,2,3,6-tetrahydropurin-8-yl]piperidin-3-yl)carbamic acid tert-butyl ester (19B)

From (19A) (5.89 g, 17.4 mmol)
Yield: 8.87 g (app. 100%).

Step C: (R) 8-(3-Aminopiperidin-1-yl)-7-(2-chlorobenzyl)-1,3-dimethyl-3,7-dihydropurine-2,6-dione. HCl (19)

From (19B) (8.87 g, 17.6 mmol)
Yield: 2.49 g (59%) of the title compound.
$^1$H-NMR (CDCl3, 200 MHz) δ: 8.57(s, 3H), 7.27(m, 3H), 6.87(m, 1H), 5.47(m, 2H), 3.19–3.82(m, 9H), 2.97(s, 2H), 2.12(s, 1H), 1.84(m, 2H), 1.53(s, 1H)
$^{13}$C-NMR (CDCl3, 200 MHz) δ: 155.53, 154.34, 151.56, 147.16, 132.02, 129.64, 129.02, 127.39, 127.02, 105.27, 74.83, 51.93, 51.07, 46.98, 46.72, 29.93, 27.73, 22.05.

Example 20

General Procedure (E)

(R) 8-(3-Aminopiperidin-1-yl)-7-(2-bromobenzyl)-1,3-dimethyl-3,7-dihydropurine-2,6-dione HCl (20)

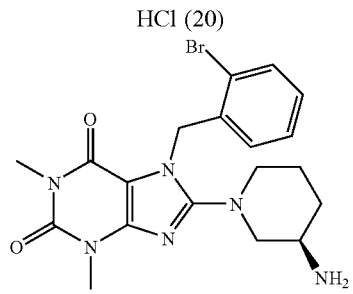

Step A: 7-(2-Bromobenzyl)-8-chloro-1,3-dimethyl-3,7-dihydropurine-2,6-dione (20A)

From 8-Chorotheophylline (10 g, 46.6 mol) and 2-bromobenzyl bromide (12.2 g, 48.93 mol).
Yield: 17.2 g (96%).
$^1$H-NMR (CDCl3, 200 MHz) δ: 7.62(m, 1H), 7.21(m, 2H), 6.58(m, 1H), 5.67(s, 2H), 3.60(s, 3H), 3.38(s, 3H). HPLC-MS (Method B): m/z=384 (M+1).

Step B: (R) (1-[7-(2-Bromobenzyl)-1,3-dimethyl-2,6-dioxo-1,2,3,6-tetrahydropurin-8-yl]piperidin-3-yl)carbamic acid tert-butyl ester (20B)

From (20A) (6.08 g, 15.8 mmol)
Yield: 8.78 g (app. 100%).

Step C: (R) 8-(3-Aminopiperidin-1-yl)-7-(2-bromobenzyl)-1,3-dimethyl-3,7-dihydropurine-2,6-dione. HCl (20)

From (20B) (8.78 g, 16.1 mmol)
Yield: 3.73 g (52%) of the title compound.
$^1$H-NMR (MeOD, 200 MHz) δ:
$^{13}$C-NMR (CDCl$_3$, 200 MHz) δ:155.52, 154.28, 151.55, 147.16, 135.57, 132.92, 129.28, 128.01, 127.03, 121.78, 105.23, 51.95, 51.01, 49.19, 47.01, 29.95, 27.93, 27.81, 22.22.

Example 21

General Procedure (G)

(R) 8-(3-Aminopiperidin-1-yl)-7-(2-bromobenzyl)-3-methyl-1-(2-oxo-2-phenylethyl)-3,7-dihydro-purine-2,6-dione

TFA (21)

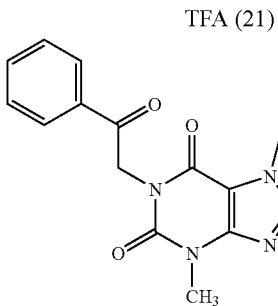

Yield: 130 mg (41%)
Prep. HPLC, (method A1): Rt=8.86 min.
HPLC-MS (Method B): m/z=551.1 (M+), R$_t$=2.83 min.

Example 22

General Procedure (G)

(R) 8-(3-Aminopiperidin-1-yl)-7-(2-bromobenzyl)-3-methyl-1-phenethyl-3,7-dihydropurine-2,6-dione

TFA (22)

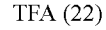

Yield: 257 mg (82%)
Prep. HPLC, (method A1): Rt=9.20 min.
HPLC-MS (Method B): m/z=539.2 (M+1), R$_t$=3.23 min.

Example 23

General Procedure (G)

(R) 8-(3-Aminopiperidin-1-yl)-7-(2-chlorobenzyl)-3-methyl-1-phenethyl-3,7-dihydropurine-2,6-dione

TFA (23)

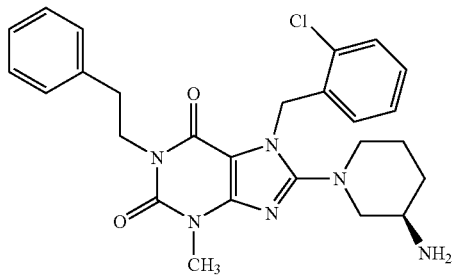

Yield: 34 mg (13%)
Prep. HPLC, (method A1): Rt=9.83 min.
HPLC-MS (Method B): m/z=493.2 (M+), $R_t$=2.94 min.

Example 24

General Procedure (G)

(R) 2-[8-(3-Aminopiperidin-1-yl)-7-(2-chlorobenzyl)-3-methyl-2,6-dioxo-1,2,3,6-tetrahydropurin-1-ylmethyl]benzonitrile (24)

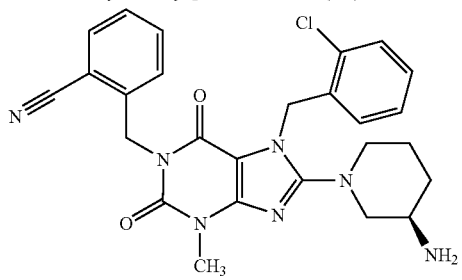

$^1$H NMR (CDCl$_3$): δ=8.25 (s, br, 2H), 7.6 (d, 1H), 7.3 (m, 6H), 6.85 (dd, 1H), 6.3 (s, br, 1H), 5.45 (s, 1H), 5.35 (s, 2H), 5.25 (s, 1H), 3.65 (m, 3H), 3.45 (s, 3H), 3.0 (m, 2H), 2.15–1.3 (m, 4H). HPLC-MS (Method B): m/z=505 (M+1), $R_t$=2.9 min.

Example 25

General Procedure (D)

2-[8-(3-Aminopiperidin-1-yl)-7-(2-cyanobenzyl)-3-methyl-2,6-dioxo-1,2,3,6-tetrahydropurin-1-ylmethyl]benzonitrile (25)

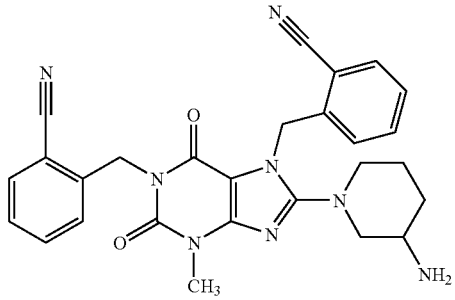

$^1$H NMR (DMSO-d$_6$): δ 7.87 (d, 1H), 7.80 (d, 1H), 7.65 (t, 1H), 7.57 (t, 1H), 7.49 (t, 1H), 7.42 (t, 1H), 7.12 (d, 2H), 5.54 (s, 2H), 5.15 (s, 2H), 3.42 (s, 3H), 2.86 (m, 1H), 2.64 (m, 2H), 1.78 (m, 1H), 1.66 (m, 1H), 1.47 (m, 1H), 1.15 (m, 1H). HPLC-MS (Method B): m/z=495 (M+1) 518 (M+23), $R_t$=2.28 min.

Example 26

General Procedure (D)

(R) 2-[8-(3-Aminopiperidin-1-yl)-7-(2-cyanobenzyl)-3-methyl-2,6-dioxo-1,2,3,6-tetrahydropurin-1-ylmethyl]benzonitrile

TFA (26)

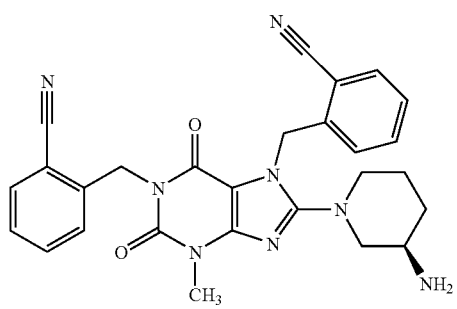

$^1$H NMR (DMSO-d$_6$): δ 8.1 (s, 3H), 7.87 (d, 1H), 7.80 (d, 1H), 7.70–7.33 (m, 4H), 7.095 (dd, 2H), 5.54 (s, 2H), 5.13 (s, 2H), 3.65–3.53 (m, 1H), 3.43 (s, 3H), 3.40–3.26 (m, 1H), 3.26–3.05 (m, 2H), 3.01–2.87 (m, 1H), 2.04–1.68 (m, 2H), 1.65–1.44 (m, 2H). HPLC-MS (Method B): m/z=495 (M+1), $R_t$=2.503 min.

Example 27

General Procedure (E)

(R) 2-[8-(3-(R)-Aminopiperidin-1-yl)-3-methyl-2,6-dioxo-1,2,3,6-tetrahydropurin-7-ylmethyl]benzonitrile HCl (27)

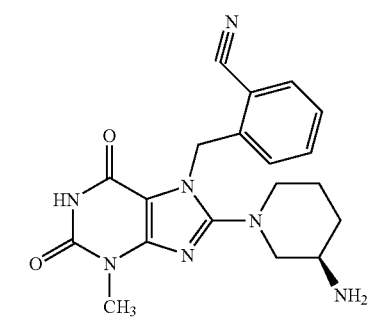

$^1$H NMR (DMSO-d$_6$): δ 10.95 (s, 1H), 8.24 (s, 3H), 7.875 (d, 1H), 7.65 (t, 1H), 7.49 (t, 1H), 7.085 (d, 1H), 5.50 (s, 2H), 3.62–3.49 (m, 2H), 3.19–3.02 (m, 2H), 2.87 (t, 1H), 2.02–1.42 (m, 4H). HPLC-MS (Method B): m/z=380 (M+1), $R_t$=1.361 min.

Example 28

General Procedure (E)

(R) 8-(3-Aminopiperidin-1-yl)-7-(2-chlorobenzyl)-3-methyl-3,7-dihydropurine-2,6-dione HCl (28)

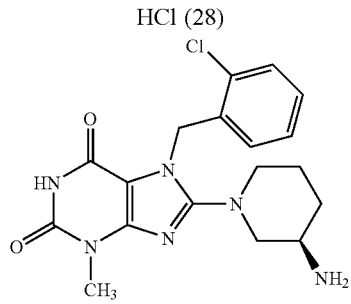

$^1$H NMR (DMSO-d$_6$): δ 10.95 (s, 1H), 8.35 (s br, 3H), 7.50 (d, 2H), 7.31 (dt, 2H), 6.87 (d, 1H), 5.38 (s, 2H), 3.56 (m, 1H), 3.36 (s, 3H), 3.20 (s br, 1H), 3.18–3.00 (m, 2H), 2.79 (t, 1H), 1.91 (s br, 1H), 1.72 (s br, 1H), 1.60–1.30 (m, 2H).

Example 29

General Procedure (G)

(R) 8-(3-Aminopiperidin-1-yl)-7-(2-bromobenzyl)-3-methyl-1-(2-oxo-2-thiophen-3-yl-ethyl)3,7-dihydropurine-2,6-dione HCl (29)

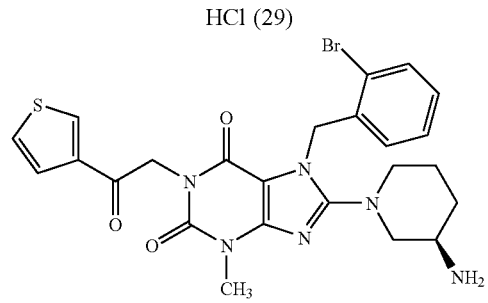

$^1$H NMR (DMSO-d$_6$): δ 8.70 (s, 1H), 8.34 (s, 3H), 7.65–7.70(m, 2H), 7.54 (d, 1H), 7.34 (t, 1H), 7.24 (t, 1H), 6.84 (d, 1H), 5.34 (s, 2H), 5.18 (s, 2H), 3.60–3.66 (m, 1H), 3.46 (s, 3H), 3.05–3.35(m, 3H), 2.80–2.90(m, 1H), 1.40–2.00(m, 4H). HPLC-MS (Method B): m/z=558 (M+1), R$_t$=3.90 min.

Example 30

General Procedure (G)

(R) 2-[8-(3-Aminopiperidin-1-yl)-3-methyl-2,6-dioxo-1-(2-oxo-2-thiophen-3-yl-ethyl)-1,2,3,6-tetrahydropurin-7-ylmethyl]benzonitrile

TFA (30)

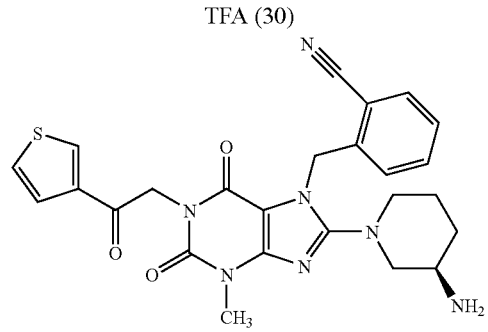

$^1$H NMR (DMSO-d$_6$): δ 8.68–8.70 (m, 1H), 8.10–8.20 (m, 3H), 7.86–7.90 (d, 1H) 7.45–7.70 (m, 4H), 7.05–7.10 (d, 1H), 5.53(s, 2H), 5.18 (s, 2H), 3.56–3.64 (m, 1H), 3.46 (s, 3H), 3.10–3.25(m, 2H), 2.90–3.00(m, 1H), 1.50–2.20(m, 4H). HPLC-MS (Method B): m/z=504, Rt=2.23 min.

Example 31

General Procedure (F)

8-(3-Amino-piperidin-1-yl)-3-benzyl-7-(3-fluoro-benzyl)-3,7-dihydro-purine-2,6-dione (31)

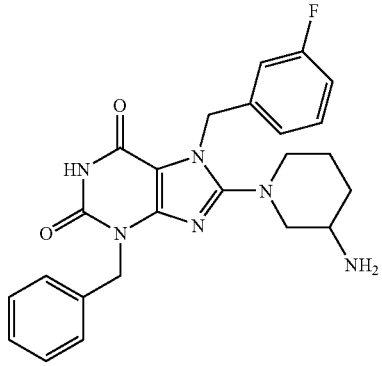

HPLC-MS (Method A3): m/z=449 (M+1), R$_t$=3.60 min.

Example 32

General Procedure (F)

8-(3-Amino-piperidin-1-yl)-3-benzyl-7-(2-chloro-benzyl)-3,7-dihydro-purine-2,6-dione (32)

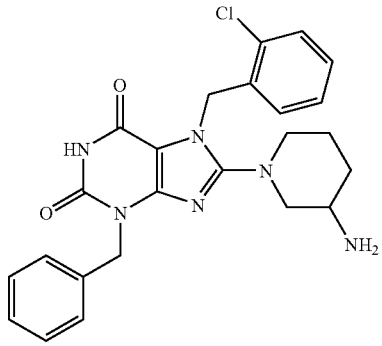

HPLC-MS (Method A3): m/z=465 (M+1), R$_t$=3.40 min.

Example 33

General Procedure (F)

8-(3-Amino-piperidin-1-yl)-3-benzyl-7-(2-bromo-benzyl)-3,7-dihydro-purine-2,6-dione (33)

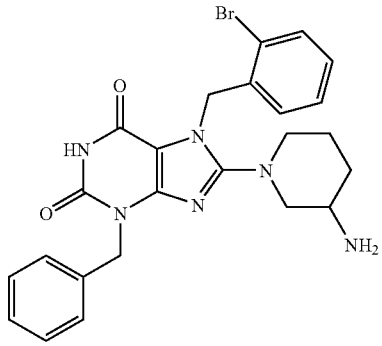

HPLC-MS (Method A3): m/z=508 (M+1), R$_t$=3.50 min.

Example 34

General Procedure (F)

8-(3-Amino-piperidin-1-yl)-3-benzyl-7-(2-methyl-benzyl)-3,7-dihydro-purine-2,6-dione (34)

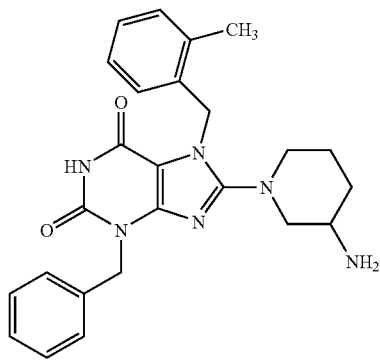

HPLC-MS (Method A3): m/z=445 (M+1), $R_t$=3.50 min.

Example 35

General Procedure (F)

8-(3-Amino-piperidin-1-yl)-3,7-dibenzyl-3,7-dihydro-purine-2,6-dione (35)

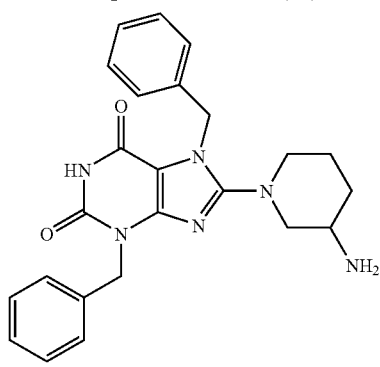

HPLC-MS (Method A3): m/z=431 (M+1), $R_t$=3.40 min.

Example 36

General Procedure (F)

8-(3-Amino-piperidin-1-yl)-3-benzyl-7-(3,5-difluoro-benzyl)-3,7-dihydro-purine-2,6-dione (36)

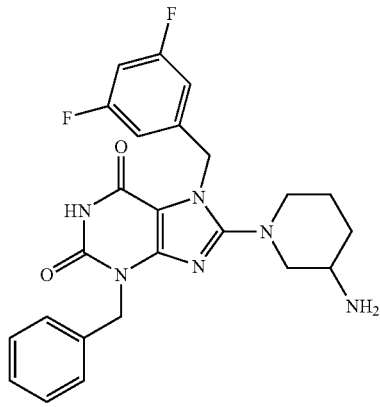

HPLC-MS (Method A3): m/z=467 (M+1), $R_t$=3.50 min.

Example 37

General Procedure (F)

8-(3-Amino-piperidin-1-yl)-3-benzyl-7-(2,5-difluoro-benzyl)-3,7-dihydro-purine-2,6-dione (37)

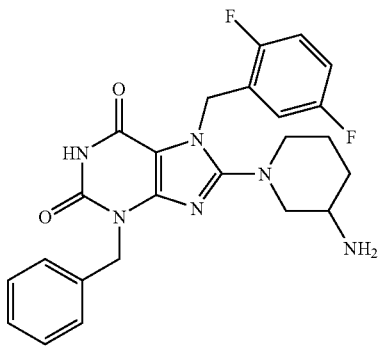

HPLC-MS (Method A3): m/z=467 (M+1), $R_t$=3.30 min.

Example 38

General Procedure (F)

8-(3-Amino-piperidin-1-yl)-3-benzyl-7-(2-difluoromethoxy-benzyl)-3,7-dihydro-purine-2,6-dione (38)

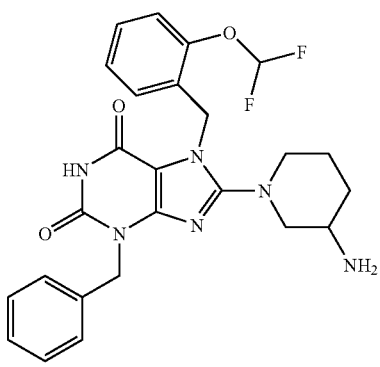

HPLC-MS (Method A3): m/z=497 (M+1), $R_t$=3.50 min.

Example 39

General Procedure (F)

8-(3-Amino-piperidin-1-yl)-7-(3-fluoro-benzyl)-3-methyl-3,7-dihydro-purine-2,6-dione (39)

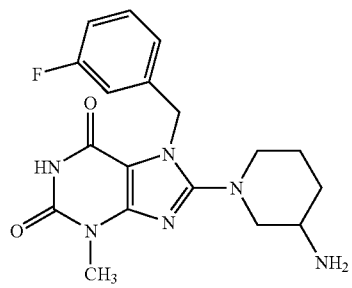

HPLC-MS (Method A3): m/z=373 (M+1), $R_t$=2.30 min.

Example 40

General Procedure (F)

8-(3-Amino-piperidin-1-yl)-7-(2-chloro-benzyl)-3-methyl-3,7-dihydro-purine-2,6-dione (40)

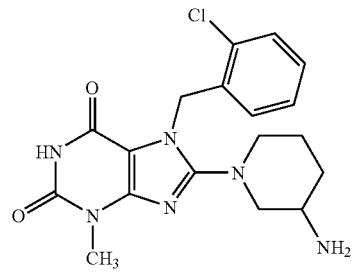

HPLC-MS (Method A3): m/z=389 (M+1), $R_t$=2.40 min.

Example 41

General Procedure (F)

8-(3-Amino-piperidin-1-yl)-3-methyl-7-(2-methyl-benzyl)-3,7-dihydro-purine-2,6-dione (41)

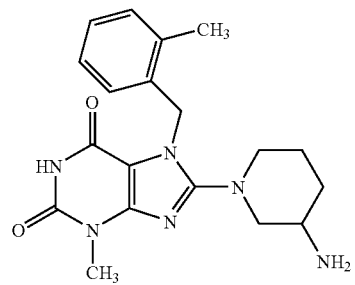

HPLC-MS (Method A3): m/z=369 (M+1), $R_t$=2.40 min.

Example 42

General Procedure (F)

8-(3-Amino-piperidin-1-yl)-7-benzyl-3-methyl-3,7-dihydro-purine-2,6-dione (42)

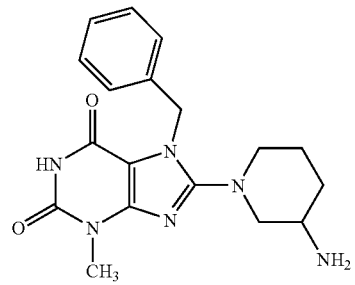

HPLC-MS (Method A3): m/z=355 (M+1), $R_t$=2.10 min.

Example 43

General Procedure (F)

8-(3-Amino-piperidin-1-yl)-7-(3,5-difluoro-benzyl)-3-methyl-3,7-dihydro-purine-2,6-dione (43)

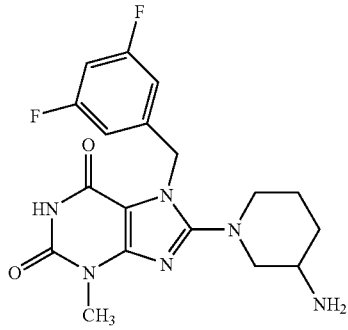

HPLC-MS (Method A3): m/z=391 (M+1), $R_t$=2.85 min.

Example 44

General Procedure (F)

8-(3-Amino-piperidin-1-yl)-7-(3-fluoro-benzyl)-1,3-dimethyl-3,7-dihydro-purine-2,6-dione (44)

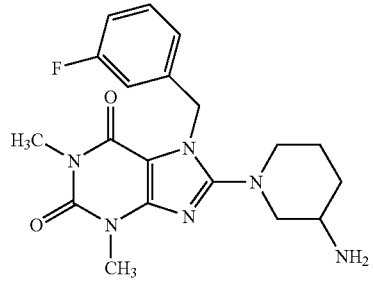

HPLC-MS (Method A3): m/z=387 (M+1), $R_t$=3.10 min.

Example 45

General Procedure (F)

8-(3-Amino-piperidin-1-yl)-1,3-dimethyl-7-(2-methyl-benzyl)-3,7-dihydro-purine-2,6-dione (45)

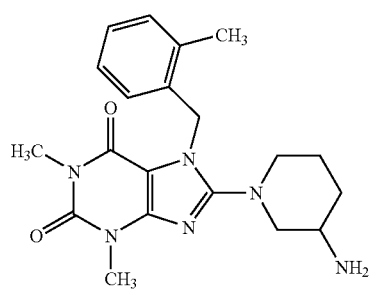

$^1$H NMR (CDCl$_3$): δ=8.1(br. s, 3H), 7.1(m, 3H), 6.6(d, 1H), 5.4(q, 2H), 3.4–3.6(m, 6H), 3.3(s, 3H), 3.05(br. s, 2H), 1.4–2.0(m, 4H). $^{13}$C-NMR (CDCl$_3$) δ=155.60, 154.79, 152.01, 135,10, 134.61, 130.96, 128.06, 126.86, 124.93, 105.83, 75.09, 52.02, 51.24, 50.73, 47.10, 46.72, 30.05, 28.29, 21.12, 19.26. HPLC-MS (Method A3): m/z=383 (M+1), $R_t$=3.20 min.

Example 46

General Procedure (F)

8-(3-Amino-piperidin-1-yl)-7-(3,5-difluoro-benzyl)-1,3-dimethyl-3,7-dihydro-purine-2,6-dione (46)

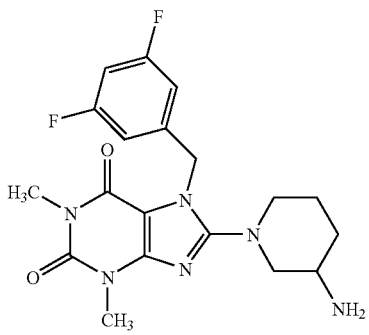

HPLC-MS (Method A3): m/z=405 (M+1), $R_t$=3.10 min.

Example 47

General Procedure (F)

8-(3-Amino-piperidin-1-yl)-7-(2,5-difluoro-benzyl)-1,3-dimethyl-3,7-dihydro-purine-2,6-dione (47)

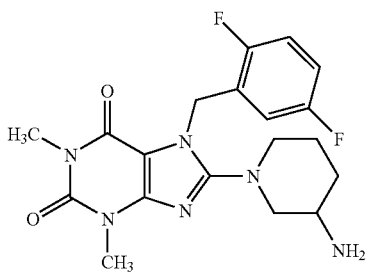

HPLC-MS (Method A3): m/z=405 (M+1), $R_t$=2.80 min.

Example 48

General Procedure (F)

8-(3-Amino-piperidin-1-yl)-7-(2-difluoromethoxy-benzyl)-1,3-dimethyl-3,7-dihydro-purine-2,6-dione (48)

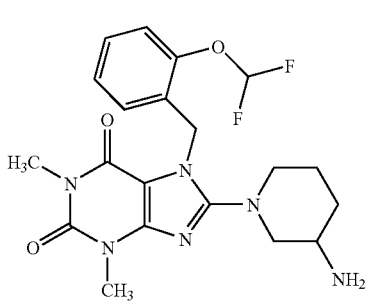

HPLC-MS (Method A3): m/z=435 (M+1), $R_t$=3.10 min.

Example 49

General Procedure (A)

8-(3-Amino-piperidin-1-yl)-7-(2-chloro-benzyl)-3-methyl-1-(2-oxo-2-phenyl-ethyl)-3,7-dihydro-purine-2,6-dione (49)

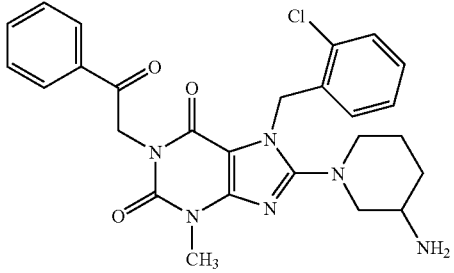

$^1$H NMR (DMSO-$d_6$): δ 8.03 (d, 2H), 7.95 (s br, 3H), 7.70 (t, 1H), 7.56 (t, 2H), 7.49 (m, 1H), 7.31 (m, 2H), 6.88 (d, 1H), 5.39 (s, 2H), 5.30 (s, 2H), 3.63 (d, 1H), 3.25–3.15 (m, 2H), 2.05–1.20 (m, 5H). HPLC-MS (Method C): m/z=507 (M+1), $R_t$=4.68 min.

Example 50

General Procedure (G)

8-(R-3-Amino-piperidin-1-yl)-7-(2-chloro-benzyl)-3-methyl-1-(2-oxo-2-phenyl-ethyl)-3,7-dihydro-purine-2,6-dione (50)

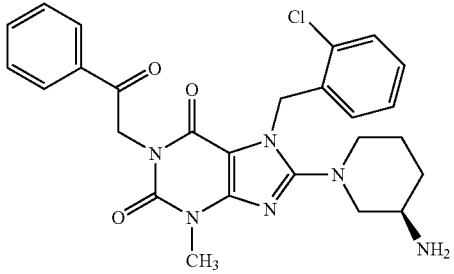

$^1$H NMR (DMSO-$d_6$): δ 8.70 (s, 3H), 8.035 (d, 2H), 7.70 (t, 1H), 7.57 (t, 2H), 7.53–7.45 (m, 1H), 7.38–7.25 (m, 2H), 6.93–6.82 (m, 1H), 5.405 (d, 2H), 5.30 (s, 2H), 6.64 (d, 1H), 3.47 (s, 3H), 3.21–3.06 (m, 3H), 2.94–2.80 (m, 1H), 2.02–1.34 (m, 4H). HPLC-MS (Method B): m/z=507 (M+1), $R_t$=2,868 min.

Example 51

General Procedure (A)

2-[8-(3-Aminopiperidin-1-yl)-7-(2-bromobenzyl)-3-methyl-2,6-dioxo-1,2,3,6-tetrahydropurin-1-ylmethyl]benzonitrile (51)

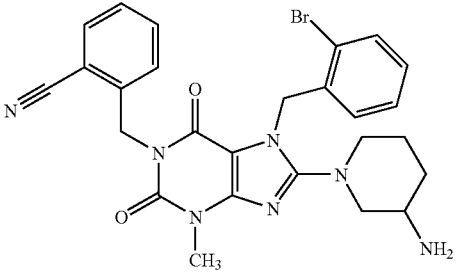

$^1$H NMR (DMSO-$d_6$): δ 7.99 (s br, 3H), 7.80 (d, 1H), 7.67 (d, 1H), 7.58 (t, 1H), 7.42 (t, 1H), 7.34 (t, 1H), 7.25 (t, 1H), 7.16 (d, 1H), 6.87 (d, 1H), 5.34 (s, 2H), 5.15 (s, 2H), 3.62

(m, 1H), 3.40 (m, 2H), 3.45 (s, 3H), 3.20–3.05 (m, 2H), 1.95 (m, 1H), 1.80 (m, 1H), 1.55 (m, 2H).

HPLC-MS (Method C): m/z=548 (M+1), $R_t$=4.68

Example 52

General Procedure (A)

8-(3-Amino-piperidin-1-yl)-7-(2-bromo-benzyl)-3-methyl-1-(2-oxo-2-phenyl-ethyl)-3,7-dihydro-purine-2,6-dione (52)

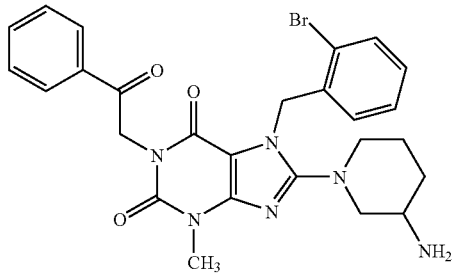

$^1$H NMR (DMSO-d$_6$): δ 8.03 (d, 2H), 7.96 (s br, 3H), 7.72–7.65 (m, 2H), 7.56 (t, 2H), 7.35 (t, 1H), 7.25 (t, 1H), 6.83 (d, 1H), 5.34 (s, 2H), 5.30 (s, 2H), 3.62 (m, 1H), 3.47 (s, 3H), 3.20–3.05 (m, 2H), 1.95 (m, 1H), 1.80 (m, 1H), 1.55 (m, 2H). HPLC-MS (Method C): m/z=551 (M+1), $R_t$=4.80

Example 53

General Procedure (D)

8-(3-Amino-piperidin-1-yl)-3-methyl-1-(2-oxo-2-phenyl-ethyl)-7-(2-trifluoromethyl-benzyl-3,7-dihydro-purine-2,6-dione (53)

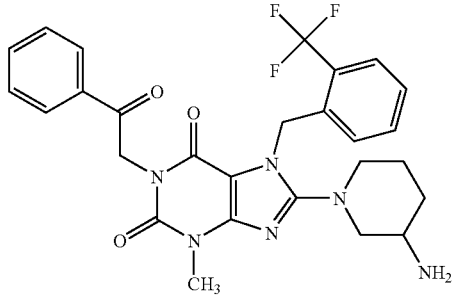

HPLC-MS (Method A3): m/z=541 (M+1), $R_t$=4.30 min.

Example 54

General Procedure (D)

8-(3-Amino-piperidin-1-yl)-1-(2-benzo[b]thiophen-3-yl-2-oxo-ethyl)-7-(2-chloro-benzyl-3-methyl-3,7-dihydro-purine-2,6-dione (54)

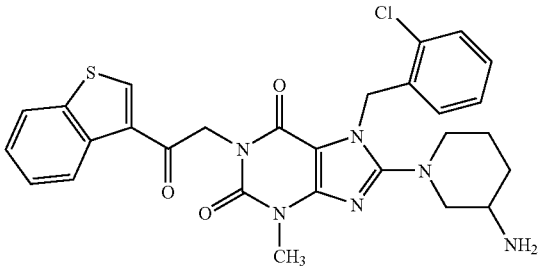

HPLC-MS (Method A3): m/z=564 (M+1), $R_t$=4.60 min.

Example 55

General Procedure (D)

8-(3-Amino-piperidin-1-yl)-7-(2-chloro-benzyl)-1-[2-(3-fluoro-phenyl)-2-oxo-ethyl]3-methyl-3,7-dihydro-purine-2,6-dione (55)

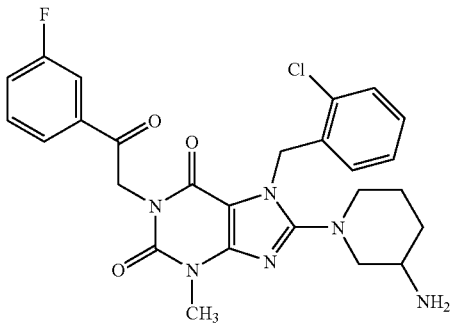

HPLC-MS (Method A3): m/z=525 (M+1), $R_t$=4.10 min.

Example 56

General Procedure (D)

8-(3-Amino-piperidin-1-yl)-7-(2-bromo-benzyl)-1-(2-cyclopropyl-2-oxo-ethyl)-3-methyl-3,7-dihydro-purine-2,6-dione (56)

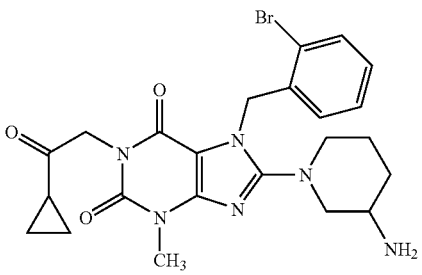

HPLC-MS (Method A3): m/z=516 (M+1), $R_t$=3.40 min.

Example 57

General Procedure (D)

8-(3-Amino-piperidin-1-yl)-7-(2-bromo-benzyl)-1-[2-(2,6-dimethoxy-phenyl)-2-oxo-ethyl]-3-methyl-3,7-dihydro-purine-2,6-dione (57)

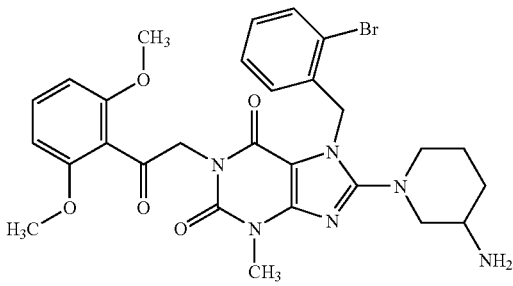

HPLC-MS (Method A3): m/z=612 (M+1), $R_t$=4.20 min.

Example 58

General Procedure (D)

8-(3-Amino-piperidin-1-yl)-7-(2-bromo-benzyl)-3-methyl-1-(2-oxo-2-thiophen-3-yl-ethyl)-3,7-dihydro-purine-2,6-dione (58)

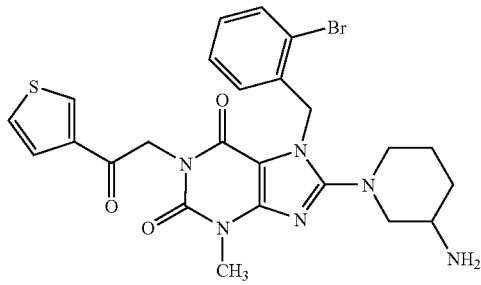

HPLC-MS (Method A3): m/z=558 (M+1), $R_t$=3.90 min.

Example 59

General procedure (D)

8-(3-Amino-piperidin-1-yl)-7-(2-bromo-benzyl)-1-[2-(4-chloro-phenyl)-2-oxo-ethyl]-3-methyl-3,7-dihydro-purine-2,6-dione (59)

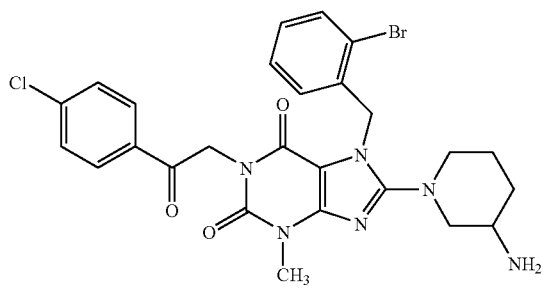

HPLC-MS (Method A3): m/z=586 (M+1), $R_t$=4.50 min.

Example 60

General Procedure (D)

8-(3-Amino-piperidin-1-yl)-7-(2-bromo-benzyl)-3-methyl-1-(2-oxo-2-p-tolyl-ethyl)-3,7-dihydro-purine-2,6-dione (60)

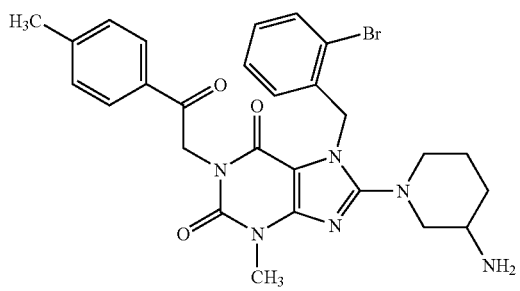

HPLC-MS (Method A3): m/z=566 (M+1), $R_t$=4.40 min.

Example 61

General Procedure (D)

8-(3-Amino-piperidin-1-yl)-7-(2-bromo-benzyl)-1-[2-(2-chloro-phenyl)-2-oxo-ethyl]-3-methyl-3,7-dihydro-purine-2,6-dione (61)

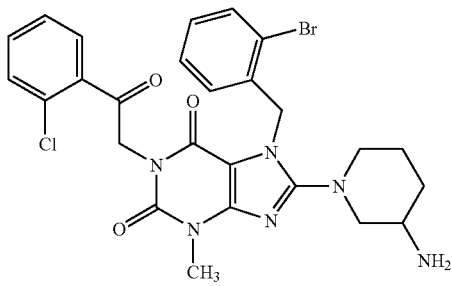

HPLC-MS (Method A3): m/z=586 (M+1), $R_t$=4.30 min.

Example 62

General Procedure (D)

8-(3-Amino-piperidin-1-yl)-7-(2-bromo-benzyl)-1-[2-(3-methoxy-phenyl)-2-oxo-ethyl]-3-methyl-3,7-dihydro-purine-2,6-dione (62)

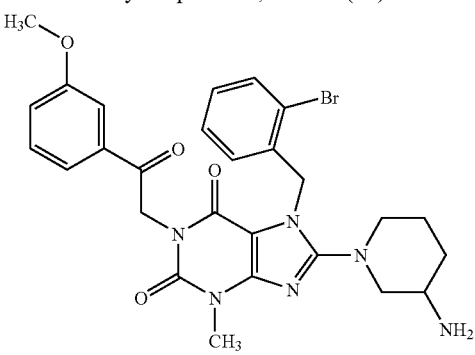

HPLC-MS (Method A3): m/z=582(M+1), $R_t$=4.30 min.

Example 63

General Procedure (D)

8-(3-Amino-piperidin-1-yl)-7-(2-bromo-benzyl)-1-[2-(2-methoxy-phenyl)-2-oxo-ethyl]-3-methyl-3,7-dihydro-purine-2,6-dione (63)

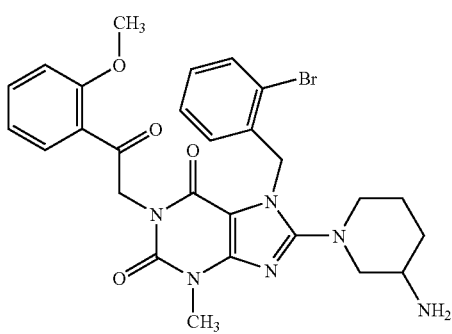

HPLC-MS (Method A3): m/z=582 (M+1), $R_t$=4.20 min.

Example 64

General Procedure (D)

8-(3-Amino-piperidin-1-yl)-7-(2-bromo-benzyl)-3-methyl-1-(2-oxo-butyl)-3,7-dihydro-purine-2,6-dione (64)

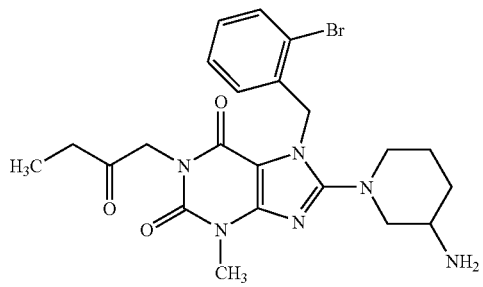

HPLC-MS (Method A3): m/z=504 (M+1), $R_t$=0.90 min.

Example 65

General Procedure (D)

8-(3-Amino-piperidin-1-yl)-7-(2-bromo-benzyl)-3-methyl-1-(2-oxo-1-phenyl-pyrrolidin-3-yl)-3,7-dihydro-purine-2,6-dione (65)

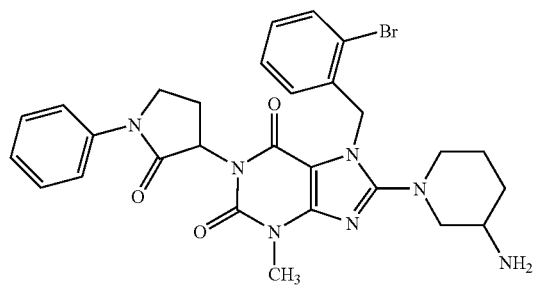

HPLC-MS (Method A3): m/z=593 (M+1), $R_t$=4.00 min.

Example 66

General Procedure (D)

8-(3-Amino-piperidin-1-yl)-7-(2-bromo-benzyl)-1-[2-(3-chloro-phenyl)-2-oxo-ethyl]-3-methyl-3,7-dihydro-purine-2,6-dione (66)

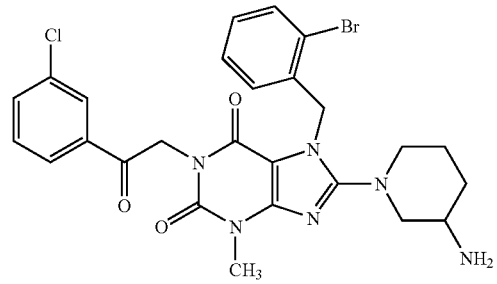

HPLC-MS (Method A3): m/z=586 (M+1), $R_t$=4.60 min.

Example 67

General Procedure (D)

2-{8-(3-Amino-piperidin-1-yl)-1-[2-(2,6-difluoro-phenyl)-2-oxo-ethyl]-3-methyl-2,6-dioxo-1,2,3,6-tetrahydro-purin-7-ylmethyl}-benzonitrile (67)

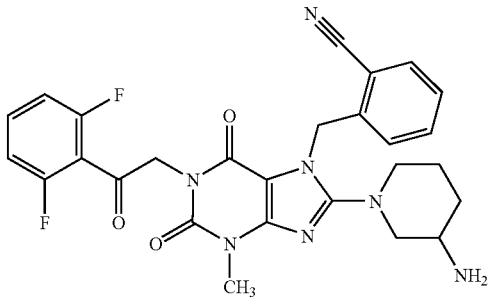

HPLC-MS (Method A3): m/z=534(M+1), $R_t$=3.90 min.

Example 68

General Procedure (D)

2-[8-(3-Amino-piperidin-1-yl)-3-methyl-2,6-dioxo-1-(2-oxo-2-thiophen-3-yl-ethyl)-1,2,3,6-tetrahydro-purin-7-ylmethyl]-benzonitrile (68)

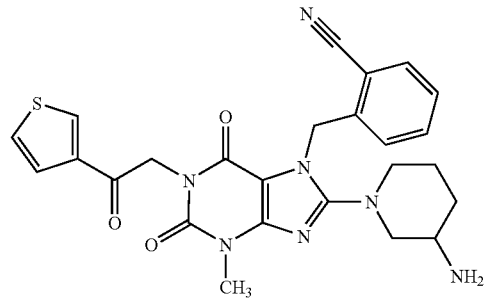

HPLC-MS (Method A3): m/z=504 (M+1), $R_t$=0.90 min.

Example 69

General Procedure (D)

2-[8-(3-Amino-piperidin-1-yl)-1-(2-benzo[b]thiophen-3-yl-2-oxo-ethyl)-3-methyl-2,6,-dioxo-1,2,3,6-tetrahydro-purin-7-ylmethyl]-benzonitrile (69)

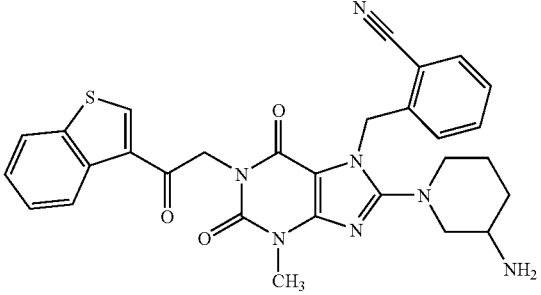

HPLC-MS (Method A3): m/z=554 (M+1), $R_t$=4.30 min.

Example 70

General Procedure (D)

2-[8-(3-Amino-piperidin-1-yl)-3-methyl-2,6-dioxo-1-(2-oxo-2-phenyl-ethyl)-1,2,3,6-tetrahydro-purin-7-ylmethyl]-benzonitrile (70)

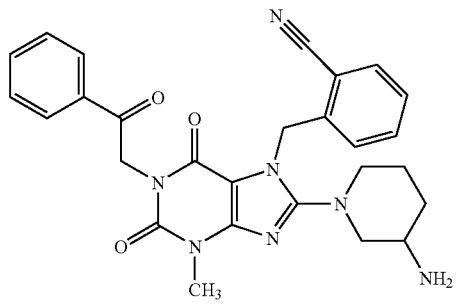

HPLC-MS (Method A3): m/z=498 (M+1), $R_t$=3.60 min.

Example 71

General Procedure (D)

2-{8-(3-Amino-piperidin-1-yl)-1-[2-(3-fluoro-phenyl)-2-oxo-ethyl]-3-methyl-2,6-dioxo-1,2,3,6-tetrahydro-purin-7-ylmethyl}-benzonitrile (71)

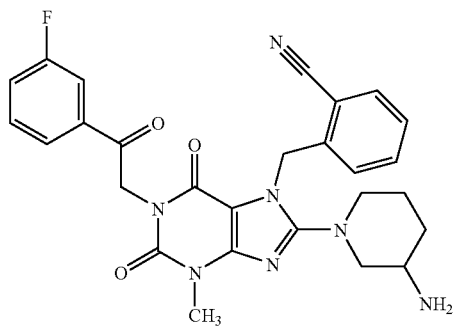

HPLC-MS (Method A3): m/z=516 (M+1), $R_t$=3.80 min.

Example 72

General Procedure (D)

8-(3-Amino-piperidin-1-yl)-3-methyl-1-(2-oxo-2-phenyl-ethyl)-7-(3-trifluoromethoxy-benzyl)-3,7-dihydro-purine-2,6-dione (72)

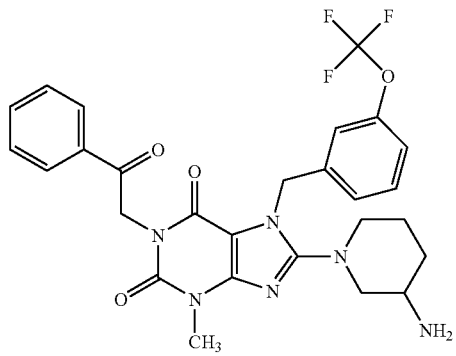

HPLC-MS (Method A3): m/z=557 (M+1), $R_t$=4.50 min.

Example 73

General Procedure (D)

8-(3-Amino-piperidin-1-yl)-7-(2-fluoro-6-trifluoromethyl-benzyl)-3-methyl-1-(2-oxo-2-phenyl-ethyl)-3,7-dihydro-purine-2,6-dione (73)

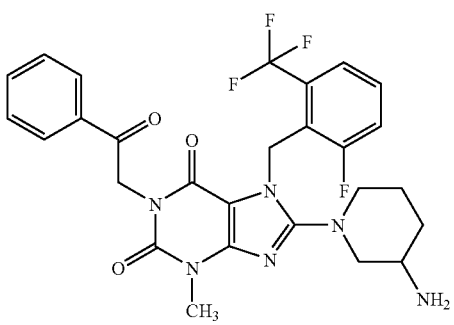

HPLC-MS (Method A3): m/z=559 (M+1), $R_t$=4.10 min.

Example 74

General Procedure (D)

8-(3-Amino-piperidin-1-yl)-7-(2-fluoro-5-trifluoromethyl-benzyl)-3-methyl-1-(2-oxo-2-phenyl-ethyl)-3,7-dihydro-purine-2,6-dione (74)

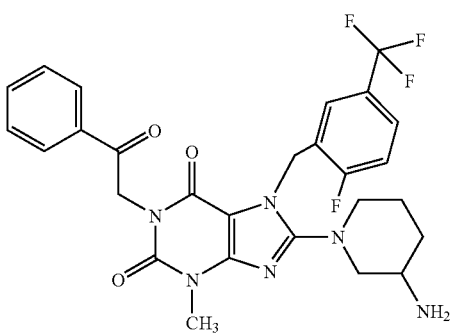

HPLC-MS (Method A3): m/z=559 (M+1), $R_t$=4.30 min.

Example 75

2-(8-(3-Aminoazepan-1-yl)-7-(2-chlorobenzyl)-3-methyl-2,6-dioxo-1,2,3,6-tetrahydropurin-1-ylmethyl)benzonitrile. TFA (75)

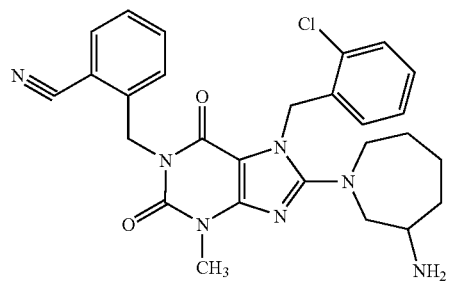

Step A: 8-Bromo-7-(2-chlorobenzyl)-3-methyl-3,7-dihydropurine-2,6-dione. (75A)

8-Bromo-3-methyl-3,7-dihydropurine-2,6-dione and 2-chlorobenzyl bromide were reacted and purified as described in the General procedure G, step A, to afford compound (75A).

HPLC-MS (Method B): m/z=371 (M+1), Rt 3.031 min.

Step B: 2-(8-Bromo-7-(2-chlorobenzyl)-3-methyl-2,6-dioxo-1,2,3,6-tetrahydropurin-1-ylmethyl)benzonitrile (75B)

8-Bromo-7-(2-chlorobenzyl)-3-methyl-3,7-dihydropurine-2,6-dione (75A) and alpha-bromo-o-tolunitril were reacted and purified as described in the General procedure G, Step B, to afford 75B as white crystals.

Yield: 1.66 g (85%).

HPLC-MS (Method B): m/z=486 (M+1), Rt=4.733 min.

Step C: 2-(8-(3-Aminoazepan-1-yl)-7-(2-chlorobenzyl)-3-methyl-2,6-dioxo-1,2,3,6-tetrahydropurin-1-ylmethyl)benzonitrile. TFA (75)

2-(8-Bromo-7-(2-chlorobenzyl)-3-methyl-2,6-dioxo-1,2,3,6-tetrahydropurin-1-ylmethyl)benzonitrile (75B) (250 mg, 0.5 mmol) and azepan-3-ylamine (294 mg, 2.5 mmol), and triethylamine (0.35 ml, 2.5 mmol) were dissolved in 20 ml of DMSO and the mixture was subjected to microwaves (method F, 100° C., 300 W) for five hours. To the reaction mixture was added 100 ml of water and 100 ml of dichloromethane, and the organic layer was separated and dried over sodium sulfate. The solvents were evaporated and the crude product was purified by preparative HPLC (method A1, $R_t$=8.77 min.). Evaporation of the solvent afforded the title compound as an yellow oil.

Yield: 166 mg (51%).

HPLC-MS (Method B): m/z=518 (M+), $R_t$=3.09 min.

Example 76

8-(3-Aminoazepan-1-yl)-7-(2-chlorobenzyl)-3-methyl-3,7-dihydropurine-2,6-dione.

TFA (76)

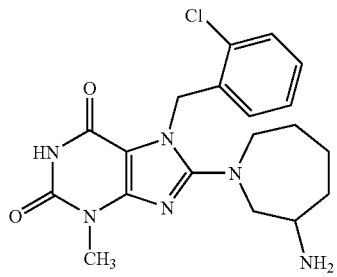

8-Bromo-7-(2-chlorobenzyl)-3-methyl-3,7-dihydropurine-2,6-dione (75A) (185 mg, 0.5 mmol) and azepan-3-ylamine (513 mg, 4.5 mmol), and triethylamine (0.35 ml, 2.5 mmol) were dissolved in 20 ml of DMSO and the mixture was subjected to microwaves (method F, 100° C., 300 W) for four hours. To the reaction mixture was added 100 ml of water and 100 ml of dichloromethane, and the organic layer was separated and dried over magnesium sulfate. The solvents were evaporated and the crude product was purified by preparative HPLC (method A1, $R_t$=7.12 min.). Evaporation of the solvent afforded the title compound as an yellow oil.

Yield: 110 mg (43%).

HPLC-MS (Method B): m/z=403 (M+1), $R_t$=1.87 min.

Example 77

8-(3-Aminoazepan-1-yl)-7-benzyl-3-methyl-1-(2-oxo-2-phenylethyl)-3,7-dihydropurine-2,6-dione

TFA (77)

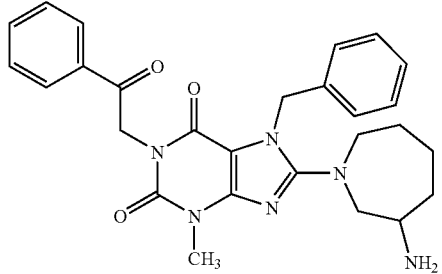

Step A: 7-Benzyl-8-bromo-3-methyl-3,7-dihydropurine-2,6-dione (77A)

8-Bromo-3-methyl-3,7-dihydropurine-2,6-dione and benzyl bromide were reacted and purified as described in the General procedure G, step A, to afford 77A.

HPLC-MS (Method B): m/z=335 (M+)

Step B: 7-Benzyl-8-bromo-3-methyl-1-(2-oxo-2-phenylethyl)-3,7-dihydropurine-2,6-dione (77B)

7-Benzyl-8-bromo-3-methyl-3,7-dihydropurine-2,6-dione (77A) and 2-bromoacetophenone were reacted and purified as described in the General procedure G, Step B, to afford 77B.

HPLC-MS (Method B): m/z=453 (M+).

Step C: 8-(3-Aminoazepan-1-yl)-7-benzyl-3-methyl-1-(2-oxo-2-phenylethyl)-3,7-dihydropurine-2,6-dione. TFA (77)

7-Benzyl-8-bromo-3-methyl-1-(2-oxo-2-phenylethyl)-3,7-dihydropurine-2,6-dione (77B) (227 mg, 0.5 mmol) and azepan-3-ylamine (342 mg, 3 mmol), and triethylamine (0.35 ml, 2.5 mmol) were dissolved in 20 ml of DMSO and the mixture was subjected to microwaves (method F, 100° C., 300 W) for five hours. To the reaction mixture was added 100 ml of water and 100 ml of dichloromethane, and the organic layer was separated and dried over sodium sulfate. The solvents were evaporated and the crude product was purified by preparative HPLC (method A1, $R_t$=8.77 min.). Evaporation of the solvent afforded the title compound as an yellow oil.

Yield: 130 mg (43%).

HPLC-MS (Method B): m/z=487 (M+1), $R_t$=2.97 min.

Example 78

8-(3-Aminoazepan-1-yl)-7-benzyl-3-methyl-3,7-dihydropurine-2,6-dione

TFA (78)

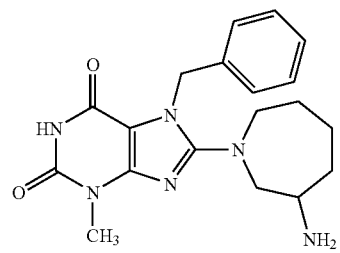

7-Benzyl-8-bromo-3-methyl-3,7-dihydropurine-2,6-dione (77A) (300 mg, 0.9 mmol) and azepan-3-ylamine (307 mg, 2.7 mmol), and triethylamine (0.62 ml, 4.5 mmol) were dissolved in NMP (3 ml) and the mixture was subjected to microwaves (method F, 200° C., 300 W) for 30 minutes. To the reaction mixture was added 100 ml of water and 100 ml of dichloromethane, and the organic layer was washed with 1N NaOH, and dried over magnesium sulfate. The solvents were evaporated and the crude product was purified by preparative HPLC (method A1, Rt=6.53 min.). Evaporation of the solvent afforded the title compound as an brown oil.

Yield: 30 mg (7%).

HPLC-MS (Method B): m/z=369 (M+1), $R_t$=1.53 min.

Example 79

2-(8-(3-Aminoazepan-1-yl)-3-methyl-2,6-dioxo-1,2,3,6-tetrahydropurin-7-ylmethyl)benzonitrile TFA (79)

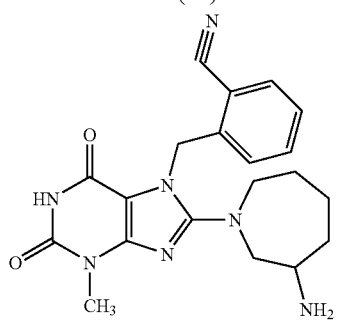

Step A: 2-(8-Bromo-3-methyl-2,6-dioxo-1,2,3,6-tetrahydropurin-7-ylmethyl)benzonitrile. (79A)

8-Bromo-3-methyl-3,7-dihydropurine-2,6-dione and alpha-bromo-o-tolunitrile were reacted and purified as described in the General procedure G, step A, to afford 79A as white crystals in 91% yield.

HPLC-MS (Method B): m/z=360 (M+1), Rt=2.54 min.

Step B: 2-(8-(3-Aminoazepan-1-yl)-3-methyl-2,6-dioxo-1,2,3,6-tetrahydropurin-7-ylmethyl)benzonitrile. TFA (79)

2-(8-Bromo-3-methyl-2,6-dioxo-1,2,3,6-tetrahydropurin-7-ylmethyl)benzonitrile (79A) (181 mg, 0,5 mmol) and azepan-3-ylamine (342 mg, 3 mmol), and triethylamine (0.35 ml, 2.5 mmol) were dissolved in 20 ml of DMSO and the mixture was subjected to microwaves (method F, 100° C., 300 W) for four hours. To the reaction mixture was added 100 ml of water and 100 ml of dichloromethane, and the organic layer was separated and dried over sodium sulfate. The solvents were evaporated and the crude product was purified by preparative HPLC (method A1, Rt=6.22 min.). Evaporation of the solvent afforded the title compound as an yellow oil.

Yield: 142 mg (56%).

HPLC-MS (Method B): m/z=394 (M+1), $R_t$=1.41 min.

Example 80

8-(3-Aminoazepan-1-yl)-7-(2-bromobenzyl)-3-methyl-3,7-dihydropurine-2,6-dione TFA (80)

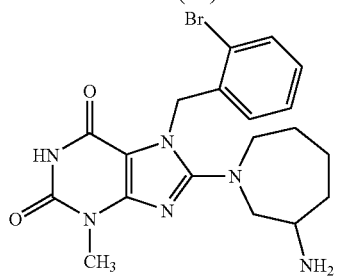

Step A: 8-Bromo-7-(2-bromobenzyl)-3-methyl-3,7-dihydropurine-2,6-dione (80A)

8-Bromo-3-methyl-3,7-dihydropurine-2,6-dione and 2-bromobenzyl bromide were reacted and purified as described in the General procedure G, step A, to afford 80A.

HPLC-MS (Method B): m/z=414 (M+), Rt=3.285 min.

Step B: 8-(3-Aminoazepan-1-yl)-7-(2-bromobenzyl)-3-methyl-3,7-dihydropurine-2,6-dione. TFA (80)

8-Bromo-7-(2-bromobenzyl)-3-methyl-3,7-dihydropurine-2,6-dione (80A) (300 mg, 0,7 mmol) and azepan-3-ylamine (248 mg, 2,2 mmol), and triethylamine (0.5 ml, 3,6 mmol) were dissolved in 3 ml of DMSO and the mixture was subjected to microwaves (method F, 200° C., 300 W) for 30 minutes. To the reaction mixture was added 100 ml of water and 100 ml of dichloromethane, and the organic layer was separated and dried over sodium sulfate. The solvents were evaporated and the crude product was purified by preparative HPLC (method A1, Rt=7.17 min.). Evaporation of the solvent afforded the title compound as an brown oil.

Yield: 138 mg (34%).

HPLC-MS (Method B): m/z=447 (M+), $R_t$=1.82 min.

Example 81

8-(3-Aminoazepan-1-yl)-3-methyl-7-(2-trifluoromethylbenzyl)-3,7-dihydropurine-2,6-dione TFA (81)

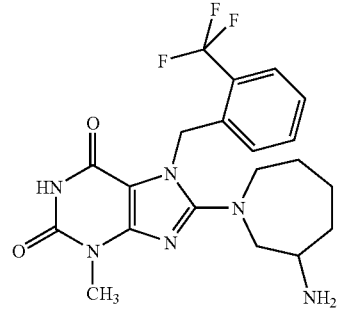

Step A: 8-Bromo-3-methyl-7-(2-trifluoromethylbenzyl)-3,7-dihydropurine-2,6-dione (81A)

8-Bromo-3-methyl-3,7-dihydropurine-2,6-dione and 2-(trifluoromethyl)benzyl bromide were reacted and purified as described in the General procedure G, step A, to afford 81A as white crystals in 69% yield.

HPLC-MS (Method B): m/z=403 (M+), Rt=3.54 min.

Step B: 8-(3-Aminoazepan-1-yl)-3-methyl-7-(2-trifluoromethylbenzyl)-3,7-dihydropurine-2,6-dione TFA (81)

8-Bromo-3-methyl-7-(2-trifluoromethylbenzyl)-3,7-dihydropurine-2,6-dione (81A) (300 mg, 0.7 mmol) and azepan-3-ylamine (255 mg, 2,2 mmol), and triethylamine (0.5 ml, 3.7 mmol) were dissolved in 3 ml of DMSO and the mixture was subjected to microwaves (method F, 200° C., 300 W) for 10 minutes. To the reaction mixture was added 100 ml of water and 100 ml of dichloromethane, and the organic layer was washed with 1N NaOH, and dried over sodium sulfate. The solvents were evaporated and the crude product was purified by preparative HPLC (method A1, Rt=7.42 min.). Evaporation of the solvent afforded the title compound as a brown oil.

Yield: 96 mg (23%).

HPLC-MS (Method B): m/z=437 (M+1), $R_t$=2.30 min.

Example 82

8-(3-Aminoazepan-1-yl)-3-methyl-7-(2-methylbenzyl)-3,7-dihydropurine-2,6-dione

TFA (82)

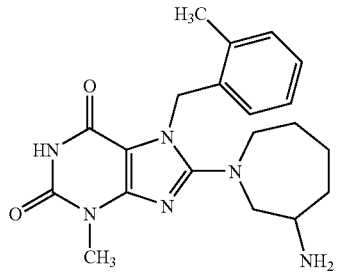

Step A: 8-Bromo-3-methyl-7-(2-methylbenzyl)-3,7-dihydropurine-2,6-dione (82A)

8-Bromo-3-methyl-3,7-dihydropurine-2,6-dione and 2-methylbenzyl bromide were reacted and purified as described in the General procedure G, step A, to afford 82A as white crystals in 79%.

HPLC-MS (Method B): m/z=351 (M+2), Rt=3.14 min.

Step B: 8-(3-Aminoazepan-1-yl)-3-methyl-7-(2-methylbenzyl)-3,7-dihydropurine-2,6-dione. TFA (82)

8-Bromo-3-methyl-7-(2-methylbenzyl)-3,7-dihydropurine-2,6-dione (82A) (300 mg, 0,86 mmol) and azepan-3-ylamine (294 mg, 2,6 mmol), and triethylamine (0.6 ml, 4.3 mmol) were dissolved in 3 ml of DMSO and the mixture was subjected to microwaves (method F, 200° C., 300 W) for 3 minutes. To the reaction mixture was added 100 ml of water and 100 ml of dichloromethane, and the organic layer was washed with 1N NaOH, and dried over sodium sulfate. The solvents were evaporated and the crude product was purified by preparative HPLC (method A1, Rt=6.93 min.). Evaporation of the solvent afforded the title compound as yellow crystals.

Yield: 201 mg (47%).

HPLC-MS (Method B): m/z=383 (M+1), $R_f$=2.06 min.

Example 83

8-(3-Aminoazepan-1-yl)-7-(2-bromobenzyl)-1,3-dimethyl-3,7-dihydropurine-2,6-dione

TFA (83)

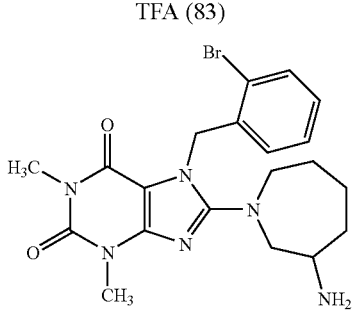

Step A: 7-(2-Bromobenzyl)-8-chloro-1,3-dimethyl-3.7-dihydropurine-2,6-dione (83A)

8-Chlorotheophylline and 2-bromobenzyl bromide were reacted and purified as described in the General procedure CC, step A, to afford 83A as white crystals in 57%.

HPLC-MS (Method B): m/z=385 (M+2), Rt=3.77 min.

Step B: 8-(3-Aminoazepan-1-yl)-7-(2-bromobenzyl)-1,3-dimethyl-3,7-dihydropurine-2,6-dione TFA (83)

7-(2-Bromobenzyl)-8-chloro-1,3-dimethyl-3,7-dihydropurine-2,6-dione (83A) (300 mg, 0.8 mmol) and azepan-3-ylamine (268 mg, 2.3 mmol), and triethylamine (0.5 ml, 3.9 mmol) were dissolved in 3 ml of DMSO and the mixture was subjected to microwaves (method F, 200° C., 300 W) for 15 minutes. To the reaction mixture was added 100 ml of water and 100 ml of dichloromethane, and the organic layer was washed with 1N NaOH, and dried over sodium sulfate. The solvents were evaporated and the crude product was purified by preparative HPLC (method A1, $R_f$=7.76 min.). Evaporation of the solvent afforded the title compound as a brown oil.

Yield: 243 mg (54%).

HPLC-MS (Method B): m/z=461 (M+), $R_f$=2.32 min.

Example 84

2-[8-(3-Aminoazepan-1-yl)-1,3-dimethyl-2,6-dioxo-1,2,3,6-tetrahydropurin-7-ylmethyl]benzonitrile

TFA (84)

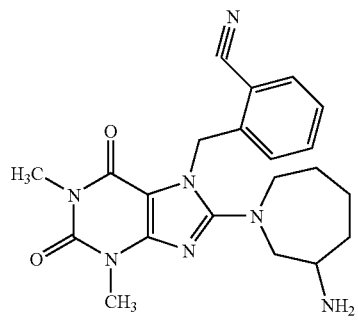

Step A: 7-(2-Bromobenzyl)-8-chloro-1,3-dimethyl-3.7-dihydropurine-2,6-dione (84A)

8-Chlorotheophylline and alpha-bromo-o-tolunitrile were reacted and purified as described in the General procedure C, step A, to afford (84A) as white crystals in 66%.

HPLC-MS (Method B): m/z=330 (M+1), Rt=2.93 min.

Step B: 2-[8-(3-Aminoazepan-1-yl)-1,3-dimethyl-2,6-dioxo-1,2,3,6-tetrahydropurin-7-ylmethyl]benzonitrile TFA (84)

7-(2-Bromobenzyl)-8-chloro-1,3-dimethyl-3,7-dihydropurine-2,6-dione (84A) (300 mg, 0.9 mmol) and azepan-3-ylamine (312 mg, 2.7 mmol), and triethylamine (0.6 ml, 4.6 mmol) were dissolved in 3 ml of DMSO and the mixture was subjected to microwaves (method F, 200° C., 300 W) for 30 minutes. To the reaction mixture was added 100 ml of water and 100 ml of dichloromethane, and the organic layer was washed with 1N NaOH, and dried over sodium sulfate. The solvents were evaporated and the crude product was purified by preparative HPLC (method A1, Rt=6.76 min.). Evaporation of the solvent afforded the title compound as a brown oil.

Yield: 268 mg (56%).

HPLC-MS (Method B): m/z=408 (M+1), $R_f$=1.95 min.

Example 85

8-(3-Aminoazepan-1-yl)-1,3-dimethyl-7-(2-methyl-benzyl)-3,7-dihydropurine-2,6-dione

TFA (85)

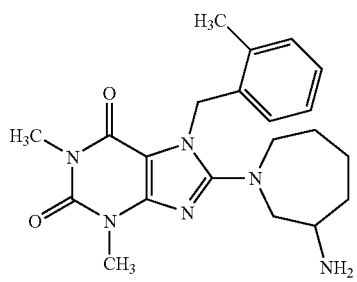

Step A: 8-Chloro-1,3-dimethyl-7-(2-methylbenzyl)-3,7-dihydropurine-2,6-dione (85A)

8-Chlorotheophylline and 2-methylbenzyl bromide were reacted and purified as described in the General procedure C, step A, to afford 85A as white crystals in 86%.

HPLC-MS (Method B): m/z=319 (M+1), Rt=3.76

Step B: 8-(3-Aminoazepan-1-yl)-1,3-dimethyl-7-(2-methylbenzyl)-3,7-dihydropurine-2,6-dione. TFA (85)

8-Chloro-1,3-dimethyl-7-(2-methylbenzyl)-3,7-dihydropurine-2,6-dione (85A) (300 mg, 0.9 mmol) and azepan-3-ylamine (322 mg, 2.8 mmol), and triethylamine (0.7 ml, 4.7 mmol) were dissolved in 3 ml of DMSO and the mixture was subjected to microwaves (method F, 200° C., 300 W) for 10 minutes. To the reaction mixture was added 100 ml of water and 100 ml of dichloromethane, and the organic layer was washed with 1N NaOH, and dried over sodium sulfate. The solvents were evaporated and the crude product was purified by preparative HPLC (method A1, Rt=7.5 min.). Evaporation of the solvent afforded the title compound as a brown oil.

Yield: 312 mg (65%).

HPLC-MS (Method B): m/z=397 (M+1), $R_t$=2.04 min.

Example 86

8-(3-Amino-azepan-1-yl)-7-(2-chloro-benzyl)-1,3-dimethyl-3,7-dihydro-purine-2,6-dione, TFA (86)

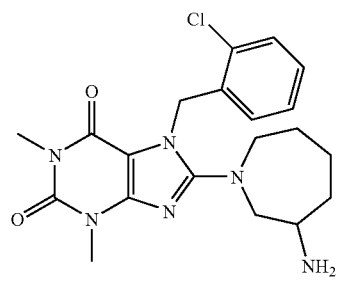

8-Chloro-7-(2-chloro-benzyl)-1,3-dimethyl-3,7-dihydro-purine-2,6-dione (0.34 g, 1 mmol), azepan-3-ylamine (0.34 g, 3 mmol), TEA (0.51 g, 5 mmol) were mixed in 2-propanol (20 ml) and the mixture was subjected to microwaves (method F, 120° C.) for 4 hours. The reaction mixture was evaporated and purified twice by preparative HPLC (method A1) to give the title compound as white crystals.

Yield: 340 mg (64%).

$^1$H-NMR (DMSO-$d_6$, 300 MHz) δ: 9.3 (br s, 1H), 8.6 (br s, 2H), 7.4 (m, 1H), 7.2 (m, 2H), 6.9 (m, 1H), 5.5 (q, 2H), 3.9 (m, 1H), 3.55–3.75 (m, 3H), 3.45 (s, 3H), 3.3 (s, 3H), 2.9 (m, 1H), 2.25 (m, 1H), 1.85 (m, 1H), 1.6 (m, 2H), 1.3 (m, 2H).

$^{13}$C-NMR(CDCl$_3$)δ: 155.04, 154.42, 151.73, 133.87, 131.98, 130.07, 129.56, 127.80, 126.81, 105.51, 55.15, 54.18, 51.70, 48.11, 31.18, 30.79, 30.07, 28.25, 22.42.

Example 87

General Procedure (H)

(R) 2-[8-(3-Amino-piperidin-1-yl)-7-(2-chloro-benzyl)-3-methyl-2,6-dioxo-2,3,6,7-tetrahydro-purin-1-yl]-N-pyridin-2-yl-acetamide

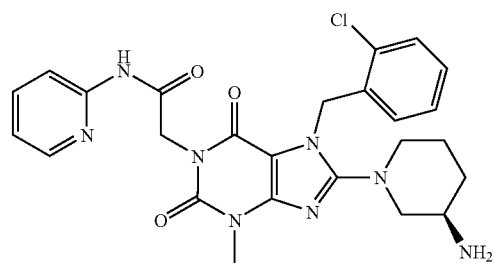

$^1$H-NMR (DMSO-$d_6$, 300 MHz) δ: 10.80 (s, 1H), 8.32(s, 1H), 7.95(s, 4H), 7.75(s, 1H), 7.51(s 1H), 7.31(s, 2H), 7.10(s, 1H), 6.87(s, 1H), 5.40(s, 2H), 4.65(s, 2H), 3.61(s, 1H), 3.45(s, 3H), 3.31(s, 1H), 3.13(s, 2H), 2.87(s, 1H), 2.43(s, 1H), 1.93(s, 1H), 1.73(s, 1H), 1.50(s, 2H). HPLC-MS (Method B): m/z=535 (M+1), Rt=2.059 min.

Example 88

General Procedure (H)

(R) 2-[8-(3-Amino-piperidin-1-yl)-7-(2-chloro-benzyl)-3-methyl-2,6-dioxo-2,3,6,7-tetrahydro-purin-1-yl]-N-cyclohexyl-acetamide

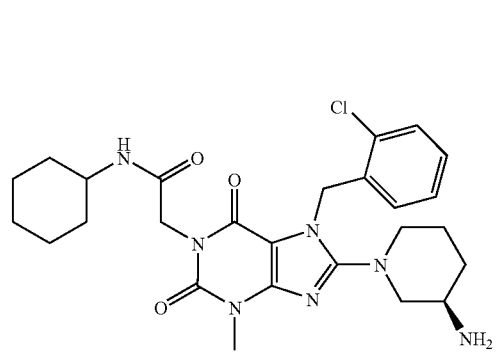

¹H-NMR (DMSO-d₆, 400 MHz) δ: 7.95 (br, 3H), 7.83 (d, 1H), 7.51 (m, 1H), 7.24–7.37 (m, 1H), 6.86 (d, 1H), 5.39 (s, 2H), 4.33 (s, 2H), 3.59 (d, 1H), 3.47 (s, 3H), 3.31–3.40 (m, 3H), 1.89–1.97 (m, 1H), 1.59–1.79 (m, 2.5H), 1.42–1.59 (m, 2.5H), 1.04–1.30 (m, 6H)

Example 89

General Procedure (H)

(R) 8-(3-Amino-piperidin-1-yl)-7-(2-chloro-benzyl)-3-methyl-1-(2-oxo-2-pyrrolidin-1-yl-ethyl)-3,7-dihydro-purine-2,6-dione

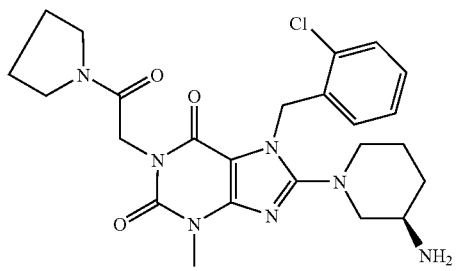

¹H-NMR (DMSO-d₆, 400 MHz) δ: 7.95 (br, 3H), 7.50 (d, 1H), 7.31 (m, 2H), 6.83 (d, 1H), 5.38 (s, 2H), 4.50 (s, 2H), 3.59 (d, 1H), 3.42–3.50 (m, 4H), 3.31–3.42 (br, 2H), 3.30 (s, 1H), 3.22–3.28 (m, 1H), 3.08–3.18 (m, 2H), 2.99 (s, 1H), 2.83–2.92 (m, 1H), 1.85–1.97 (m, 2.5H), 1.70–1.81 (m, 2.5H), 1.43–1.58 (m, 2H)

Example 90

General Procedure (H)

(R) 2-[8-(3-Aminopiperidin-1-yl)-7-(2-chlorobenzyl)-3-methyl-2,6-dioxo-2,3,6,7-tetrahydro-purin-1-yl]-N-cyclopentylacetamide

TFA

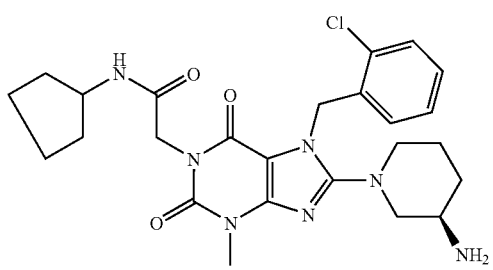

¹H-NMR (DMSO-d₆, 400 MHz) δ: 7.96 (s, 4H), 7.52 (d, 1H), 7.25–7.38 (m, 2H), 6.38 (d, 1H), 5.40 (s, 2H), 4.33 (s, 2H), 3.92 (q, 1H), 3.42 (s, 3H), 3.25–3.37 (m, 1H), 3.05–3.17 (m, 2H), 2.85 (t, 1H), 1.88–1.96 (m, 1H), 1.70–1.81 (m, 4H), 1.56–1.70 (m, 3H), 1.42–1.55 (m, 5H), 1.30–1.40 (m, 3H).

Example 91

General Procedure (H)

2-[8-(3-(R) Amino-piperidin-1-yl)-7-(2-chloro-benzyl)-3-methyl-2,6-dioxo-2,3,6,7-tetrahydro-purin-1-yl]-N-(1-aza-bicyclo[2.2.2]oct-3-yl)-acetamide

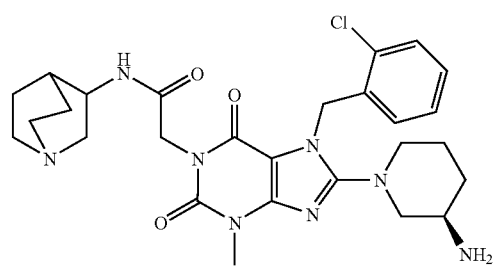

¹H-NMR (DMSO-d₆, 400 MHz) δ: 9.50 (s, 1H), 8.41 (d, 1H), 7.99 (br, 3H), 7.50 (d, 1H), 7.23–7.39 (m, 2H), 6.83 (d, 1H), 5.41 (s, 2H), 4.43 (dd, 2H), 4.03 (m, 1H), 3.54–3.64 (m, 1H), 3.31–3.51 (br, 6H), 3.31 (s, 1H), 3.05–3.25 (m, 4H), 2.98 (s, 1H), 2.81–2.93 (m, 1H), 1.62–2.10 (m, 6H), 1.41–1.58 (m, 2H), 1.13–1.27 (m, 1H)

Example 92

General Procedure (H)

(R) 2-[8-(3-Amino-piperidin-1-yl)-7-(2-chloro-benzyl)-3-methyl-2,6-dioxo-2,3,6,7-tetrahydro-purin-1-yl]-N-(3-hydroxy-pyridin-2-yl)-acetamide

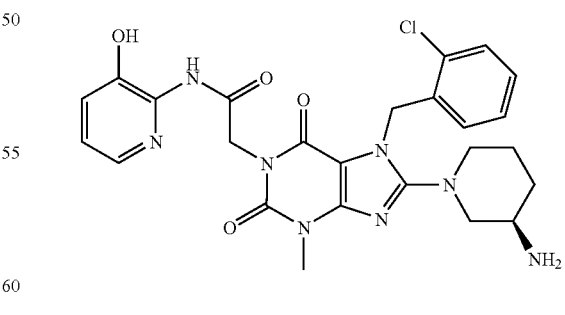

¹H-NMR (MeOD, 300 MHz) δ: 7.865 (d, 1H), 7.505 (d, 1H), 7.40–7.22 (m, 3H), 7.16–7.08 (m, 1H), 6.91–6.84 (m, 1H), 5.40 (s, 2H), 4.75 (s, 2H), 6.65–3.54 (m, 1H), 3.45 (s, 3H), 3.18–3.04 (m, 3H), 2.92–2.79 (m, 1H), 1.97–1.86 (m, 1H), 1.82–1.65 (m, 1H), 1.60–1.40 (m, 2H).

HPLC-MS (Method B): m/z=539 (M+1) Rt=1.836 min.:

Example 93

General Procedure (H)

(R,R) 8-(3-Amino-piperidin-1-yl)-7-(2-chloro-benzyl)-1-[2-(3-hydroxy-pyrrolidin-1-yl)-2-oxo-ethyl]-3-methyl-3,7-dihydro-purine-2,6-dione

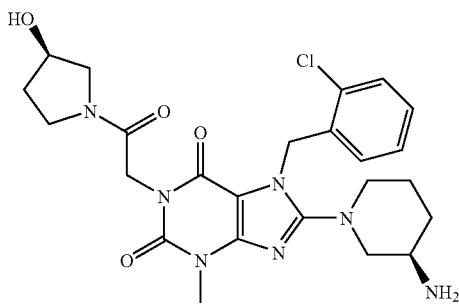

$^1$H-NMR (DMSO-$d_6$, 400 MHz) δ: 7,95 (br, 3H), 7.50 (d, 1H), 7.25–7.38 (m, 2H), 6.84 (d, 1H), 5.38 (s, 2H), 4.39–4.62 (m, 2H), 4.51 (s, 0.5H), 4.25 (s, 0.5H), 3.49–3.65 (m, 2H), 3.45 (s, 3H), 3.07–3.31 (m, 3H), 2.99 (s, 1H), 2.83–2.92 (m, 1H), 1.69–2.01 (m, 3H), 1.43–1.58 (m, 2H)

Example 94

General Procedure (H)

(R) 2-[8-(3-Amino-piperidin-1-yl)-7-benzyl-3-methyl-2,6-dioxo-2,3,6,7-tetrahydro-purin-1-yl]-N-pyridin-2-yl-acetamide

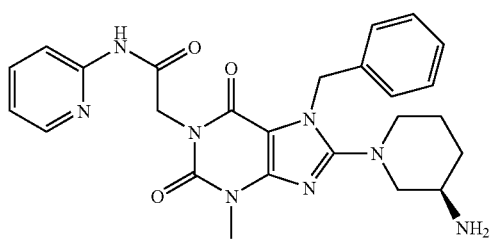

$^1$H-NMR (DMSO-$d_6$, 400 MHz) δ: 10.77 (s, 1H), 8.32 (s, 1H), 7.95 (br, 3H), 7.71–7.85 (m, 1H), 7.23–7.39 (m, 4H), 7.13–7.23 (m, 2H), 7.06–7.13 (m, 1H), 5.37 (s, 2H), 4.70 (s, 2H), 3.54–3.65 (m, 1H), 3.12–3.26 (m, 1H), 3.02–3.12 (m, 1H), 2.98 (s, 1H), 2.80–2.95 (m, 1H), 1.90–2.00 (m, 1H), 1.70–1.82 (m, 1H), 1.45–1.61 (m, 2H)

Example 95

General Procedure (H)

(R) 2-[8-(3-Amino-piperidin-1-yl)-7-benzyl-3-methyl-2,6-dioxo-2,3,6,7-tetrahydro-purin-1-yl]-N-cyclohexyl-acetamide $^1$H-NMR (DMSO-$d_6$, 400 MHz) δ: 7.96 (s, 3H), 7.85 (d, 1H), 7.24–7.40 (m, 3H), 7.18 (d, 2H), 5.36 (s, 2H), 4.37 (s, 2H), 3.53–3.62 (m, 1H), 3.40 (s, 3H), 3.11–3.24 (m, 1H), 3.00–3.11 (m, 1H), 2.97 (s, 1H), 2.79 (m, 1H), 1.89–2.01 (m, 1H), 1.61–1.82 (m, 5H), 1.44–1.61 (m, 3H), 1.05–1.31 (m, 6H)

Example 96

General Procedure (H)

(R) 2-[8-(3-Amino-piperidin-1-yl)-7-benzyl-3-methyl-2,6-dioxo-2,3,6,7-tetrahydro-purin-1-yl]-N-cyclopentyl-acetamide $^1$H-NMR (DMSO-$d_6$, 400 MHz) δ: 7.87–8.03 (m, 4H), 7.24–7.39 (m, 3H), 7.18 (d, 2H), 5.37 (s, 2H), 4.37 (s, 2H), 3.91–4.00 (m, 1H), 3.57 (d, 1H), 3.40 (s, 3H), 3.12–3.23 (m, 1H), 3.01–3.10 (m, 1H), 2.99 (s, 1H), 2.79–2.88 (m, 1H), 1.90–2.01 (m, 1H), 1.70–1.84 (m, 2H), 1.56–1.70 (m, 2H), 1.42–1.56 (m, 4H), 1.30–1.42 (m, 2H).

Example 97

General Procedure (H)

2-[8-(3-(R)-Amino-piperidin-1-yl)-7-benzyl-3-methyl-2,6-dioxo-2,3,6,7-tetrahydro-purin-1-yl]-N-(1-aza-bicyclo[2.2.2]oct-3-yl)-acetamide

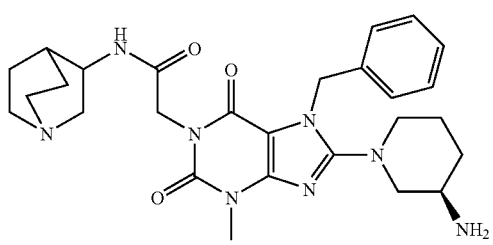

$^1$H-NMR (DMSO-d$_6$, 400 MHz) δ: 9.48 (br, 1H), 8.43 (d, 1H), 7.98 (br, 3H), 7.24–7.38 (m, 3H), 7.17 (d, 2H), 5.36 (s, 2H), 4.47 (dd, 2H), 4.05 (br, 1H), 3.54–3.66 (m, 2H), 3.40 (s, 3H), 3.11–3.26 (m, 4H), 3.00–3.11 (m, 1H), 2.99 (s, 1H), 2.88–2.97 (m, 1H), 2.79–2.88 (m, 1H), 1.91–2.08 (m, 3H), 1.64–1.91 (m, 3H), 1.45 (m, 2H)

Example 98

General Procedure (H)

(R) 2-[8-(3-Amino-piperidin-1-yl)-7-benzyl-3-methyl-2,6-dioxo-2,3,6,7-tetrahydro-purin-1-yl]-N-(3-hydroxy-pyridin-2-yl)-acetamide

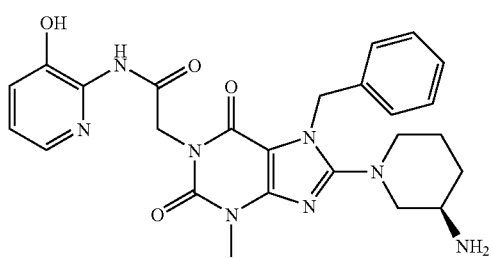

$^1$H-NMR (DMSO-d$_6$, 400 MHz) δ: 7.76 (br, 3H), 7.89 (d, 1H), 7.24–7.40 (m, 5H), 7.13–7.24 (m, 3H), 5.38 (s, 2H), 4.82 (s, 2H), 3.56–3.65 (m, 1H), 3.40 (s, 3H), 3.14–3.23 (m, 1H), 3.02–3.11 (m, 1H), 2.99 (s, 1H), 2.80–2.93 (m, 1H), 1.91 (m, 1H), 1.71–1.83 (m, 1H), 1.46–1.60 (m, 2H)

Example 99

General Procedure (H)

(R) 2-[8-(3-Amino-piperidin-1-yl)-7-benzyl-3-methyl-2,6-dioxo-2,3,6,7-tetrahydro-purin-1-yl]-N-pyridin-3-yl-acetamide

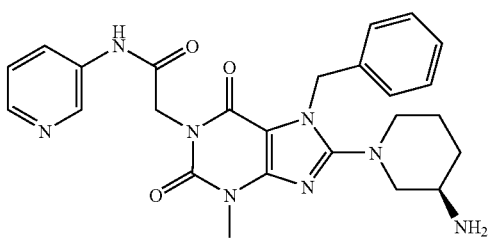

$^1$H-NMR (DMSO-d$_6$, 400 MHz) δ: 10.52 (br, 1H), 8.76 (s, 1H), 8.31 (d, 1H), 7.85–8.05 (m, 5H), 7.56–7.70 (m, 2H), 7.38–7.46 (m, 1H), 7.24–7.38 (m, 3H), 7.19 (d, 2H), 5.38 (s, 2H), 4.67 (s, 2H), 3.52 (m, 1H), 3.45 (s, 3H), 3.13–3.25 (m, 1H), 3.01–3.13 (m, 1H), 2.98 (s, 1H), 2.81–2.94 (m, 1H), 1.90–2.01 (m, 1H), 1.70–1.82 (m, 1H), 1.45–1.61 (m, 2H)

Example 100

General Procedure (H)

(R) 2-[8-(3-Amino-piperidin-1-yl)-7-(2-cyano-benzyl)-3-methyl-2,6-dioxo-2,3,6,7-tetrahydro-purin-1-yl]-N-(6-amino-pyridin-2-yl)-acetamide

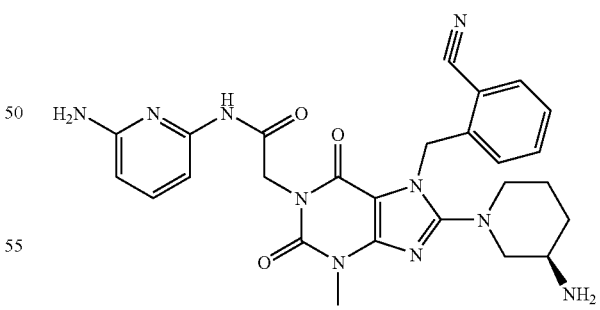

$^1$H-NMR (DMSO-d$_6$, 400 MHz) δ: 7.85–8.02 (m, 4H), 7.59–7.68 (m, 1H), 7.45–7.55 (m, 1H), 7.32–7.43 (m, 1H), 7.07 (d, 1H), 6.18–6.24 (m, 1H), 5.53 (s, 2H), 4.49 (s, 2H), 3.57 (m, 1H), 3.44 (s, 3H), 3.29 (s, 1H), 3.07–3.23 (m, 2H), 2.95 (s, 3H), 2.94–2.88 (M, 1H), 1.89 (m, 1H), 1.74–1.85 (m, 1H), 1.49 (m, 2H)

Example 101

General Procedure (H)

(R) 2-[8-(3-Amino-piperidin-1-yl)-7-(2-cyano-benzyl)-3-methyl-2,6-dioxo-2,3,6,7-tetrahydro-purin-1-yl]-N-pyridin-2-yl-acetamide

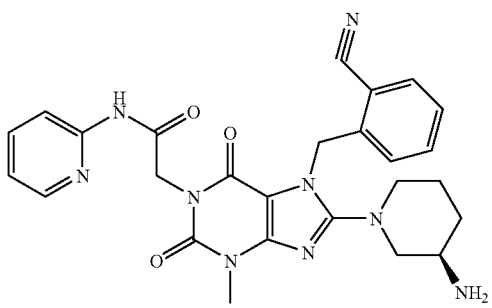

$^1$H-NMR (DMSO-d$_6$, 400 MHz) δ: 10.74 (s, 1H), 8.32 (s, 1H), 7.83–8.05 (m, 5H), 7.70–7.83 (m, 1H), 7.59–7.70 (m, 1H), 7.45–7.59 (m, 1H), 7.03–7.17 (m, 2H), 5.54 (s, 2H), 4.64 (s, 2H), 3.54–3.69 (m, 1H), 3.40 (s, 3H), 3.18–3.50 (m, 4H), 3.0 (s, 3H), 1.87 (m, 1H), 1.70–1.87 (m, 1H), 1.47–1.64 (m, 2H).

Example 102

General Procedure (H)

(R) 2-[8-(3-Amino-piperidin-1-yl)-7-(2-cyano-benzyl)-3-methyl-2,6-dioxo-2,3,6,7-tetrahydro-purin-1-yl]-N-(3-hydroxy-pyridin-2-yl)-acetamide

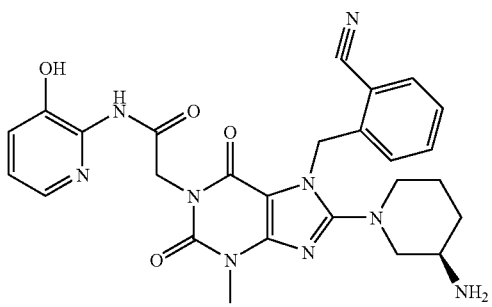

$^1$H-NMR (DMSO-d$_6$, 400 MHz) δ: 7.96 (br, 3H), 7.84–7.90 (m, 2H), 7.65 (t, 1H), 7.49 (t, 1H), 7.32 (d, 1H), 7.13–7.19 (m, 1H), 7.08 (d, 1H), 5.52 (s, 2H), 4.75 (s, 2H), 3.53–3.61 (m, 1H), 3.40 (s, 3H), 3.08–3.23 (m, 2H), 3.05 (s, 2H), 2.90–3.05 (M, 1H), 1.90–2.00 (m, 1H), 1.72–1.84 (m, 1H), 1.48–1.65 (m, 2H)

Example 103

General Procedure (E)

(R) 8-(3-Amino-piperidin-1-yl)-1,3-dimethyl-7-thiophen-2-ylmethyl-3,7-dihydro-purine-2,6-dione

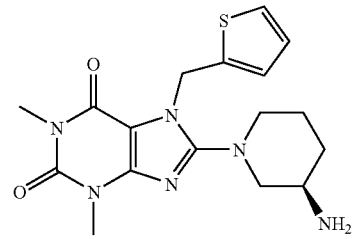

$^1$H-NMR (CDCl$_3$, 200 MHz) δ: 8.40 (br. 3H), 7.18 (d, 1H), 7.03 (d, 1H), 6.88 (m, 1H), 5.5 (s, 2H), 3.70–3.55 (m, 2H), 3.45 (s, 3H), 3.37 (s, 3H), 3.30–3.00 (m, 3H), 2.20–1.55 (m, 4H).
$^{13}$C-NMR (CDCl$_3$, 200 MHz) δ:155.15, 154.73, 151.60, 147.04, 138.04, 127.08, 127.01, 126.18, 104.75, 52.16, 51.44, 46.71, 43.53, 29.73, 27.99, 27.65, 21.07.

The invention claimed is:
1. A compound of formula I

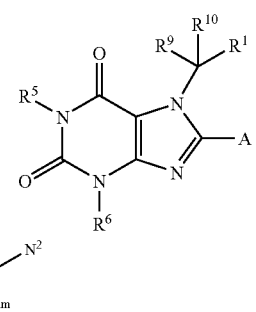

Formula I wherein
A may be attached at either N$^1$ or at N$^2$ to the purine system, wherein if A is attached at N$^1$ then N$^2$ is NH$_2$, and if A is attached at N$^2$ then N$^1$ and N$^2$ are NH, and
n is one or two,
m is one, two, or three,
R$^1$ is aryl optionally substituted with one or more R$^2$ independently or heteroaryl optionally substituted with one or more R$^2$ independently,
R$^2$ is H, C$_1$–C$_7$ alkyl, C$_2$–C$_7$ alkenyl, C$_2$–C$_7$ alkynyl, C$_3$–C$_7$ cycloalkyl, C$_3$–C$_7$ cycloheteroalkyl, —NH-COR$^3$, —NHSO$_2$R$^3$, —SR$^3$, —SOR$^3$, —SO$_2$R$^3$, —OCOR$^3$, —CO$_2$R$^4$, —CON(R$^4$)$_2$, —CSN(R$^4$)$_2$, —NHCON(R$^4$)$_2$, —NHCSN(R$^4$)$_2$, —NHCONH$_2$, —SO$_2$N(R$^4$)$_2$, —OR$^4$, cyano, nitro, or halogen, wherein each alkyl, alkenyl, alkynyl, cycloalkyl and cycloheteroalkyl is optionally substituted with one or more R$^3$ independently,
R$^3$ is Halogen, C$_1$–C$_{10}$ alkyl, C$_2$–C$_{10}$ alkenyl, C$_2$–C$_{10}$ alkynyl, C$_3$–C$_7$ cycloalkyl, aryl, heteroaryl, —OR$^{11}$, —N(R$^{11}$)$_2$, or —SR$^{11}$, wherein each alkyl, alkenyl, alkynyl, cycloalkyl, aryl and heteroaryl is substituted with one or more R$^{11}$ independently, R⁴ is H, $C_1$–$C_{10}$ alkyl, $C_2$–$C_{10}$ alkenyl, $C_2$–$C_{10}$ alkynyl, $C_3$–$C_7$ cycloalkyl, $C_3$–$C_7$ cycloheteroalkyl, aryl, aryl-$C_1$–$C_5$ alkyl, heteroaryl, or heteroaryl-$C_1$–$C_5$ alkyl, wherein each alkyl, alkenyl, alkynyl, cycloalkyl, cycloheteroalkyl, aryl, aryl-$C_1$–$C_5$ alkyl, heteroaryl, and heteroaryl-$C_1$–$C_5$ alkyl is substituted with one or more $R^{11}$ independently, R⁵ is H, $C_1$–$C_{10}$ alkyl, $C_2$–$C_{10}$ alkenyl, $C_2$–$C_{10}$ alkynyl, $C_3$–$C_7$ cycloalkyl, $C_3$–$C_7$ cycloalkyl-$C_1$–$C_5$ alkyl, $C_3$–$C_7$ cycloheteroalkyl, $C_3$–$C_7$ cycloheteroalkyl-$C_1$–$C_5$ alkyl, aryl, heteroaryl, aryl-$C_1$–$C_5$ alkyl, heteroaryl-$C_1$–$C_5$ alkyl, —OR⁷, or —[($CH_2$)$_o$—O]$_p$-alkyl, wherein o and p are 1–3 independently, and wherein each alkyl, alkenyl, alkynyl, cycloalkyl, cycloalkyl-$C_1$–$C_5$ alkyl, cycloheteroalkyl, $C_3$–$C_7$ cycloheteroalkyl-$C_1$–$C_5$ alkyl, aryl, aryl-$C_1$–$C_5$ alkyl, heteroaryl, and heteroaryl-$C_1$–$C_5$ alkyl is optionally substituted with one or more substituents independently selected from $R^7$ or $R^{11}$ independently, R⁶ is $C_1$–$C_{10}$ alkyl, $C_2$–$C_{10}$ alkenyl, $C_2$–$C_{10}$ alkynyl, $C_3$–$C_7$ cycloalkyl, $C_3$–$C_7$ cycloheteroalkyl, aryl, heteroaryl, aryl-$C_1$–$C_5$ alkyl, heteroaryl-$C_1$–$C_5$ alkyl, or $C_3$–$C_7$ cycloheteroalkyl-$C_1$–$C_5$ alkyl, wherein each alkyl, alkenyl, alkynyl, cycloalkyl, cycloheteroalkyl, $C_3$–$C_7$ cycloheteroalkyl-$C_1$–$C_5$ alkyl, aryl, aryl-$C_1$–$C_5$ alkyl, heteroaryl, aryl-$C_1$–$C_5$ alkyl, and heteroaryl-$C_1$–$C_5$ alkyl is optionally substituted with one or more $R^{11}$ independently, R⁷ is H, =O, $C_1$–$C_{10}$ alkyl, $C_2$–$C_{10}$ alkenyl, $C_2$–$C_{10}$ alkynyl, $C_3$–$C_7$ cycloalkyl, $C_3$–$C_7$ cycloheteroalkyl, aryl, heteroaryl, —OR¹¹, —N(R¹¹)$_2$, or —SR¹¹, wherein each alkyl, alkenyl, alkynyl, cycloalkyl, cycloheteroalkyl, aryl, and heteroaryl is optionally substituted with one or more $R^{11}$ independently, R⁸ is $C_1$–$C_{10}$ alkyl, $C_2$–$C_{10}$ alkenyl, $C_2$–$C_{10}$ alkynyl, $C_3$–$C_7$ cycloalkyl, $C_3$–$C_7$ cycloheteroalkyl, aryl, heteroaryl, —OR¹¹, —N(R¹¹)$_2$, or —SR¹¹, wherein each alkyl, alkenyl, alkynyl, cycloalkyl, cycloheteroalkyl, aryl, and heteroaryl is optionally substituted with one or more $R^{11}$ independently, R⁹ and R¹⁰ is independently H, $C_1$–$C_{10}$ alkyl optionally substituted with one or more $R^8$ independently, or halogen, R¹¹ is H, —CF₃, —CCl₃, —OCF₃, —OMe, cyano, halogen, —OH, —COMe, —CONH₂, —CONHMe, —CONMe₂, —NO₂, $C_1$–$C_{10}$ alkyl, aryl, heteroaryl, $C_3$–$C_7$ cycloalkyl, or $C_3$–$C_7$ cycloheteroalkyl, wherein each alkyl, cycloalkyl, cycloheteroalkyl, aryl, and heteroaryl is optionally substituted with one or more $R^{12}$ independently, R¹² is H, $C_1$–$C_{10}$ alkyl, —CF₃, —CCl₃, —OCF₃, —OMe, cyano, halogen, —OH, —COMe, —CONH₂, —CONHMe, —CONMe₂, —NH₂, or —NO₂

R⁹ and R¹⁰ with the carbon atom to which they are attached may form a cyclopropyl ring, if two R⁴ or two R¹¹ are attached to the same nitrogen, they may be connected with the nitrogen atom to which they are attached to form a 3- to 7-membered ring, wherein the compound is selected from the following:

2-(8-(3-Aminopiperidin-1-yl)-1,3-dimethyl-2,6-dioxo-1,2,3,6-tetrahydropurin-7-ylmethyl)benzonitrile, 8-(3-Aminopyrrolidin-1-yl)-7-benzyl-1,3-dimethyl-3,7-dihydropurine-2,6-dione, (S) 8-(3-Aminopyrrolidin-1-yl)-7-benzyl-1,3-dimethyl-3,7-dihydropurine-2,6-dione, 2-(8-(3-Aminopyrrolidin-1-yl)-1,3-dimethyl-2,6-dioxo-1,2,3,6-tetrahydropurin-7-ylmethyl)benzonitrile, 8-(3-Aminopyrrolidin-1-yl)-7-(2-iodobenzyl)-1,3-dimethyl-3,7-dihydropurine-2,6-dione, 8-(3-Aminoazepan-1-yl)-7-benzyl-1,3-dimethyl-3,7-dihydropurine-2,6-dione, (S) 8-(3-Aminopyrrolidin-1yl)-7-(2-iodobenzyl)-1,3-dimethyl-3,7-dihydropurine-2,6-dione, (S) 2-(8-(3-Aminopyrrolidin-1-yl)-1,3-dimethyl-2,6-dioxo-1,2,3,6-tetrahydropurin-7-ylmethyl)benzonitrile, 8-(3-Aminopiperidin-1-yl)-7-(2-iodobenzyl)-1,3-dimethyl-3,7-dihydropurine-2,6-dione, 8-(3-Aminopiperidin-1-yl)-7-(2-bromobenzyl)-1,3-dimethyl-3,7-dihydropurine-2,6-dione, (R) 8-(3-Aminopyrrolidin-1-yl)-7-(2-bromobenzyl)-1,3-dimethyl-3,7-dihydropurine-2,6-dione, (S) 8-(3-Aminopyrrolidin-1-yl)-7-(2-bromobenzyl)-1,3-dimethyl-3,7-dihydropurine-2,6-dione, (R) 8-(3-Aminopyrrolidin-1-yl)-7-benzyl-1,3-dimethyl-3,7-dihydropurine-2,6-dione, (R) 2-(8-(3-Aminopyrrolidin-1-yl)-1,3-dimethyl-2,6-dioxo-1,2,3,6-tetrahydropurin-7ylmethyl)benzonitrile, (R) 8-(3-Aminopyrrolidin-1-yl)-7-(2iodobenzyl)-1,3-dimethyl-3,7-dihydropurine-2,6-dione, (R) 2-[8-(3-Aminopiperidin-1-yl)-1,3-dimethyl-2,6-dioxo-1,2,3,6-tetrahydropurin-7-ylmethyl]-benzonitrile, (R) 8-(3-Aminopiperidin-1-yl)-7-benzyl-1,3-dimethyl-3,7-dihydropurine-2,6-dione, (R) 8-(3-Aminopiperidin-1-yl)-1,3dimethyl-7-(2-methylbenzyl)-3,7-dihydropurine-2,6-dione, (R) 8-(3-Aminopiperidin-1-yl)-7-(2-chlorobenzyl)-1,3-dimethyl-3,7-dihydropurine-2,6-dione, (R) 8-(3-Aminopiperidin-1-yl)-7-(2-bromobenzyl)-1,3-dimethyl-3,7-dihyropurine-2,6-dione, (R) 8-(3-Aminopiperidin-1-yl)-7-(2-bromobenzyl)-3-methyl-1-(2-oxo-2-phenylethyl)-3,7-dihydro-purine-2,6-dione, (R) 8-(3-Aminopiperidin-1-yl)-7-(2-bromobenzyl)-3-methyl-1-phenethyl-3,7-dihydropurine-2,6-dione, (R) 8-(3-Aminopiperidin-1-yl)-7-(2-chlorobenzyl)-3-methyl-1-phenethyl-3,7-dihydropurine-2,6-dione, (R) 2-[8-(3-Aminopiperidin-1-yl)-7-(2-chlorobenzyl)-3-methyl-2,6-dioxo-1,2,3,6-tetrahydropurin-1-ylmethyl]benzonitrile, 2-[8-(3-Aminopiperidin-1-yl)-7-(2-cyanobenzyl)-3-methyl-2,6-dioxo-1,2,3,6-tetrahydropurin-1-ylmethyl]benzonitrile, (R) 2-[8-(3-Aminopiperidin-1-yl)-7-(2-cyanobenzyl)-3-methyl-2,6-dioxo-1,2,3,6-tetrahydropurin-1-ylmethyl]benzonitrile, (R) 2-[8-(3-(R)-Aminopiperidin-1-yl)-3-methyl-2,6-dioxo-1,2,3,6-tetrahydropurin-7-ylmethyl]benzonitrile, (R) 8-(3-Aminopiperidin-1-yl)-7-(2-chlorobenzyl)-3-methyl-3,7-dihydropurine-2,6-dione, (R) 8-(3-Aminopiperidin-1-yl)-7-(2-bromobenzyl)-3-methyl-1-(2-oxo-2-thiophen-3-yl-ethyl)-3,7-dihydropurine-2,6-dione, (R) 2-[8-(3-Aminopiperidin-1-yl)-3-methyl-2,6-dioxo-1-(2-oxo-2-thiophen-3-yl-ethyl)-1,2,3,6-tetrahydropurin-7-ylmethyl]benzonitrile, 8-(3-Amino-piperidin-1-yl)-3-benzyl-7-(3-fluoro-benzyl)-3,7-dihydro-purine-2,6-dione, 8-(3-Amino-piperidin-1-yl)-3-benzyl-7-(2-chloro-benzyl)-3,7-dihydro-purine-2,6-dione, 8-(3-Amino-piperidin-1-yl)-3-benzyl-7-(2-bromo-benzyl)-3,7-dihydro-purine-2,6-dione, 8-(3-Amino-piperidin-1-yl)-3-benzyl-7-(2-methyl-benzyl)-3,7-dihydro-purine-2,6-dione, 8-(3-Amino-piperidin-1-yl)-3,7-dibenzyl-3,7-dihydro-purine-2,6-dione,
8-(3-Amino-piperidin-1-yl)-3-benzyl-7-(3,5-difluoro-benzyl)-3,7-dihydro-purine-2,6-dione,
8-(3-Amino-piperidin-1-yl)-3-benzyl-7-(2,5-difluoro-benzyl)-3,7-dihydro-purine-2,6-dione,
8-(3-Amino-piperidin-1-yl)-3-benzyl-7-(2-difluoromethoxy-benzyl)-3,7dihydro-purine-2,6-dione,
8-(3-Amino-piperidin-1-yl)-7-(3-fluoro-benzyl)-3-methyl-3,7-dihydro-purine-2,6-dione,
8-(3-Amino-piperidin-1-yl)-7-(2-chloro-benzyl)-3-methyl-3,7-dihydro-purine-2,6-dione,
8-(3-Amino-piperidin-1-yl)-3-methyl-7-(2methyl-benzyl)-3,7-dihydro-purine-2,6-dione,
8-(3-Amino-piperidin-1-yl)-7-benzyl-3-methyl-3,7-dihydro-purine-2,6-dione,
8-(3-Amino-piperidin-1-yl)-7-(3,5-difluoro-benzyl)-3-methyl-3,7-dihydro-purine-2,6-dione,
8-(3-Amino-piperidin-1-yl)-7-(3-fluoro-benzyl)-1,3-dimethyl-3,7-dihydro-purine-2,6-dione,
8-(3-Amino-piperidin-1-yl)-1,3-dimethyl-7-(2-methyl-benzyl)-3,7-dihydro-purine-2,6-dione,
8-(3-Amino-piperidin-1-yl)-7-(3,5-difluoro-benzyl)-1,3-dimethyl-3,7-dihydro-purine-2,6-dione,
8-(3-Amino-piperidin-1-yl)-7-(2,5-difluoro-benzyl)1,3-dimethyl-3,7-dihydro-purine-2,6-dione,
8-(3-Amino-piperidin-1-yl)-7-(2-difluoromethoxy-benzyl)-1,3-dimethyl-3,7-dihydro-purine-2,6-dione,
8-(3-Amino-piperidin-1-yl)-7-(2-chloro-benzyl)-3-methyl-1-(2-oxo-2-phenyl-ethyl)-3,7-dihydro-purine-2,6-dione,
8-(R-3-Amino-piperidin-1-yl)-7-(2-chloro-benzyl)-3-methyl-1-(2-oxo-2-phenyl-ethyl)-3,7-dihydro-purine-2,6-dione,
2-[8-(3-Aminopiperidin-1-yl)-7-(2-bromobenzyl)-3-methyl-2,6-dioxo-1,2,3,6-tetrahydropurin-1-ylmethyl]benzonitrile,
8-(3-Amino-piperidin-1-yl)-7-(2-bromo-benzyl)-3-methyl-1-(2-oxo-2-phenyl-ethyl)-3,7-dihydro-purine-2,6-dione,
8-(3-Amino-piperidin-1-yl)-3-methyl-1-(2-oxo-2-phenyl-ethyl)-7-(2-trifluoromethyl-benzyl)-3,7-dihydro-purine-2,6-dione,
8-(3-Amino-piperidin-1-yl)-1-(2-benzo[b]thiophen-3-yl-2-oxo-ethyl)-7-(2-chloro-benzyl)-3-methyl-3,7-dihydro-purine-2,6-dione,
8-(3-Amino-piperidin-1yl)-7-(2-chloro-benzyl)-1-[2(3-fluoro-phenyl)-2-oxo-ethyl]-3-methyl-3,7-dihydro-purine-2,6-dione,
8-(3-Amino-piperidin-1-yl)-7-(2-bromo-benzyl)_1-(2-cyclopropyl-2-oxo-ethyl)-3-methyl-3,7-dihydro-purine-2,6-dione,
8-(3-Amino-piperidin-1yl)-7-(2-bromo-benzyl)-1-[2-(2,6-dimethoxy-phenyl)-2-oxo-ethyl]-3-methyl-3,7-dihydro-purine-2,6-dione,
8-(3-Amino-piperidin-1-yl)-7-(2-bromo-benzyl)-3-methyl-1-(2-oxo-2-thiophen-3-yl-ethyl)-3,7-dihydro-purine-2,6-dione,
8-(3-Amino-piperidin-1-yl)-7-(2-bromo-benzyl)-1-[2-(4-chloro-phenyl)-2-oxo-ethyl]-3-methyl-3,7-dihydro-purine-2,6-dione,
8-(3-Amino-piperidin-1-yl)-7-(2-bromo-benzyl)-3-methyl-1-(2-oxo-2-p-tolyl-ethyl)-3,7-dihydro-purine-2,6-dione,
8-(3-Amino-piperidin-1-yl)-7-(2-bromo-benzyl)-1-[2-(2-chloro-phenyl)-2-oxo-ethyl]-3-methyl-3,7-dihydro-purine-2,6-dione,
8-(3-Amino-piperidin-1-yl)-7-(2-bromo-benzyl)-1-[2-(3-methoxy-phenyl)-2-oxo-ethyl]-3-methyl-3,7-dihydro-purine-2,6-dione,
8-(3-Amino-piperidin-1-yl)-7-(2-bromo-benzyl)-1-[2-(2-methoxy-phenyl)-2-oxo-ethyl]3-methyl-3,7-dihydro-purine-2,6-dione,
8-(3-Amino-piperidin-1-yl)-7-(2-bromo-benzyl)-3-methyl-1-(2-oxo-butyl-3,7-dihydro-purine-2,6-dione,
8-(3-Amino-piperidin-1-yl)-7-(2-bromo-benzyl)-3-methyl-1-(2-oxo-1-phenyl-pyrrolidin-3-yl)-3,7-dihydro-purine-2,6-dione,
8-(3-Amino-piperidin-1-yl)-7-(2-bromo-benzyl)-1-[2-(3-chloro-phenyl]3-methyl-3,7-dihydro-purine-2,6-dione,
2-{8-(3-Amino-piperidin-1-yl)-1-[2-(2,6-difluoro-phenyl)-2-oxo-ethyl]-3-methyl-2,6-dioxo-1,2,3,6-tetrahydro-purin-7-ylmethyl}-benzonitrile,
2-[8-(3-Amino-piperidin-1-yl)-3-methyl-2,6-dioxo-1-(2-oxo-2-thiophen-3-yl-ethyl)-1,2,3,6-tetrahydro-purine-7-ylmethyl]-benzonitrile,
2-[8-(3-Amino-piperidin-1yl)-1-(2-benzo[b]thiophen-3-yl-2-oxo-ethyl)-3-methyl-2,6-dioxo-1,2,3,6-tetrahydro-purin-7-ylmethyl]-benzonitrile,
2-[8-(3-Amino-piperidin-1-yl)-3-methyl-2,6-dioxo-1-(2-oxo-2-phenyl-ethyl)-1,2,3,6-tetrahydro-purin-7-ylmethyl]-benzonitrile,
2-{8-(3-Amino-piperidin-1-yl)-1-[2-(3-fluoro-phenyl)-2-oxo-ethyl]-3-methyl-2,6-dioxo-1,2,3,6-tetrahydro-purin-7-ylmethyl}-benzonitrile,
8-(3-Amino-piperidin-1-yl)-3-methyl-1-(2-oxo-2-phenyl-ethyl)-7-(3-trifluoromethoxy-benzyl)-3,7-dihydro-purine-2,6-dione,
8-(3-Amino-piperidin-1-yl)-7-(2-fluoro-6-trifluoromethyl-benzyl)-3-methyl-1-(2-oxo-2-phenyl-ethyl)-3,7-dihydro-purine-2,6-dione,
8-(3-Amino-piperidin-1-yl)-7-(2-fluoro-5-trifluoromethyl-benzyl)-3-methyl-1-(2-oxo-2-phenyl-ethyl)-3,7-dihydro-purine-2,6-dione,
2-(8-(3-Aminoazepan-1-yl)-7-(2-chlorobenzyl)-3-methyl-2,6-dioxo-1,2,3,6-tetrahydropurin-1-ylmethyl)benzonitrile,
8-(3-Aminoazepan-1-yl)-7-(2chlorobenzyl)3-methyl-3,7-dihydropurine-2,6-dione,
8-(3-Aminoazepan-1-yl)-7-benzyl-3-methyl-1-(2-oxo-2-phenylethyl)-3,7-dihydropurine-2,6-dione,
8-(3-Aminoazepan-1-yl)-7-benzyl-3-methyl-3,7-dihydro-purine-2,6-dione,
2-(8-(3-Aminoazepan-1-yl)-3-methyl-2,6-dioxo-1,2,3,6-tetrahydropurin-7-ylmethyl)benzonitrile,
8-(3-Aminoazepan-1-yl)-7-(2-bromobenzyl)-3-methyl-3,7-dihydropurine-2,6-dione,
8-(3-Aminoazepan-1-yl)-3-methyl-7-(2-trifluoromethyl-benzyl)-3,7-dihydropurine-2,6-dione,
8-(3-Aminoazepan-1-yl)-3-methyl-7-(2-methylbenzyl)-3,7-dihydropurine-2,6-dione,
8-(3-Aminoazepan-1-yl)-7-(2-bromobenzyl)-1,3-dimethyl-3,7-dihydropurine-2,6-dione,
2-[8-(3-Aminoazepan-1-yl)-1,3-dimethyl-2,6-dioxo-1,2,3,6-tetrahydropurin-7-ylmethyl]benzonitrile,
8-(3-Aminoazepan-1-yl)-1,3-dimethyl-7-(2-methylbenzyl)-3,7-dihydropurine-2,6-dione,
8-(3-Amino-azepan-1-yl)-7-(2-chloro-benzyl)-1,3-dimethyl-3,7-dihydro-purine-2,6-dione,
(R) 2-[8-(3-Amino-piperidin-1-yl)-7-(2-chloro-benzyl)-3-methyl-2,6-dioxo-2,3,6,7-tetrahydro-purin-1-yl]-N-pyridin-2-yl-acetamide, (R) 2-[8-(3-Amino-piperidin-1-yl)-7-(2-chloro-benzyl)-3-methyl-2,6-dioxo-2,3,6,7-tetrahydro-purin-1-yl]-N-cyclohexyl-acetamide, (R) 8-(3-Amino-piperidin-1-yl)-7-(2-chloro-benzyl)-3-methyl-1-(2-oxo-2-pyrrolidin-1-yl-ethyl)-3,7-dihydro-purine-2,6-dione, (R) 2-[8-(3-Aminopiperidin-1-yl)-7-(2-chlorobenzyl)-3-methyl-2,6-dioxo-2,3,6,7-tetrahydro-purin-1-yl]-N-cyclopentylacetamide, 2-[8-(3-(R) Amino-piperidin-1-yl)-7-(2-chloro-benzyl)-3-methyl-2,6-diozo-2,3,6,7-tetrahydro-purin-1-yl]-N-(1-aza-bicyclo[2.2.2]oct-3-yl)-acetamide, (R) 2-[8-(3-Amino-piperidin-1-yl)-7-(2-chloro-benzyl)-3-methyl-2,6-dioxo-2,3,6,7-tetrahydro-purin-1-yl]-N-(3-hydroxy-pyridin-2-yl)-acetamide, (R,R) 8-(3-Amino-piperidin-1-yl)-7-(2-chloro-benzyl)-1-[2-(3-hydroxy-pyrrolidin-1-yl)-2-oxo-ethyl]-3-methyl-3,7-dihydro-purine-2,6dione, (R) 2-[8-(3-Amino-piperidin-1-yl)-7-benzyl-3-methyl-2,6-dioxo-2,3,6,7-tetrahydro-purin-1-yl]-N-pyridin-2-yl-acetamide, (R) 2-[8-(3-Amino-piperidin-1-yl)-7-benzyl-3-methyl-2,6-dioxo-2,3,6,7-tetrahydro-purin-1-yl]-N-cyclohexyl-acetamide, (R) 2-[8-(3-Amino-piperidin-1-yl)-7-benzyl-3-methyl-2,6-dioxo-2,3,6,7-tetrahydro-purin-1-yl]-N-cyclopentyl-acetamide, 2-[8-(3-(R)-Amino-piperidin-1-yl)-7-benzyl-3-methyl-2,6-dioxo-2,3,6,7-tetrahydro-purin-1-yl]-N-(1-aza-bicyclo[2.2.2]oct-3-yl)-acetamide, (R) 2-[8-(3-Amino-piperidin-1-yl)-7-benzyl-3-methyl-2,6-dioxo-2,3,6,7-tetrahydro-purin-1-yl]-N-(3-hydroxy-pyridin-2-yl)-acetamide, (R) 2-[8-(3-Amino-piperidin-1-yl)-7-benzyl-3-methyl-2,6-dioxo-2,3,6,7-tetrahydro-purin-1-yl]-N-pyridin-3-yl-acetamide, (R) 2-[8-(3-Amino-piperidin-1-yl)-7-(2-cyano-benzyl)-3-methyl-2,6-dioxo-2,3,6,7-tetrahydro-purin-1-yl]-N-(6-amino-pyridin-2-yl)-acetamide, (R) 2-[8-(3-Amino-piperidin-1-yl)-7-(2-cyano-benzyl)-3-methyl-2,6-dioxo-2,3,6,7tetrahydro-purin-1-yl]-N-pyridin-2-yl-acetamide, (R) 2-[8-(3-Amino-piperidin-1-yl)-7-(2cyano-benzyl)-3-methyl-2,6-dioxo-2,3,6,7-tetrahydro-purin-1-yl]-N-(3-hydroxy-pyridin-2-yl)-acetamide, and (R) 8-(3-Amino-piperidin-1-yl)-1,3-dimethyl-7-thiophen-2-ylmethyl-3,7-dihydro-purine-2,6-dione;

or any tantomeric form or any optical isomer or mixture of optical isomers, racemic mixture, or a salt thereof with a pharmaceutically acceptable acid or base.

2. A method for treating type II diabetes, said method comprising administering to a patient in need thereof an effective amount for said treatment of a compound according to claim 1 or a pharmaceutically acceptable salt thereof with a pharmaceutically acceptable acid or base, or any optical isomer or mixture of optical isomers, racemic mixture, or any tautomeric form thereof.

3. A pharmaceutical composition for treatment of type II diabetes, comprising (i) a compound according to claim 1 or a pharmaceutically acceptable salt thereof with a pharmaceutically acceptable acid or base, or any optical isomer or mixture of optical isomers, racemic mixture, or any tautomeric form and (ii) one or more pharmaceutically acceptable carriers or diluents.

* * * * *